(12) United States Patent
Jansen et al.

(10) Patent No.: US 8,303,844 B2
(45) Date of Patent: Nov. 6, 2012

(54) BENZO[F]CHROME ANY PYRANO[3,2-F]CHROME DERIVATIVES FOR USE IN LIQUID CRYSTAL MEDIA

(75) Inventors: Axel Jansen, Darmstadt (DE); Melanie Klasen-Memmer, Heuchelheim (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 329 days.

(21) Appl. No.: 12/744,804

(22) PCT Filed: Nov. 3, 2008

(86) PCT No.: PCT/EP2008/009242
§ 371 (c)(1),
(2), (4) Date: May 26, 2010

(87) PCT Pub. No.: WO2009/068152
PCT Pub. Date: Jun. 4, 2009

(65) Prior Publication Data
US 2011/0043746 A1   Feb. 24, 2011

(30) Foreign Application Priority Data
Nov. 27, 2007   (DE) .................. 10 2007 057 028

(51) Int. Cl.
C09K 19/32    (2006.01)
C09K 19/34    (2006.01)
C09K 19/06    (2006.01)
C07D 493/00   (2006.01)
G02F 1/1333   (2006.01)

(52) U.S. Cl. ......... 252/299.62; 252/299.01; 252/299.61; 252/299.63; 428/1.1; 549/387; 549/388; 549/389; 549/390; 349/1; 349/56; 349/182; 349/183

(58) Field of Classification Search ............ 736/1.1; 252/299.01, 299.6, 299.61, 299.62, 299.63; 549/387–390; 349/1, 56, 182, 183
See application file for complete search history.

(56) References Cited

U.S. PATENT DOCUMENTS

| 7,326,447 | B2 * | 2/2008 | Taugerbeck et al. | 428/1.1 |
| 7,678,929 | B2 * | 3/2010 | Jansen et al. | 549/387 |
| 7,824,745 | B2 * | 11/2010 | Taugerbeck et al. | 428/1.1 |
| 8,029,696 | B2 * | 10/2011 | Kretzschmann et al. | 252/299.6 |

| 2008/0177095 | A1 | 7/2008 | Jansen et al. |
| 2009/0023802 | A1 | 1/2009 | Taugerbeck et al. |
| 2010/0059711 | A1 | 3/2010 | Kretzschmann et al. |

FOREIGN PATENT DOCUMENTS

| EP | 1930396 A1 | 6/2008 |
| WO | 2007079840 A2 | 7/2007 |
| WO | 2008012180 A1 | 1/2008 |
| WO | PCT2008009242 R | 11/2008 |

OTHER PUBLICATIONS

Bilgic, S., et al. "Synthesis of chromans from the reaction of o-quinone methide precursor with substituted styrenes." (Journal of Chemical Research), vol. 2, 76-79, 2007.
Buyukkidan, B., et al. "The synthesis of some novel substituted benzochromene derivates." (Journal of Chemical Research), vol. 11, 749-751, 2003.
Matsumoto J., et al. "Generation of quinone methide from aminomethyl(hydroxyl)arenes precursors in aqueous solution." (Tetrahedron Elsevier Science Publishers), vol. 61, No. 24, 5735-5740, 2005.
Wenkert, E., et al. "A new synthesis of the hydrophenanthrene nucleus." (Journal of the American Chemical Society), vol. 82, 4675-4680, 1960.
Zhangjie S., et al. "Direct Functionalization of Arenes by Primary Alcohol Solfonate Esters Catalyzed by Gold (III)." (Journal of the American Chemical Society), vol. 126, No. 1, 13596-13597, 2004.

\* cited by examiner

*Primary Examiner* — Geraldina Visconti
(74) *Attorney, Agent, or Firm* — Millen, White, Zelano & Branigan, P.C.

(57) ABSTRACT

The present invention relates to benzo[f]chromene and pyrano[3,2-f]-chromene derivatives of the formula I

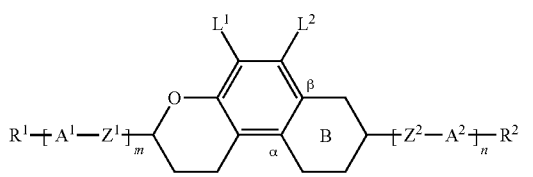

in which
$L^1$, $L^2$, $R^1$, $R^2$, $A^1$, $A^2$, $Z^1$, $Z^2$, m and n are as defined in claim 1, to the preparation thereof, to the use thereof as components in liquid-crystalline media, and to electro-optical display elements which contain the liquid-crystalline media according to the invention.

13 Claims, No Drawings

BENZO[F]CHROME ANY PYRANO[3,2-F]CHROME DERIVATIVES FOR USE IN LIQUID CRYSTAL MEDIA

The present invention relates to benzo[f]chromene and pyrano[3,2-f]-chromene derivatives, to a process for the preparation thereof, to liquid-crystalline media comprising these derivatives, and to electro-optical display elements containing these liquid-crystalline media. In particular, the invention relates to benzo[f]chromene and pyrano[3,2-f]chromene derivatives having negative dielectric anisotropy.

Liquid crystals have found widespread use since the first commercially usable liquid-crystalline compounds were found about 30 years ago. Known areas of application of conventional mixtures are, in particular, displays for watches and pocket calculators, and large display panels as used in railway stations, airports and sports arenas. Further areas of application are displays of portable and desktop computers, navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the dielectric constant $\in$ of the liquid-crystalline medium has different values for the two orientations. Substances whose dielectric constant is larger when the longitudinal axes of the molecules are oriented perpendicular to the capacitor plates than when they are oriented parallel are referred to as dielectrically positive. In other words, if the dielectric constant $\in_{\|}$ parallel to the longitudinal axes of the molecules is larger than the dielectric constant $\in_{\perp}$ perpendicular to the longitudinal axes of the molecules, the dielectric anisotropy $\Delta\in=\in_{\|}-\in_{\perp}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. In the most widespread TN ("twisted nematic") cells, a liquid-crystalline layer with a thickness of only from about 5 to 10 µm is arranged between two plane-parallel glass plates, onto each of which an electrically conductive, transparent layer of tin oxide or indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly with the same orientation, flat or with the same small tilt angle, on the inside of the display surface. Two polarisation films which only enable linear-polarised light to enter and escape are applied to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\in$ is negative in this case. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

Document DE 10 2004 004 228 A1 discloses benzochromene derivatives of the following structure:

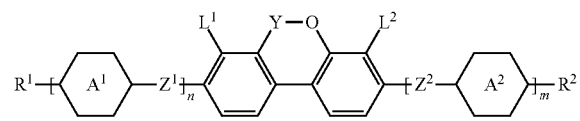

These tricyclic compounds differ from the present invention through the position of the heteroatoms in the rings, the substitution and the degree of saturation of the rings. Further benzochromene derivatives which are partially unsaturated and optionally have a plurality of heteroatoms are, in addition, disclosed in document WO 2007/079840 A2.

It is an object of the present invention to provide compounds having advantageous properties for use in liquid-crystalline media. In particular, they should have negative dielectric anisotropy, which makes them particularly suitable for use in liquid-crystalline media for VA displays. Irrespective of the dielectric anisotropy corresponding to the display type, compounds are desired which have a favourable combination of the applicational parameters. Of these parameters, which are to be optimised simultaneously, particular mention should be made of a high clearing point, a low rotational viscosity, an optical anisotropy in the use range, and the properties which serve to achieve mixtures having the desired liquid-crystalline phases over a broad temperature range.

This object is achieved in accordance with the invention by compounds of the general formula I

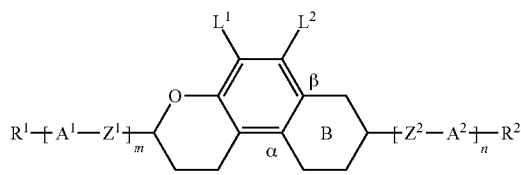

I in which m and n are each, independently of one another, 0, 1, 2 or 3, preferably 0, 1 or 2, where m+n≦4;

$L^1$ and $L^2$ each, independently of one another, denote H, halogen, CN, $CF_3$, $CHF_2$, $CH_2F$ or $CH_3$, preferably H, F, Cl, CN or $CF_3$;

$A^1$ and $A^2$ each, independently of one another, denote
  (a) 1,4-phenylene, in which =CH— may be replaced once or twice by =N— and which may be unsubstituted or mono- to tetrasubstituted, independently of one another, by —CN, —F, —Cl, —Br, —I, $C_1$-$C_6$-alkanyl which is unsubstituted or mono- or polysubstituted by fluorine and/or chlorine, or $C_1$-$C_6$-alkoxy which is unsubstituted or mono- or polysubstituted by fluorine and/or chlorine,
  (b) 1,4-cyclohexylene, 1,4-cyclohexenylene or 1,4-cyclohexadienylene, in which —$CH_2$— may be replaced once or twice, independently of one another, by —O— or —S— in such a way that heteroatoms are not linked directly, and which may be unsubstituted or mono- or polysubstituted by —F and/or —Cl, or
  (c) bicyclo[1.1.1]pentane-1,3-diyl, bicyclo[2.2.2]octane-1,4-diyl or spiro[3.3]heptane-2,6-diyl;

$Z^1$ and $Z^2$ each, independently of one another, denote a single bond, —$CF_2O$—, —$OCF_2$—, —$CH_2CH_2$—, —$CF_2CF_2$—, —$CF_2CH_2$—, —$CH_2CF_2$—, —(CO)O—, —O(CO)—, —$CH_2O$—, —$OCH_2$—, —CF=CH—, —CH=CF—, —CF=CF—, —CH=CH—, —C≡C— or a combination of two of these groups, where O atoms are not linked directly;

$R^1$ and $R^2$, independently of one another, denote hydrogen, an alkanyl, alkoxy, alkenyl or alkynyl radical having 1 to 15 or 2 to 15 C atoms respectively which is unsubstituted, mono-substituted by —CN or mono- or polysubstituted by —F, —Cl and/or —Br, where, in addition, one or more $CH_2$ groups in these radicals may each be replaced, independently of one another, by —O—, —S—, —$SO_2$—, —CO—, —(CO)O—, —O(CO)— or —O(CO)O— in such a way that heteroatoms are not linked directly, or denote —F, —Cl, —Br, —CN, —SCN or —$SF_5$; and ring B denotes

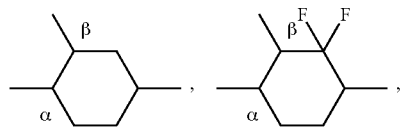

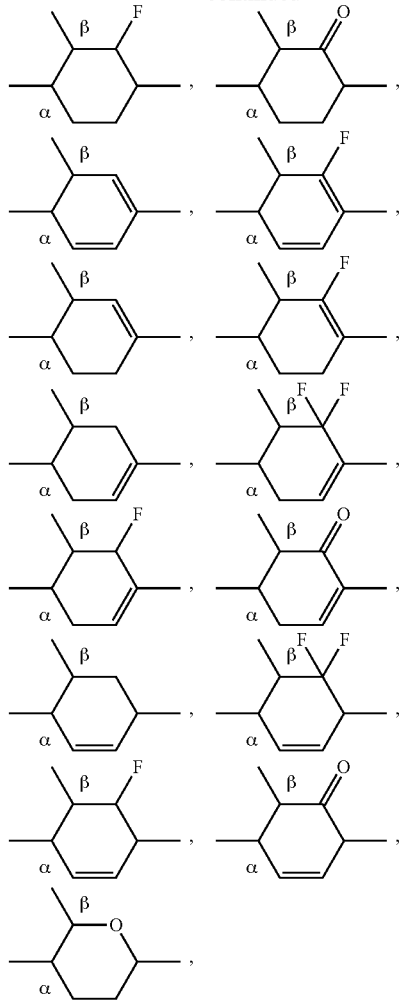

where $A^1$ and $A^2$ or $Z^1$ and $Z^2$ may each have identical or different meanings if m or n is greater than 1, where $R^1$ and $R^2$ do not simultaneously denote H, and where in the case where $R^1$=H and m=0 or $R^2$=H and n=0, then ring B denotes a pyran of the formula

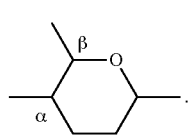

The compounds have predominantly negative Δ∈ and are therefore particularly suitable for use in VA-TFT displays. The compounds according to the invention preferably have a Δ∈ of <−2 and particularly preferably a Δ∈ of <−4. They exhibit very good compatibility with the usual substances used in liquid-crystal mixtures for displays.

Furthermore, the compounds of the formula I according to the invention have values for the optical anisotropy Δn which are particularly suitable for use in VA-TFT displays. The compounds according to the invention preferably have a Δn of greater than 0.05 and less than 0.40.

The other physical, physicochemical or electro-optical parameters of the compounds according to the invention are also advantageous for use of the compounds in liquid-crystalline media. The compounds or liquid-crystalline media comprising these compounds have, in particular, a sufficient breadth of the nematic phase and good low-temperature and long-term stability as well as sufficiently high clearing points. The rotational viscosities of the compounds are advantageously low, particularly for m+n=0.

Of the meanings for the substituents $L^1$ and $L^2$, preference is given to H, F and Cl, in particular H and F. It is furthermore preferred for one or two of the radicals $L^1$ and $L^2$ to denote Cl or F, in particular fluorine. $L^1$ preferably denotes fluorine. $L^1$ and $L^2$ particularly preferably denote F.

In the case where the radical $R^2$ denotes a fluorine atom or fluorinated alkyl, in particular if m simultaneously denotes 0, the formula I then also encompasses compounds which may have an overall positive dielectric anisotropy. Such compounds are then suitable for dielectrically positive liquid-crystal mixtures which are used in displays, such as, for example, of the TN-TFT or IPS ('in-plane switching') type. The requirements of the other physical parameters, such as, for example, the viscosity, are substantially congruent over most applications. The said compounds are thus equally suitable for these purposes since they have favourable values for the parameters, such as rotational viscosity, Δn, etc., and are suitable for the preparation of liquid-crystalline mixtures.

$A^1$ and $A^2$ are preferably and independently of one another an optionally substituted 1,4-phenylene, an optionally substituted 1,4-cyclohexylene, in which —CH$_2$— may be replaced once or twice by —O—, or an optionally substituted 1,4-cyclohexenylene. If n or m is 2, the rings $A^1$ and $A^2$ may adopt identical or different meanings.

$A^1$ and $A^2$ are particularly preferably, independently of one another,

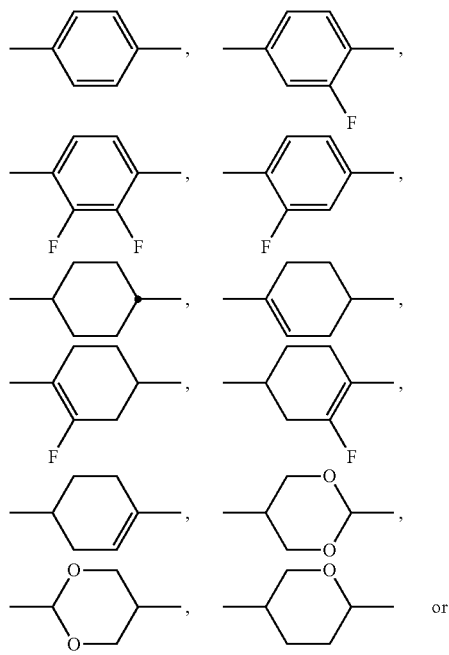

-continued

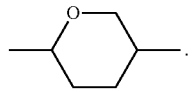

$A^1$ and $A^2$ are very particularly preferably 1,4-cyclohexylene and/or optionally fluorine-substituted 1,4-phenylene.

In a preferred embodiment of the invention, m+n is equal to 1, and $A^1$, $A^2$, independently of one another, denote

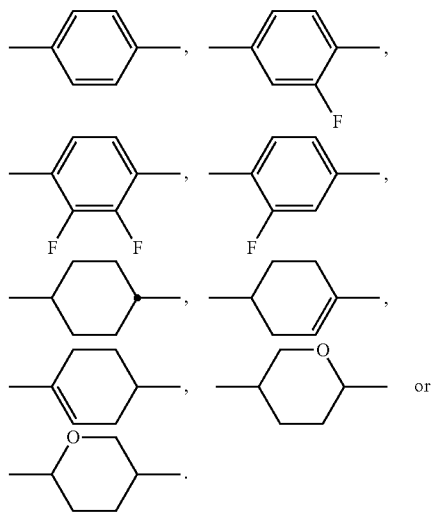

$Z^1$ and $Z^2$ are preferably, independently of one another, a single bond, —CH$_2$O—, —OCH$_2$—, —CF$_2$O—, —OCF$_2$—, —CF$_2$CF$_2$—, —CH=CH—, —CF=CH—, —CH=CF— or —CF=CF—, particularly preferably, independently of one another, a single bond, —CF$_2$O—, —OCF$_2$—, —CH$_2$O—, —OCH$_2$—, —CF$_2$CF$_2$—, —CH=CH—, —CF=CH—, —CH=CF— or —CF=CF—. $Z^1$ and $Z^2$ are very particularly preferably, independently of one another, a single bond, —CF$_2$O—, —OCF$_2$—, —CH$_2$O—, —OCH$_2$— or —CF=CF—, in particular a single bond.

The parameters m and n in the sum m+n preferably have a value of 0, 1, 2 or 3, particularly 0, 1 or 2. For m+n=0, it is preferred for at least one group from $L^1$ and $L^2$, particularly preferably both groups, to denote F. In addition, for m+n=0, $R^1$ and $R^2$ preferably do not denote hydrogen.

$R^1$ and $R^2$ preferably each, independently of one another, denote an alkanyl radical, alkoxy radical or alkenyl radical having 1 to 7 or 2 to 7 carbon atoms respectively, where each of these radicals is unsubstituted or mono- or polysubstituted by halogen, or fluorine or hydrogen, particularly preferably an alkanyl radical, alkoxy radical or alkenyl radical as described.

$R^1$ and $R^2$ in the general formula I are particularly preferably, independently of one another, an alkanyl radical, alkoxy radical or alkenyl radical having 1 to 7 or 2 to 7 C atoms respectively, where each of these radicals is preferably unsubstituted or mono- or polysubstituted by halogen. In the case where m=0, $R^1$ preferably denotes an alkyl or alkoxy group, H or F, particularly preferably an alkyl group having 1-6 C atoms.

If $R^1$ and $R^2$ in the formula I each, independently of one another, represent an alkanyl radical and/or an alkoxy radical (alkyloxy radical) having 1 to 15 C atoms, these are straight-chain or branched. Each of these radicals is preferably straight-chain, has 1, 2, 3, 4, 5, 6 or 7 C atoms and is accordingly preferably methyl, ethyl, propyl, butyl, pentyl, hexyl, heptyl, methoxy, ethoxy, propoxy, butoxy, pentoxy, hexyloxy or heptyloxy.

$R^1$ and $R^2$ in the formula I may each, independently of one another, also be an oxaalkyl radical, i.e. an alkanyl radical in which at least one of the non-terminal $CH_2$ groups has been replaced by —O—, preferably straight-chain 2-oxapropyl (=methoxymethyl), 2-(=ethoxymethyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl. In a corresponding manner, $R^1$ and $R^2$ in the formula I may also, independently of one another, be thioalkanyl or sulfonealkanyl radicals, i.e. alkanyl radicals in which one $CH_2$ group has been replaced by —S— or —$SO_2$—.

$R^1$ and $R^2$ in the formula I may furthermore each, independently of one another, be an alkenyl radical having 2 to 15 C atoms which is straight-chain or branched and has at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl. If the two C atoms of the C—C double bond are substituted, the alkenyl radical can be in the form of the E and/or Z isomer (trans/cis). In general, the respective E isomers are preferred.

In the same way as for an alkanyl radical, at least one of the $CH_2$ groups in an alkenyl radical may also have been replaced by oxygen, sulfur or —$SO_2$—. In the case of replacement by —O—, an alkenyloxy radical (having a terminal oxygen) or an oxaalkenyl radical (having a non-terminal oxygen) is then present.

$R^1$ and $R^2$ in the formula I may, independently of one another, also be an alkynyl radical having 2 to 15 C atoms which is straight-chain or branched and has at least one C—C triple bond.

$R^1$ and $R^2$ in the formula I may each, independently of one another, be an alkanyl radical having 1 to 15 C atoms in which one $CH_2$ group has been replaced by —O— and one has been replaced by —CO—, where these are preferably adjacent. This thus contains an acyloxy group —CO—O— or an oxycarbonyl group —O—CO—. This radical is preferably straight-chain and has 2 to 6 C atoms. The following of these radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl. Furthermore, an alkanyl radical can also have an —O—CO—O— unit. Replacement of a $CH_2$ group by only one —CO— group (carbonyl function) is also possible.

$R^1$ and $R^2$ in the formula I may each, independently of one another, be an alkenyl radical having 2 to 15 C atoms in which a $CH_2$ group, preferably in the vicinity of an unsubstituted or substituted —C=C— unit, has been replaced by —CO—, —CO—O—, —O—CO— or —O—CO—O—, where this radical may be straight-chain or branched. The radical is preferably straight-chain and has 4 to 13 C atoms. Particular preference is given here to acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl and 8-methacryloyloxyoctyl. Correspondingly, a $CH_2$ group in the vicinity of a substituted unit in —C≡C— unit in an alkynyl radical may also be replaced by —CO—, —CO—O—, —O—CO— or —O—CO—O—.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is monosubstituted by —CN, where these are preferably straight-chain. The substitution by —CN is possible in any desired position.

$R^1$ and $R^2$ in the formula I may each, independently of one another, be an alkanyl radical in which two or more $CH_2$ groups have been replaced by —O— and/or —CO—O—, where this may be straight-chain or branched. It is preferably branched and has 3 to 12 C atoms.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is mono- or polysubstituted by F, Cl and/or Br, where these radicals are preferably straight-chain and halogen is preferably —F and/or —Cl. In the case of polysubstitution, halogen is preferably —F. The resultant radicals also include perfluorinated radicals, such as —$CF_3$. In the case of monosubstitution, the fluorine or chlorine substituent can be in any desired position, but is preferably in the ω-position.

$R^1$ and $R^2$ in the formula I may also each, independently of one another, be —F, —Cl, —Br, —CN, —SCN, —NCS or —$SF_5$. In this case, the dielectric anisotropy increases towards more positive values. For very particularly strongly negative dielectric anisotropies, these substituents should not be selected. However, they are preferred for high Δε.

In connection with the present invention, halogen denotes fluorine, chlorine, bromine or iodine, in particular fluorine or chlorine.

In connection with the present invention, the term "alkyl"—unless defined otherwise elsewhere in this description or in the claims—denotes a straight-chain or branched aliphatic hydrocarbon radical having 1 to 15 (i.e. 1, 2, 3, 4, 5, 6, 7, 8, 9, 10, 11, 12, 13, 14 or 15) carbon atoms. If this alkyl radical is a saturated radical, it is also referred to as "alkanyl".

Particular preference is given to compounds of the formula I according to the invention selected from the sub-formulae IA to IF:

IA

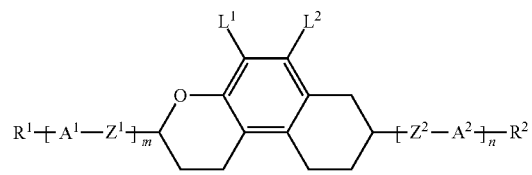

-continued

IB
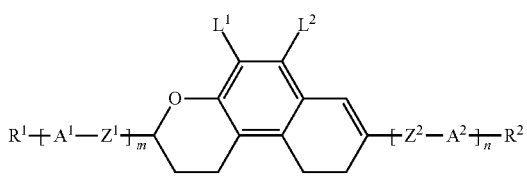

IC
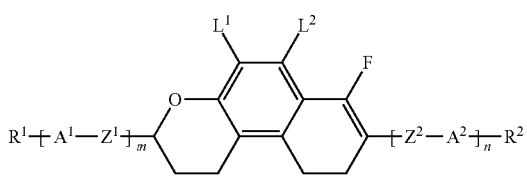

ID
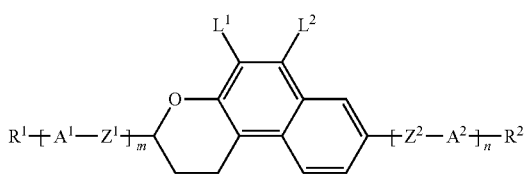

IE
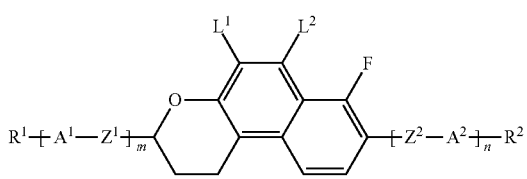

IF
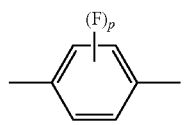

in which $R^1$, $R^2$, $A^1$, $A^2$, $L^1$, $L^2$, m, n, $Z^1$ and $Z^2$ have the same and the same preferred meanings as defined above for formula I.

If $A^1$ and $A^2$ or $Z^1$ and $Z^2$ occur twice in the formulae IA to IF, they can in each case have identical or different meanings.

Very particularly preferred compounds of the formula IA for which n+m=0 are the following:

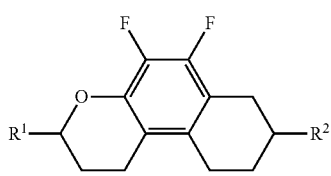

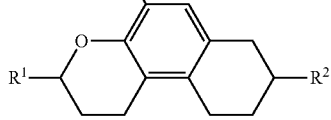

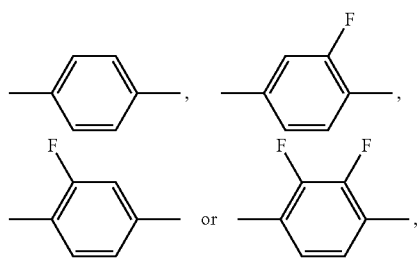

in which
$R^1$, $R^2$ preferably denote an alkyl or alkoxy radical having up to 8 C atoms.

Above and below, the moiety

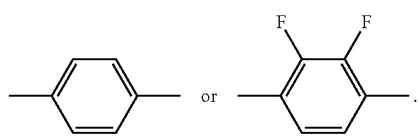

in which p denotes 0, 1, 2, 3 or 4, in the sub-formulae in each case, independently of one another, preferably denotes a moiety of the formula

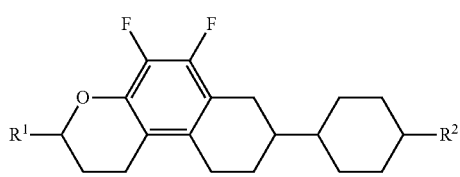

and particularly preferably

If the index p in the formulae above and below occurs more than once, it can on each occurrence in each case have identical or different meanings, preferably 0, 1 or 2.

Very particularly preferred compounds of the formula IA for which n+m=1 are the following:

-continued
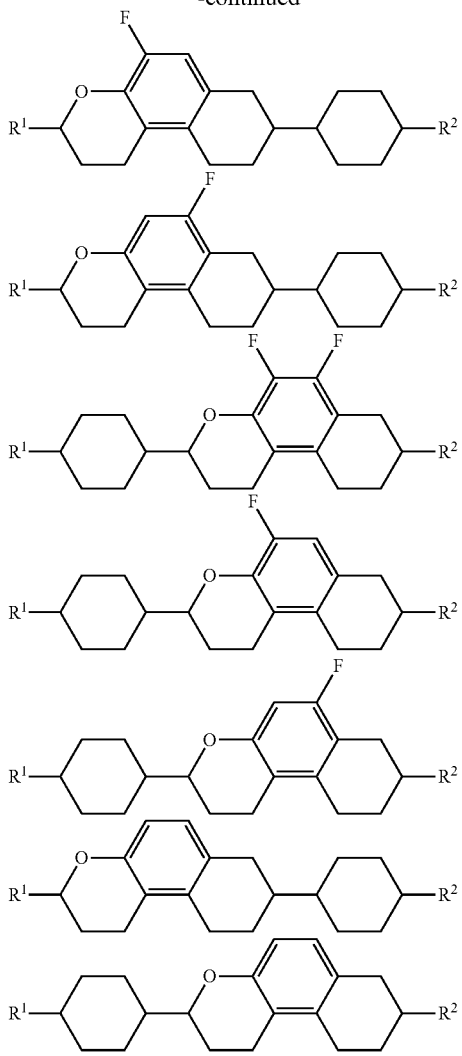
in which
R$^1$ and R$^2$ have the same meanings as defined above.
Very particularly preferred compounds of the formula IA for which n+m=2 are the following:
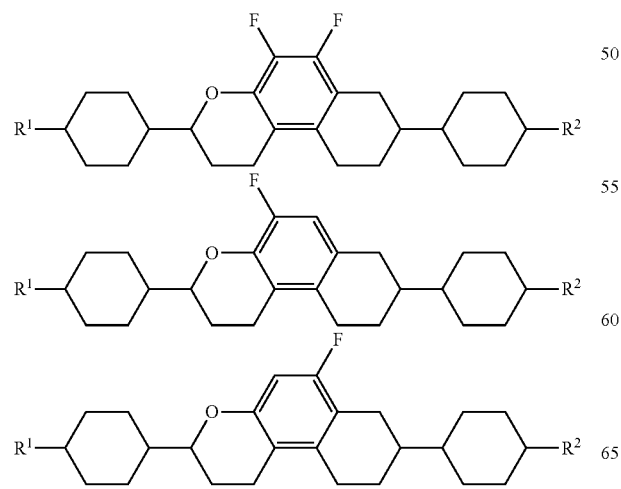
-continued
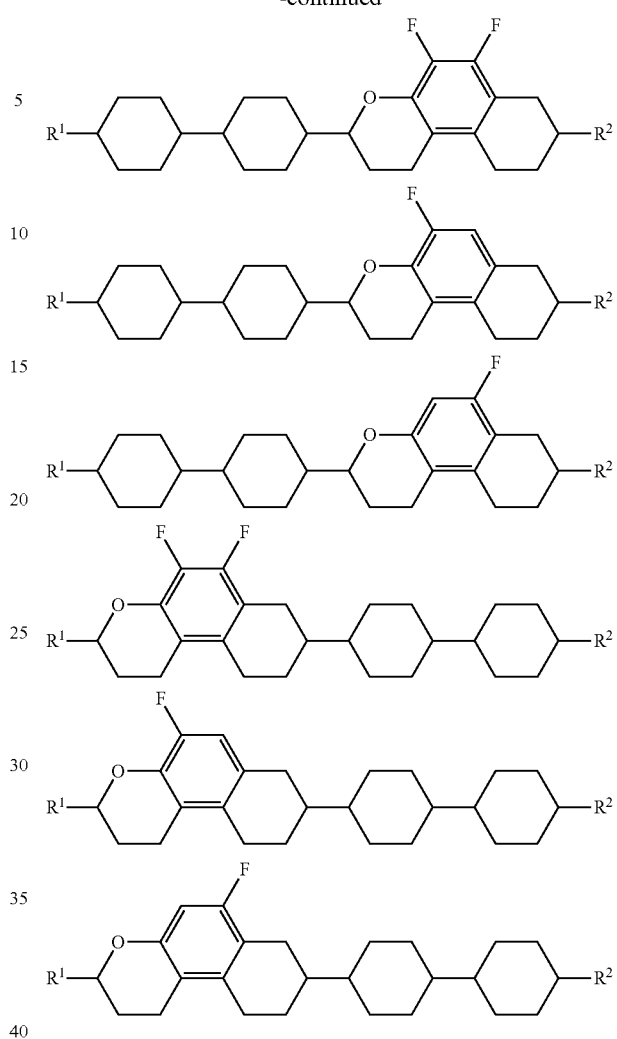
in which
R$^1$ and R$^2$ have the same meanings as defined above.
Very particularly preferred compounds of the formula IB for which n+m=0 are the following:
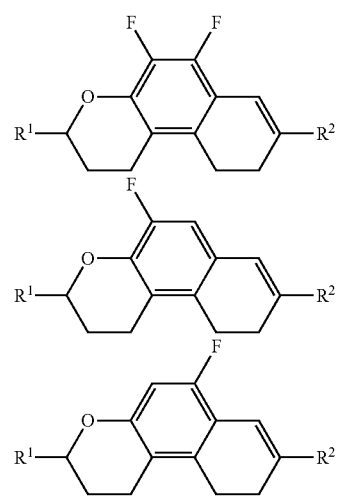

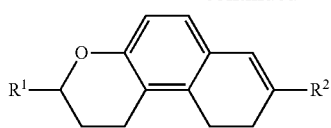
in which
R¹ and R² preferably denote an alkyl or alkoxy radical having up to 8 C atoms.
Very particularly preferred compounds of the formula IB for which n+m=1 are the following:
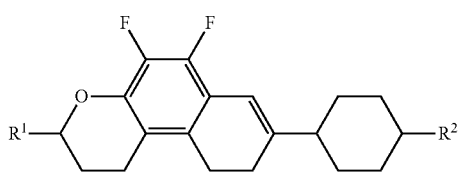
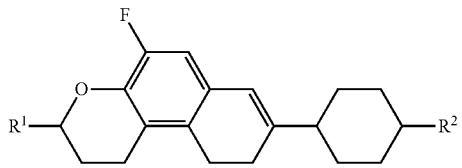
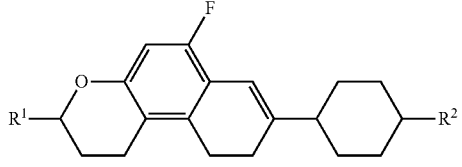
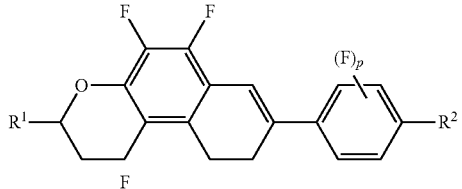
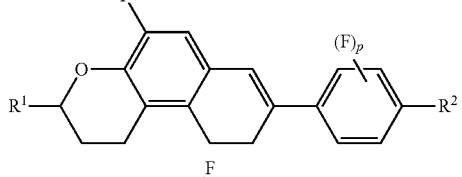
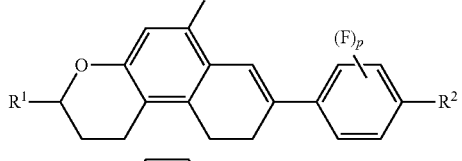
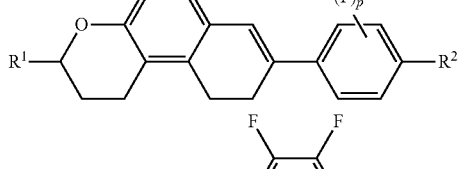
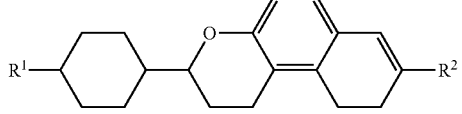
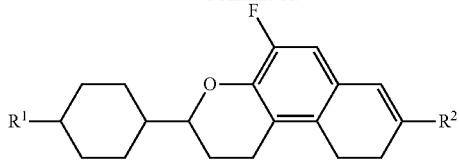
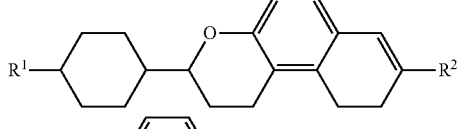
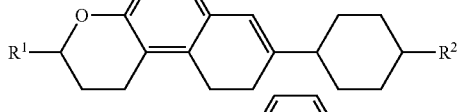
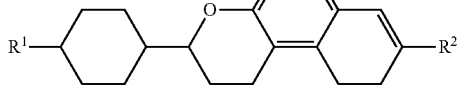
in which
R¹, R² and p have the same meanings as defined above.
Very particularly preferred compounds of the formula IB for which n+m=2 are the following:
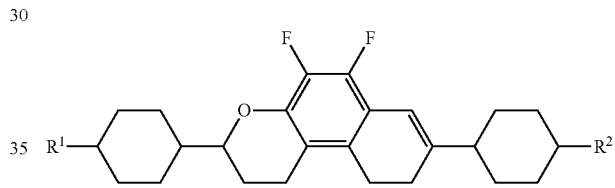
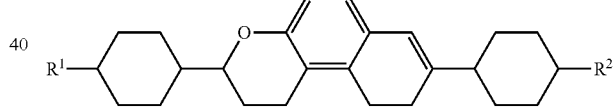
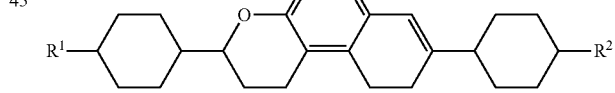
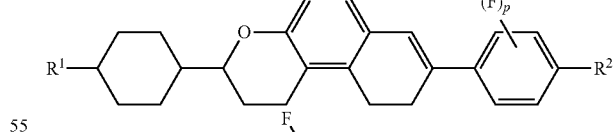
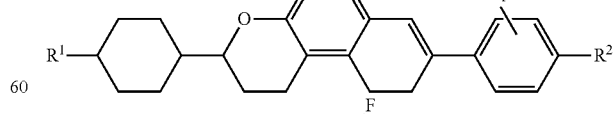
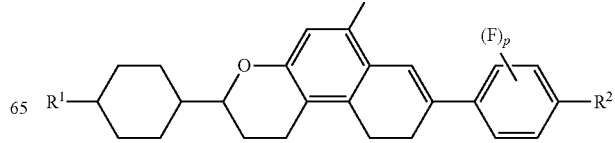

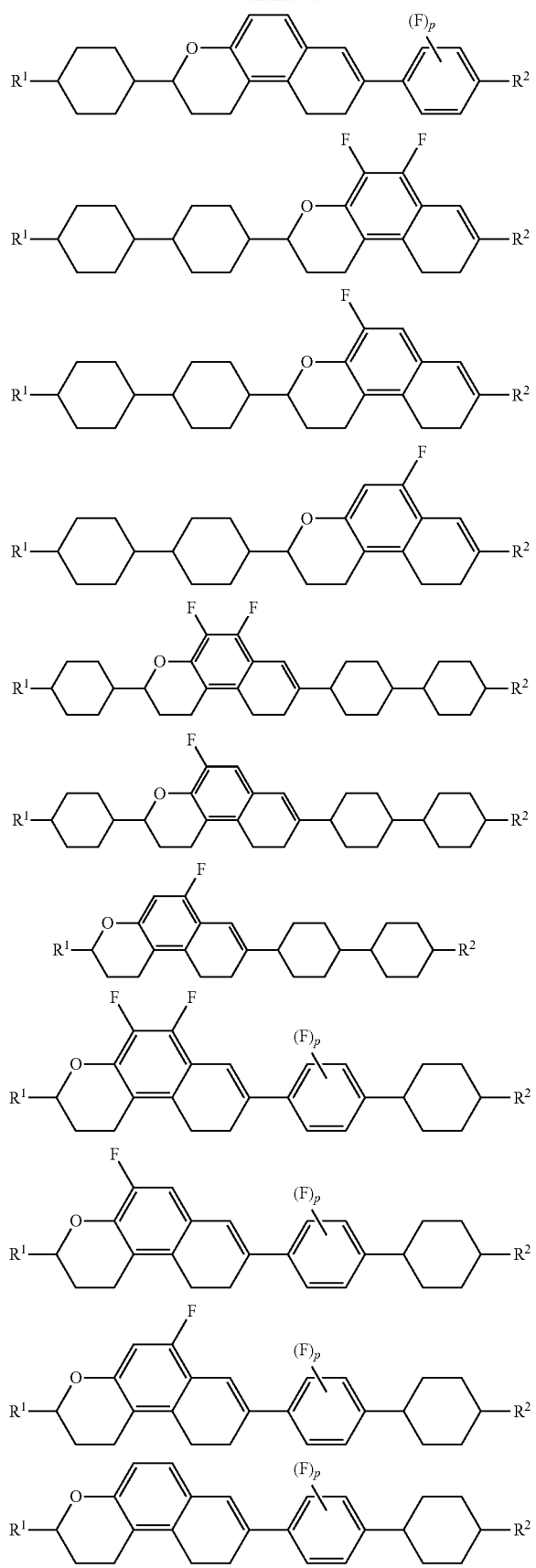
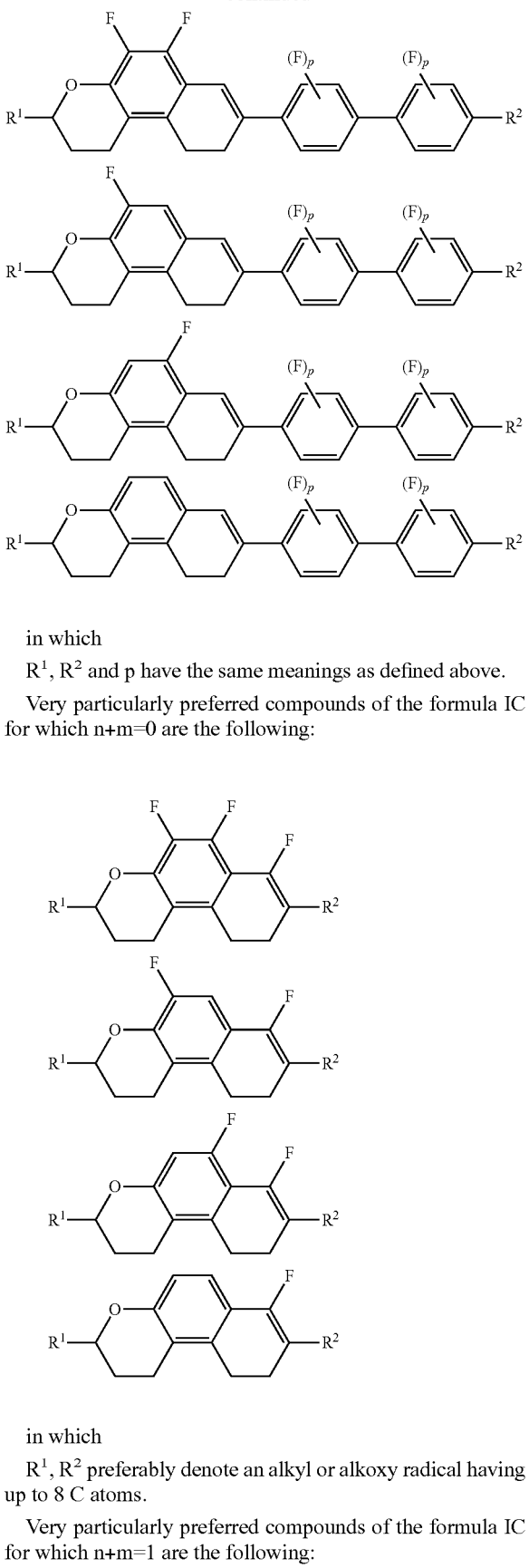
in which
R[1], R[2] and p have the same meanings as defined above.
Very particularly preferred compounds of the formula IC for which n+m=0 are the following:
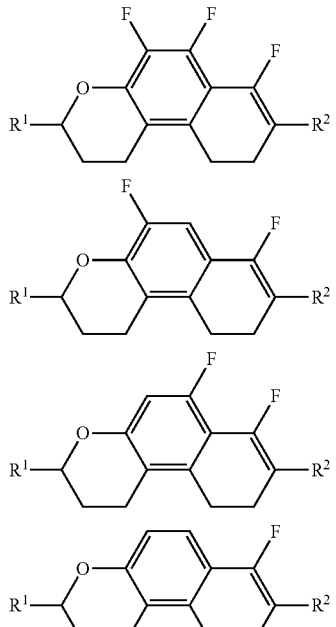
in which
R[1], R[2] preferably denote an alkyl or alkoxy radical having up to 8 C atoms.
Very particularly preferred compounds of the formula IC for which n+m=1 are the following:

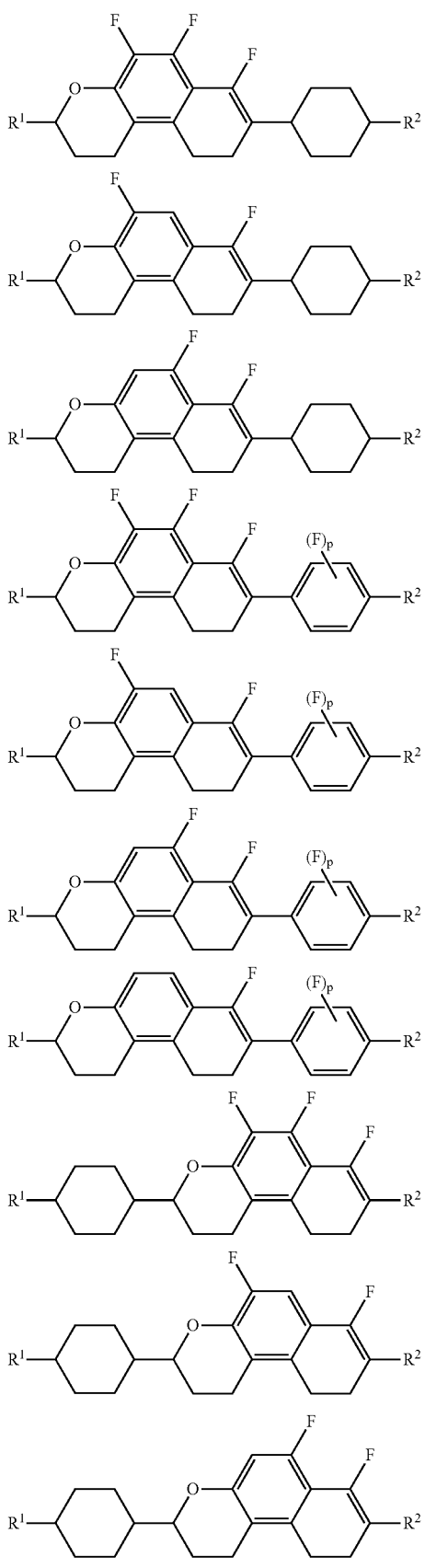
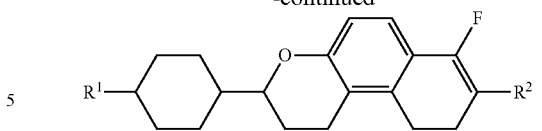
in which
R$^1$, R$^2$ and p have the same meanings as defined above.
Very particularly preferred compounds of the formula IC for which n+m=2 are the following:
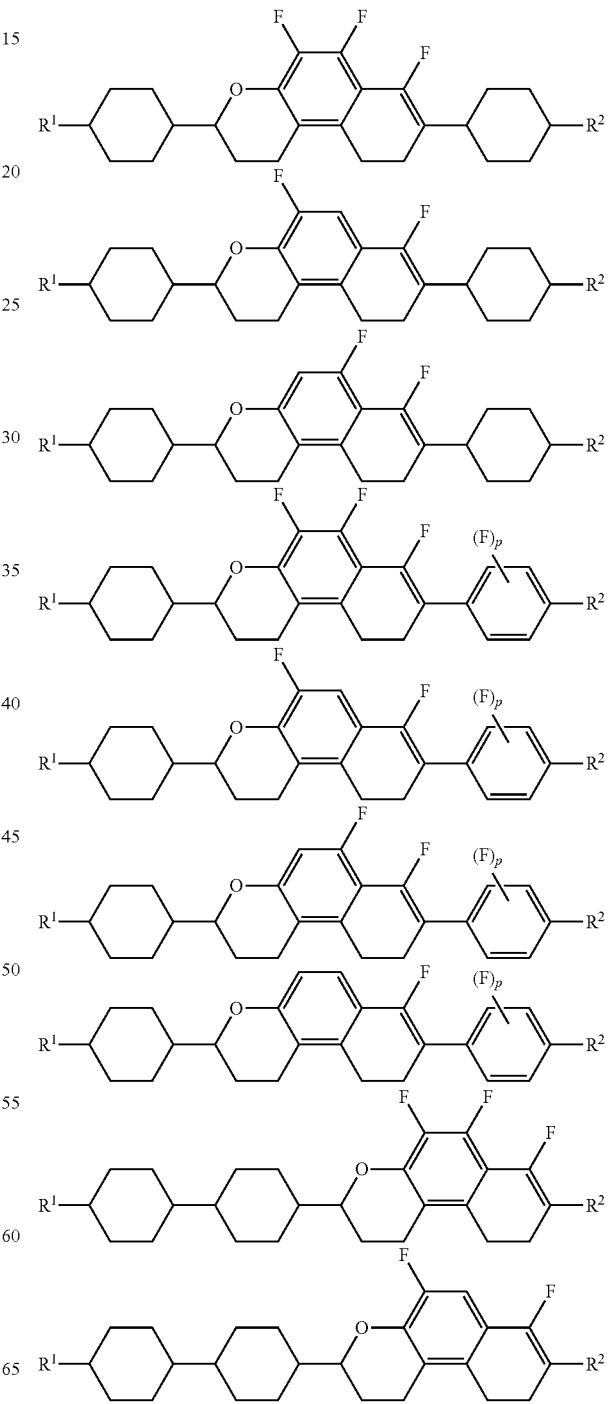

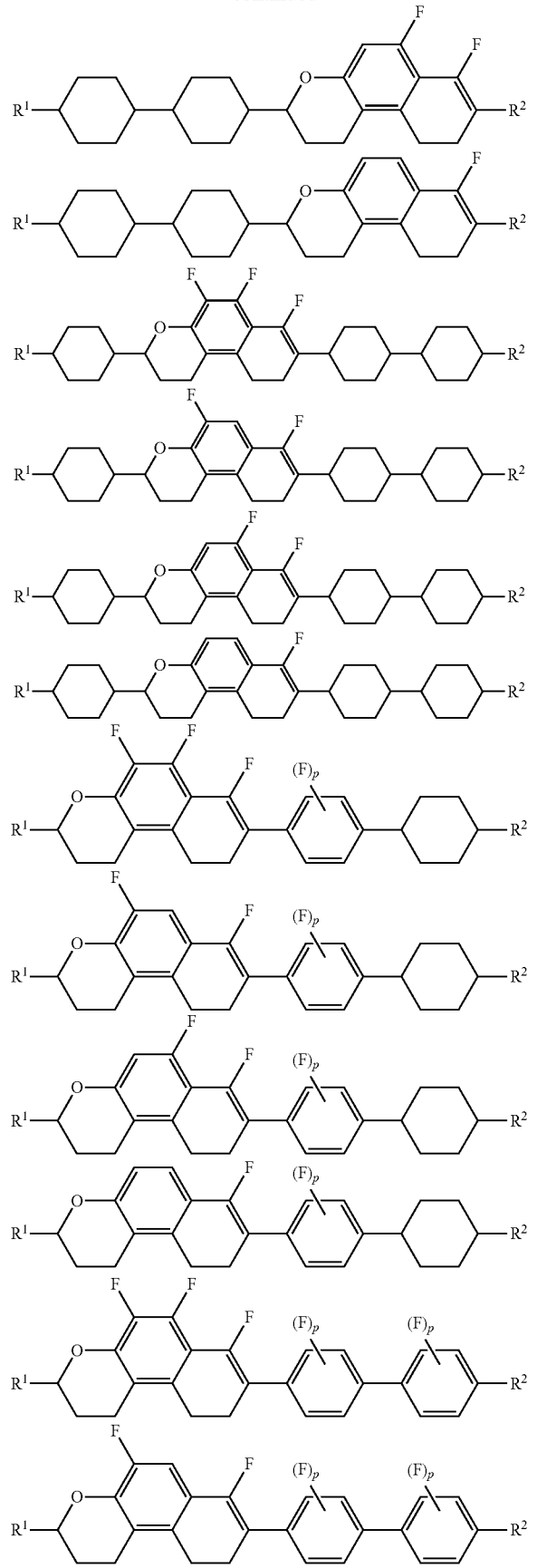
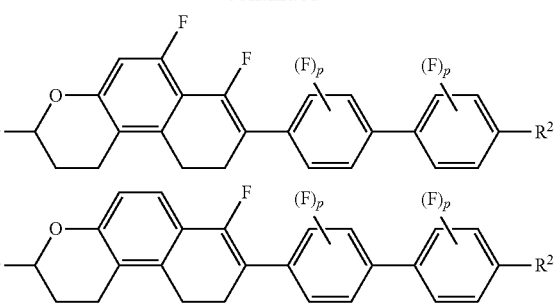
in which
R¹, R² and p have the same meanings as defined above.
Very particularly preferred compounds of the formula ID for which n+m=0 are the following:
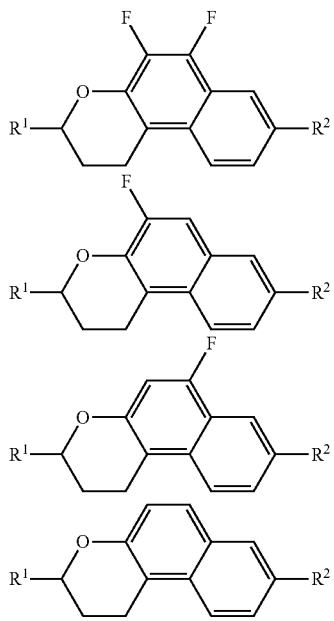
in which
R¹, R² preferably denote an alkyl or alkoxy radical having up to 8 C atoms.
Very particularly preferred compounds of the formula ID for which n+m=1 are the following:
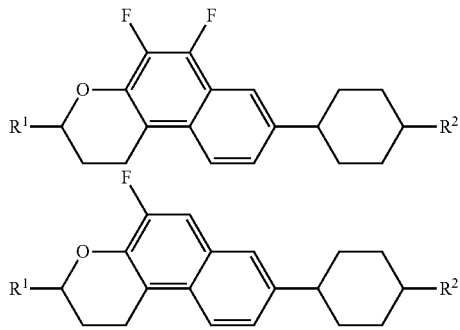

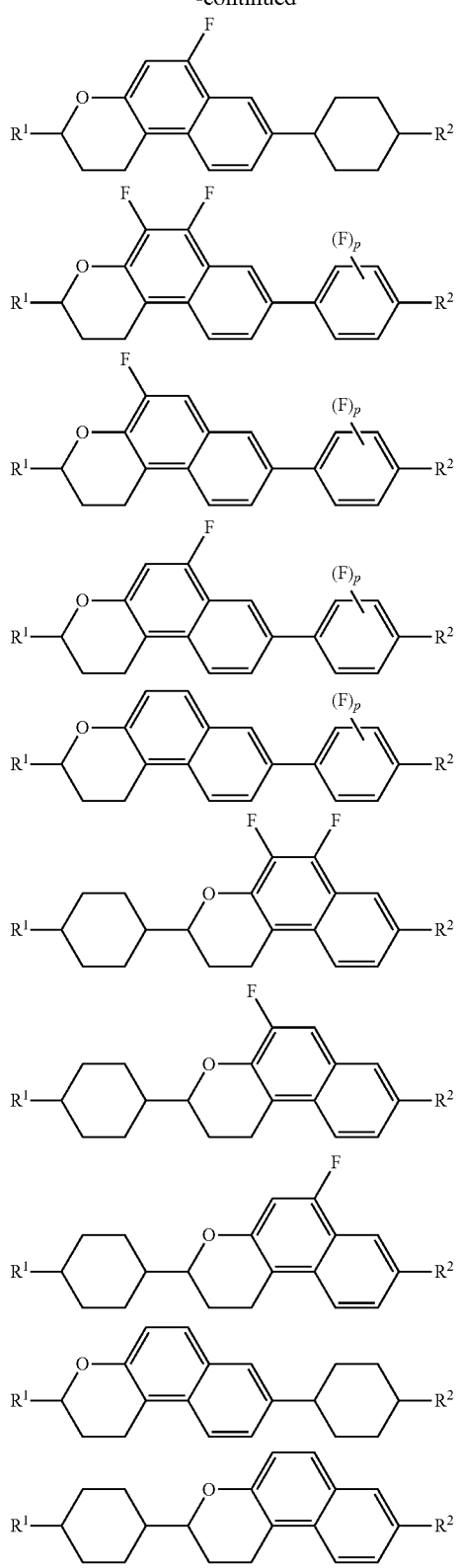
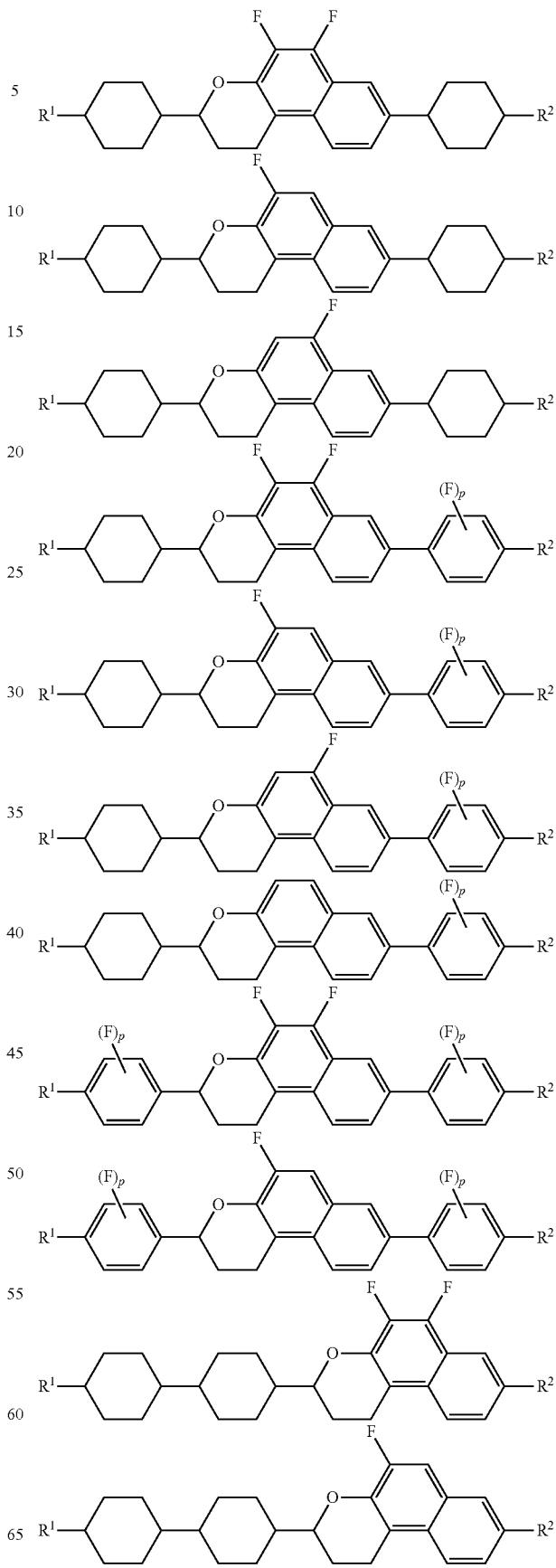
in which
R[1], R[2] and p have the same meanings as defined above.
Very particularly preferred compounds of he formula ID for which n+m=2 are the following:

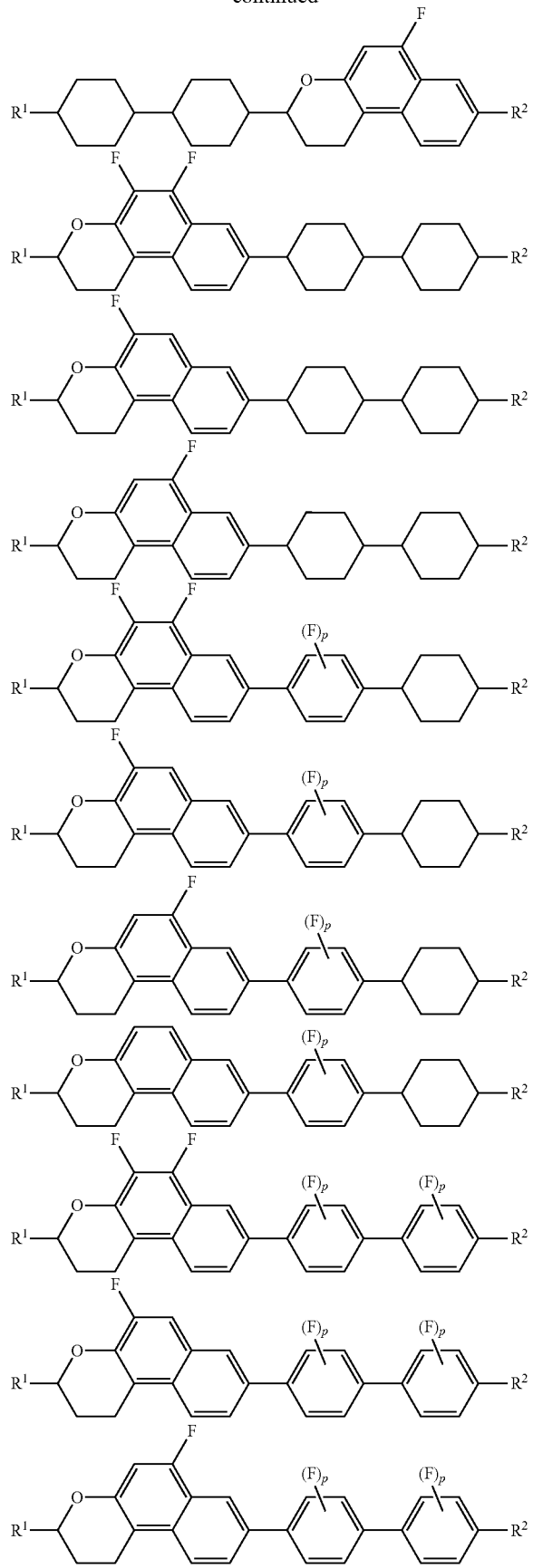
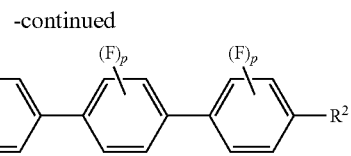
in which
R¹, R² and p have the same meanings as defined above.
Very particularly preferred compounds of the formula IE for which n+m=0 are the following:
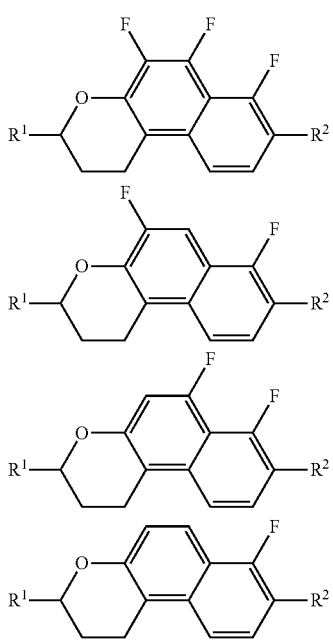
in which
R¹, R² preferably denote an alkyl or alkoxy radical having up to 8 C atoms.
Very particularly preferred compounds of the formula IE for which n+m=1 are the following:
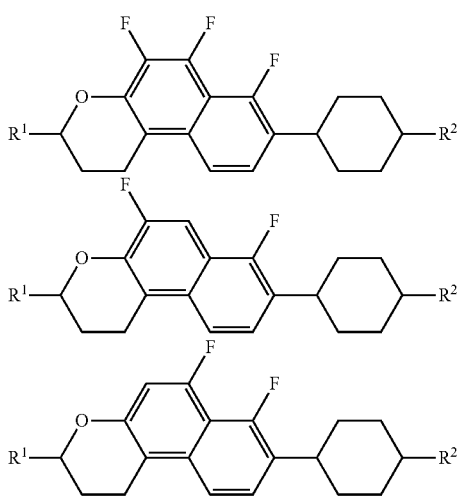

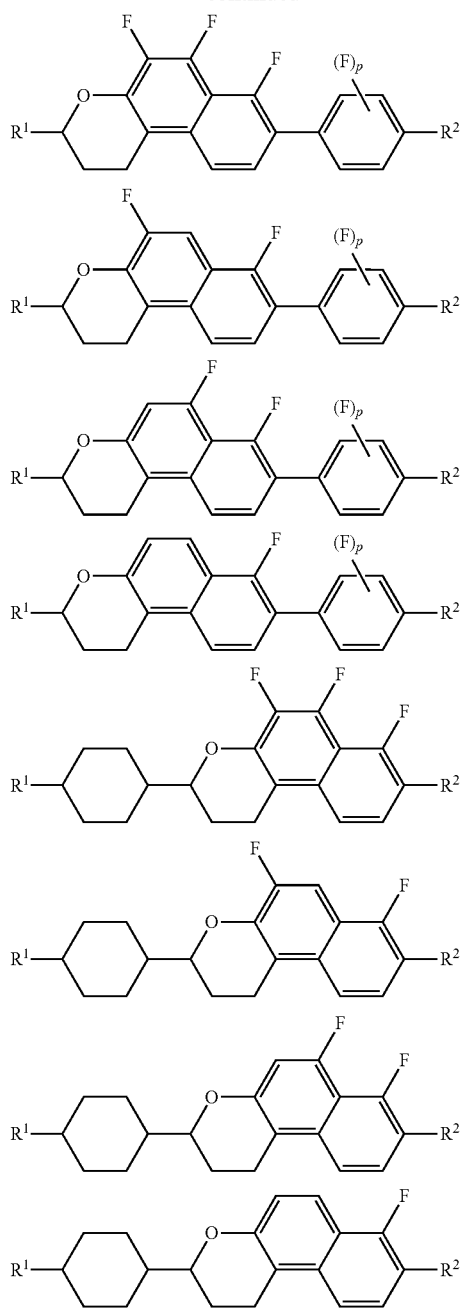
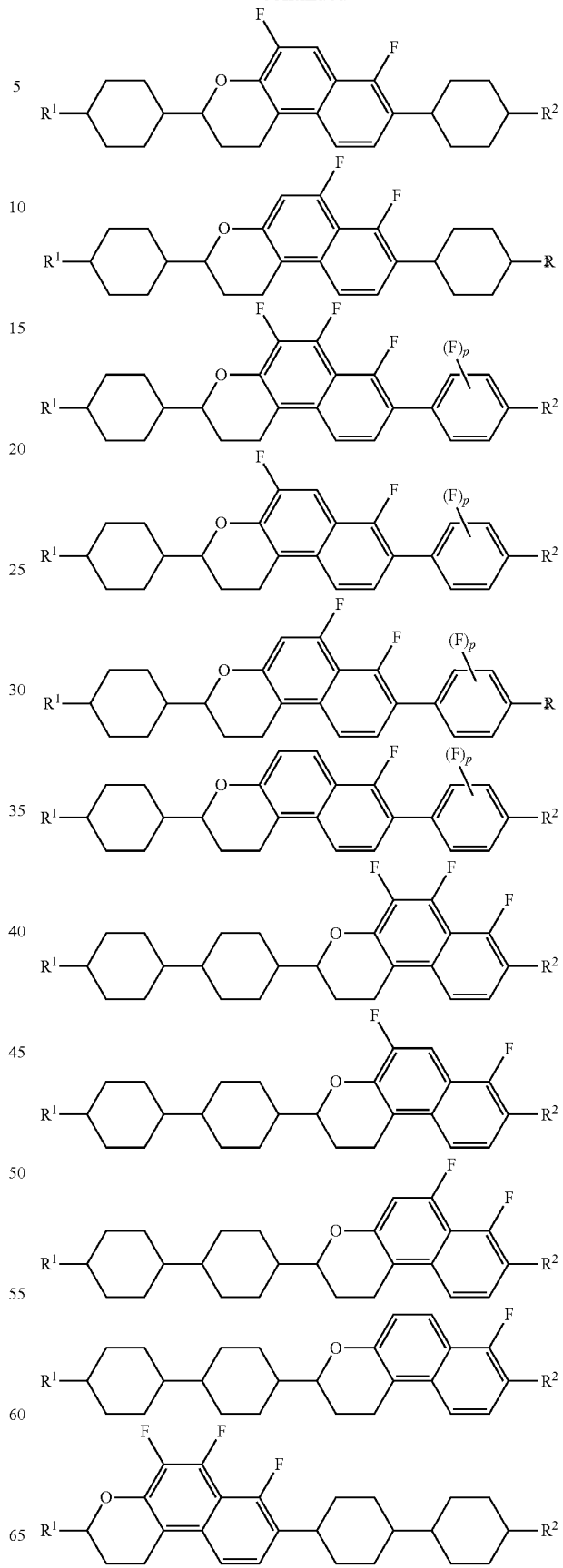
in which
R[1], R[2] and p have the same meanings as defined above.
Very particularly preferred compounds of the formula IE for which n+m=2 are the following:
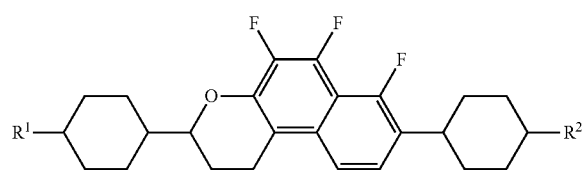

-continued

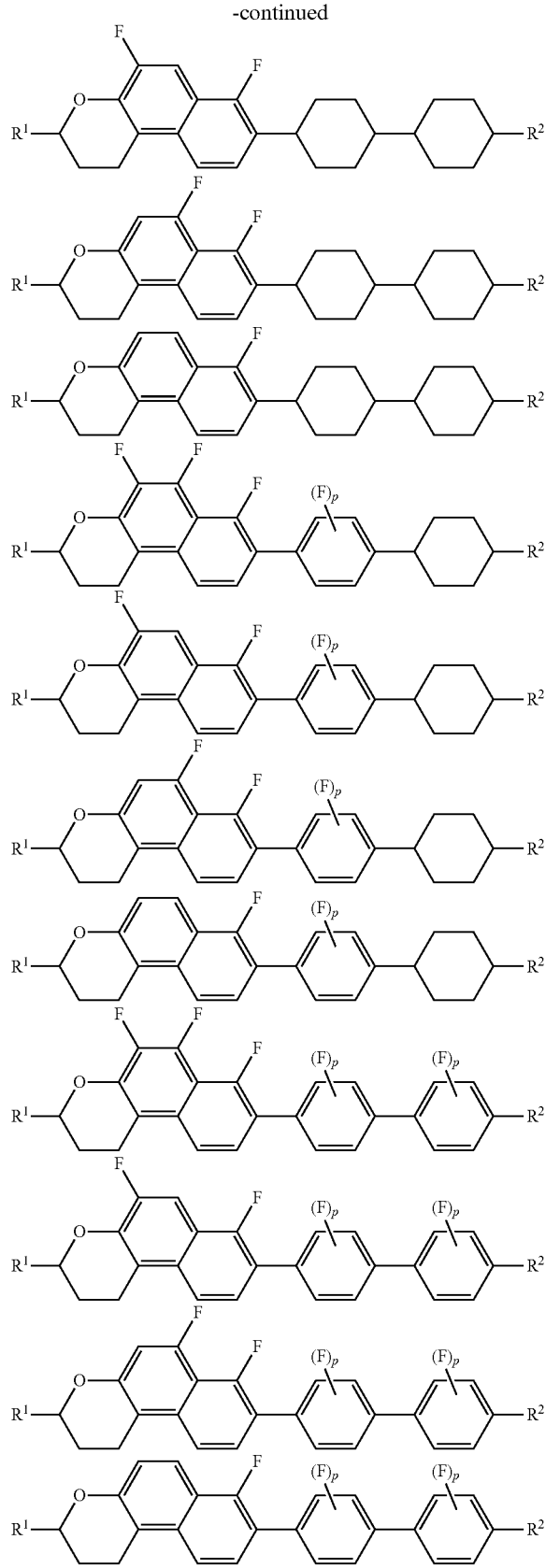

in which
R[1], R[2] and p have the same meanings as defined above.

Very particularly preferred compounds of the formula IF for which n+m=0 are the following:

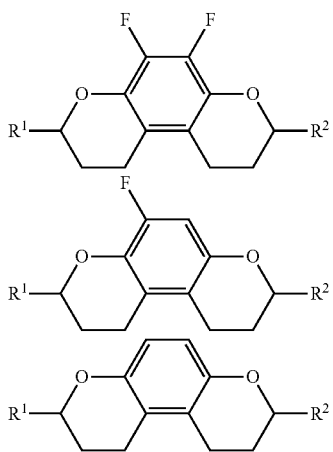

in which
R[1], R[2] preferably denote an alkyl or alkoxy radical having up to 8 C atoms.

Very particularly preferred compounds of the formula IF for which n+m=1 are the following:

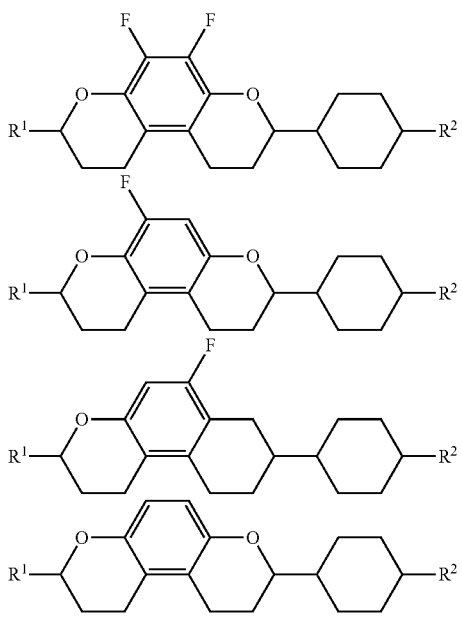

in which
R[1] and R[2] have the same meanings as defined above.

Very particularly preferred compounds of the formula IF for which n+m=2 are the following:

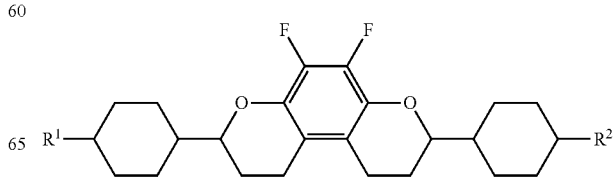

-continued

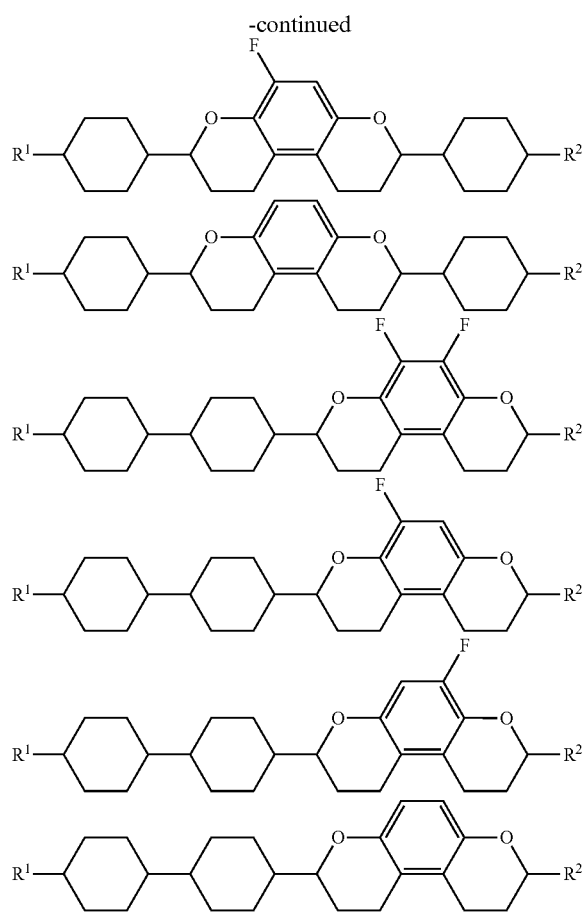

in which
R$^1$ and R$^2$ have the same meanings as defined above.

If radicals or substituents of the compounds according to the invention or the compounds according to the invention themselves are in the form of optically active or stereoisomeric radicals, substituents or compounds since they have, for example, a centre of asymmetry, these are likewise encompassed by the present invention. It goes without saying here that the compounds of the general formula I according to the invention may exist in isomerically pure form, for example as pure enantiomers, diastereomers, E or Z isomers, trans or cis isomers, or as a mixture of a plurality of isomers in any desired ratio, for example as a racemate, E/Z isomer mixture or as a cis/trans isomer mixture.

The 1,4-substituted cyclohexyl ring of the formula

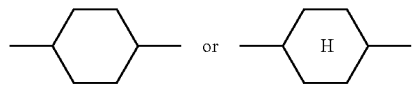

in the compounds according to the invention and in the other components of liquid-crystalline media preferably has the trans configuration, i.e. the two substituents are both in the equatorial position in the thermodynamically preferred chair conformation.

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula I.

The syntheses of various compounds of the general formula I according to the invention are described by way of example in the examples. The starting substances can be obtained by generally accessible literature procedures or are commercially available.

Particularly suitable synthetic routes to the compounds according to the invention are explained below with reference to Schemes I to XXX. The substituents R$^1$, R$^2$, A$^1$, A$^2$, Z$^1$, Z$^2$ and the indices m and n in the following schemes have at least the meanings as for formula I; R$^1$ and R$^2$ can optionally also be a derivatisable group selected from OTs (tosylate), OTf (triflate), OMes (mesylate), —B(OH)$_2$, —B(O-alkyl)$_2$ or —B<(O—C$_{2-10}$-alkylene-O). The substituents R$^{11}$ and R$^{22}$ likewise have the thus-expanded meaning of R$^1$/R$^2$.

The substituents A$^{22}$ and Z$^{22}$ are generally defined like the radicals A$^2$ and Z$^2$ respectively; the variables in the group —[Z$^{22}$-A$^{22}$]$_n$-R$^{22}$ are selected in such a way that the group together with the closest group between —[Z$^{22}$-A$^{22}$]$_n$-R$^{22}$ and the tricyclic radical corresponds overall to a radical of the formula —[Z$^2$-A$^2$]$_n$-R$^2$. Thus, for example, a group of the formula —CH═CH—[Z$^{22}$-A$^{22}$]$_n$-R$^{22}$ or also of the formula -Ph-[Z$^{22}$-A$^{22}$]$_n$-R$^{22}$ is intended formally to correspond to a radical of the formula —[Z$^2$-A$^2$]$_n$-R$^2$.

The compounds of the formula I are preferably synthesised starting from the compounds 2 (cf. Scheme I).

The compounds 2 are etherified using propargyl alcohols 3 (method A) [O. Mitsunobu, *Synthesis* 1981, 1] or propargyl bromides 4 (method B) to give the corresponding compounds 5. The propargyl aryl ethers 5 undergo a [3.3]-sigmatropic rearrangement on heating in N,N-diethylaniline to give the chromene derivatives 6 [H. Ishii, T. Ishikawa, S. Takeda, S. Ueki, M. Suzuki, *Chem. Pharm. Bull.* 1992, 40, 1148-1153]. Final hydrogenation then gives the target compounds 1, which correspond to the compounds of the formula I according to the invention or an intermediate for the preparation thereof.

Scheme I: Synthesis of the compounds 1 starting from the compounds 2.

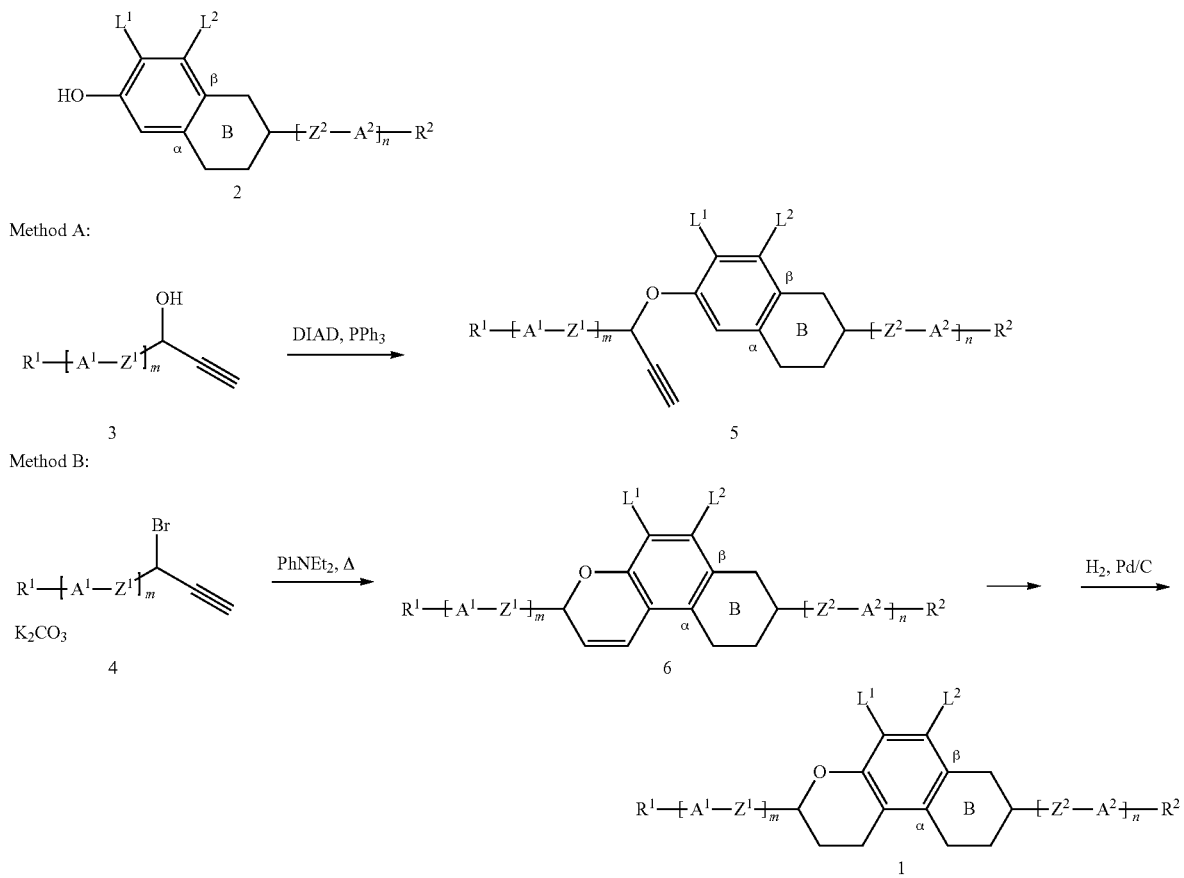

The synthesis can be adapted to the respectively desired compounds of the formula I through the choice of suitable starting materials 2 and 3 or 4. Suitable propargyl alcohols 3 or propargyl bromides 4 are either commercially available or can be synthesised by processes which have already been published.

The synthesis of the starting materials 2 is explained below with reference to some examples.

If ring B in the compounds of the formula I represents a cyclohexyl radical and if $L^1$ and $L^2$ are both equal to F, the synthesis of the compounds 2 (or here of the compounds 2a) starts with compound 7, the synthesis of which is disclosed in WO 2004/029015 A1 (cf. Scheme II).

Scheme II: Synthesis of the compounds 2 where B = cyclohexyl and $L^1$ = $L^2$ = F. (= 2a)

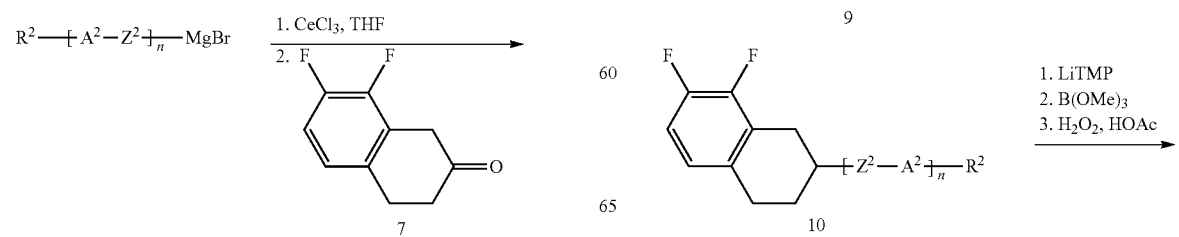

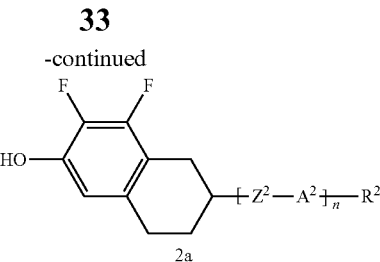

The functionalisation of the β-tetralone 7 starts with the cerium(III) chloride-promoted addition reaction of corresponding Grignard or organolithium compounds (cf. a) N. Takeda, T. Imamoto, *Org. Synth.* 1999, 76, 228-238. b) M. Scommoda et al. *J. Org. Chem.* 1996, 61, 4379-4390). Elimination by treatment with mesyl chloride and DBU (cf. M. Scommoda et al. above) gives the compounds 9 as the principal component in the isomer mixture. These are hydrogenated to give the corresponding tetrahydronaphthalenes 10, which are then converted into the tetrahydronaphthols 2a via the reaction sequence of ortho-metallation and hydrolysis and oxidation of the boronic acid ester formed in situ.

If ring B in the compounds of the formula I according to the invention is intended to represent a cyclohexenyl radical and if $L^1$ and $L^2$ are both intended to be equal to F, the latter reaction sequence is carried out with the intermediates 9 to give the corresponding starting materials 2 (=2c in Scheme VII).

If ring B in the compounds of the formula I according to the invention represents a cyclohexyl radical and if one of the substituents $L^1$ and/or $L^2$ is equal to H, the synthesis of the compounds 2 is carried out starting from the compounds 11. $L^1$ or $L^2$ in 11 is preferably H, the other substituent is F.

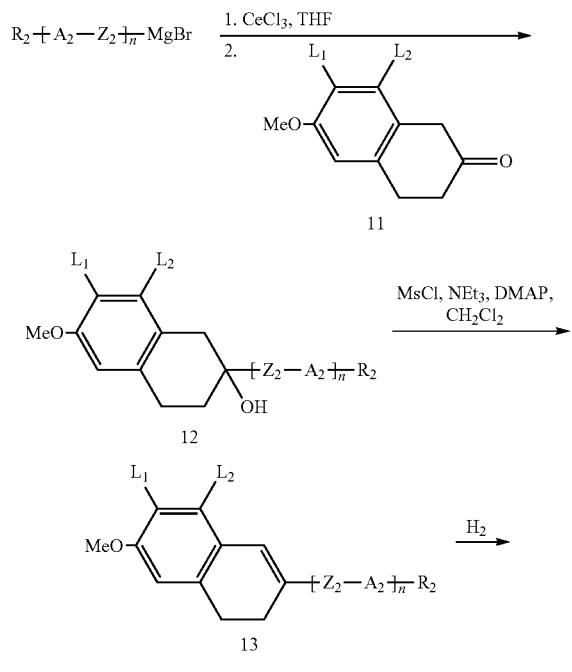

Scheme III: Synthesis of compound 2 where B = cyclohexyl and $L^1$ = H or F and $L^2$ = H or F (=2b).

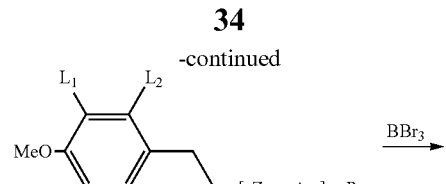

Analogously to Scheme II, the compounds 11 (6-methoxynaphthalen-2-ones) are to this end firstly functionalised by a cerium(III) chloride-promoted addition reaction of corresponding Grignard or organolithium compounds (cf. above). The elimination (cf. above) in turn gives the compounds 13 as the principal components in the isomer mixtures. Hydrogenation thereof gives 6-methoxy-1,2,3,4-tetrahydronaphthalenes 14. The methyl ether is finally cleaved using boron tribromide (cf. a) J. F. W. McOmie, D. E. West, *Org. Synth., Coll. Vol. V* 1973, 412; b) E. H. Vickery, L. F. Pahler, E. J. Eisenbraun, *J. Org. Chem.* 1979, 44, 4444-4446).

If ring B in the compounds 2 is intended to represent a cyclohexenyl radical and if $L^1$ and/or $L^2$ are intended to be equal to H, the methyl ether cleavage is carried out using the intermediates 13 to give the corresponding starting materials 2 (=2d in Scheme X).

For the synthesis sequence shown in Scheme III, the starting materials 7-fluoro-6-methoxy-3,4-dihydro-1H-naphthalen-2-one 11a (=11 where $L^1$=F, $L^2$=H) and 8-fluoro-6-methoxy-3,4-dihydro-1H-naphthalen-2-one 11b (=11 where $L^1$=H, $L^2$=F) are required in the cases in which only one of the substituents $L^1$ or $L^2$ is equal to F and the remaining substituent is equal to hydrogen (cf. Scheme IV). These starting materials are prepared from 3-fluoro-4-methoxyphenylacetic acid 15 and 2-fluoro-4-methoxyphenylacetic acid 16 respectively, likewise using the process used in WO 2004/029015 A1.

Scheme IV: Synthesis of 7-fluoro-6-methoxy-3,4-dihydro-1H-naphthalen-2-one 11a and 8-fluoro-6-methoxy-3,4-dihydro-1H-naphthalen-2-one 11b.

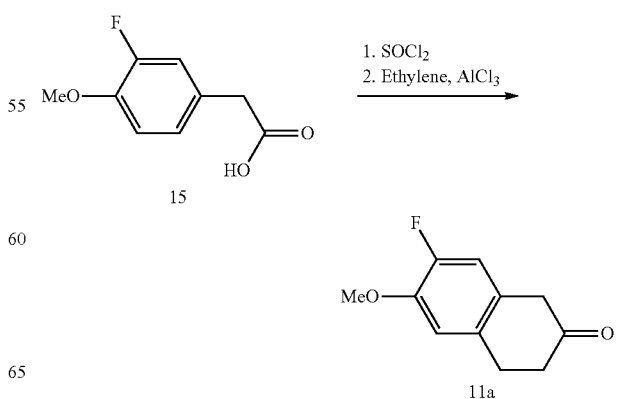

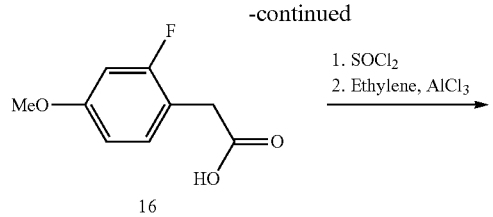

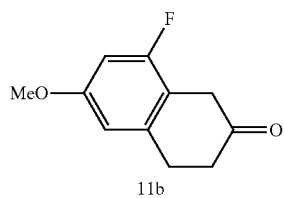

The synthesis of 3-fluoro-4-methoxyphenylacetic acid 15 starting from 2-fluoroanisole has been described by M. Kuchař et al. (*Collect. Czech. Chem. Commun.* 1990, 55, 296-306). 2-Fluoro-4-methoxyphenylacetic acid 16 is obtained from 2-fluoro-4-hydroxyphenylacetic acid [S.-I. Sugita, S. Toda, T. Yoshiyasu, T. Teraji, *Mol. Cryst. Liq. Cryst.* 1993, 237, 399-406; E. J. Corey, J. P. Dittami, *J. Am. Chem. Soc.* 1985, 107, 256-257; H. H. Wassermann, J. Wang, *J. Org. Chem.* 1998, 63, 5581-5586] by dimethylation and ester saponification.

Non-fluorinated synthesis building blocks 2 (where $L^1=L^2=H$) are obtained starting from 6-methoxy-3,4-dihydro-1H-naphthalen-2-one (11 where $L^1=L^2=H$). A synthesis of 6-methoxy-3,4-dihydro-1H-naphthalen-2-one (11 where $L^1=L^2=H$) has been described [S. N. Suryawanshi, S. N. Fuchs, *J. Org. Chem.* 1986, 51, 902-921].

A further, particularly preferred synthesis of the compounds 2 starts from compound 17 or compounds 18. The synthesis of 17 is carried out starting from 7 by generation of the enol ether and reaction thereof with trifluoroacetic anhydride. The compounds 18 are prepared analogously from compounds 11 (cf. Scheme V).

Scheme V: Synthesis of compound 17 and compounds 18.

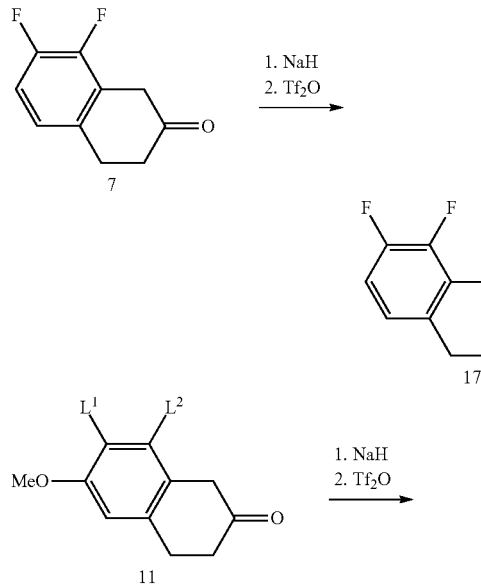

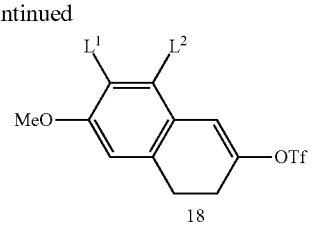

The enol triflates 17 and 18 can be functionalised in a variety of ways in transition metal-promoted cross-coupling reactions [*Metal-catalyzed Cross-coupling Reactions* (Eds.: A. de Meijre, F. Diederich), Wiley-VCH, Weinhelm, 2nd Edn. 2004] (cf. Scheme VI and Scheme IX). Cross couplings with arylboronic acids 19 (Suzuki couplings), alkenylboronic acids 21 and 23 [C. Sun, R. Bittman, *J. Org. Chem.* 2006, 71, 2200-2202 and A. Torrado, S. Lopez, R. Alvarez, A. R. de Lera, *Synthesis* 1995, 285-293], other boronic acids 25 [T. Oh-e, N. Miyaura, A. Suzuki, *J. Org. Chem.* 1993, 58, 2201-2208], Grignard reagents 26 [B. Scheiper, M. Bonnekessel, H. Krause, A. Fürstner, *J. Org. Chem.* 2004, 69, 3943-3949] and terminal alkynes 27 [Y. Zhao, K. Campbell, R. R. Tykwinski, *J. Org. Chem.* 2002, 67, 336-344] are particularly preferred methods for obtaining functionalised dihydronaphthalerie derivatives 9 (gen. formula) or 13 (gen. formula). In Scheme VI, some examples of cross-coupling reactions of the enol triflate 17 are shown.

Scheme VI: Examples of cross coupling with the enol triflate 17.

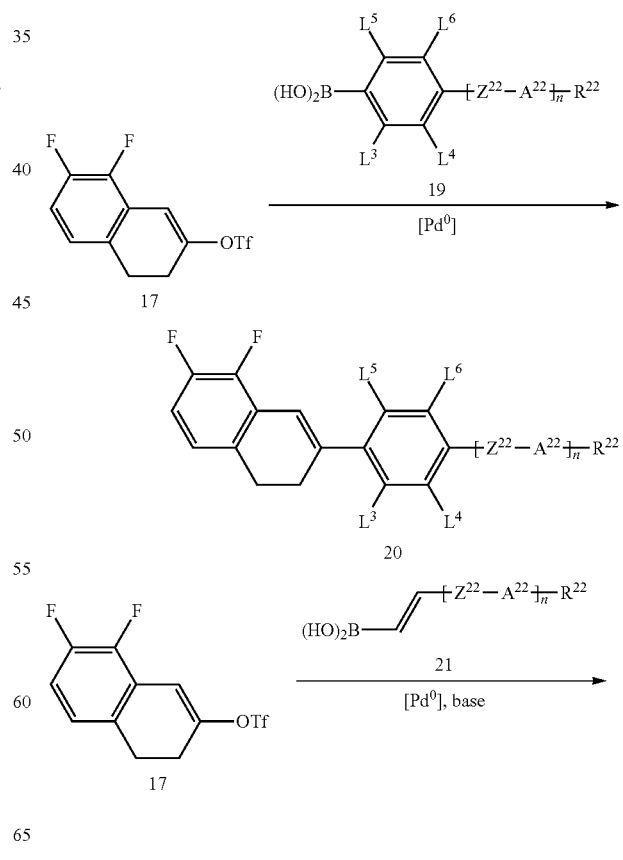

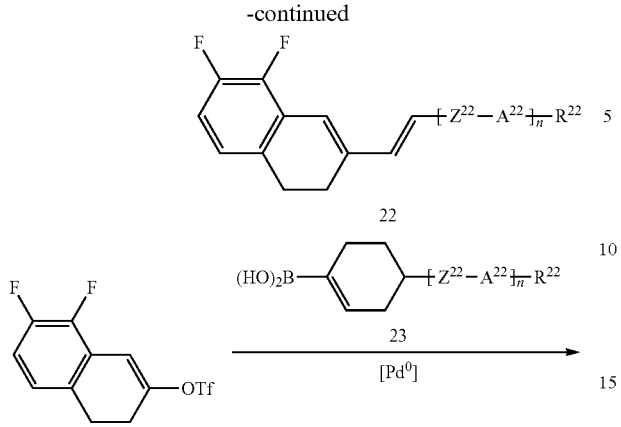
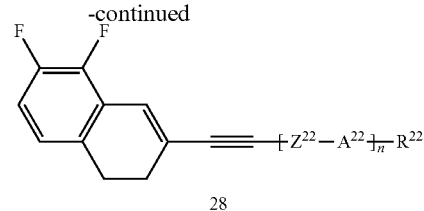

The products 9 (gen. formula, from Scheme III) from this functionalisation are converted into the desired compounds 2 as shown again in Scheme VII and Scheme VIII (cf. also Scheme II).

If B in the compounds 1 according to the invention is intended to be a cyclohexenyl radical, the compounds 9 are converted into the dihydronaphthols 2c via the reaction sequence of ortho-metallation and hydrolysis and oxidation of the boronic acid ester formed in situ (cf. Scheme VII).

Scheme VII: Synthesis of compounds 2 where B = cyclohexenyl and $L^1$ = $L^2$ = F (= 2c).

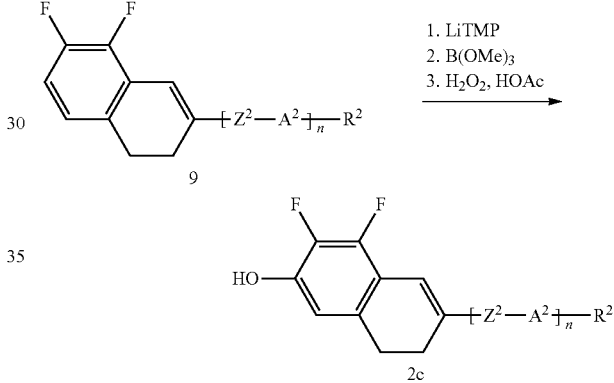
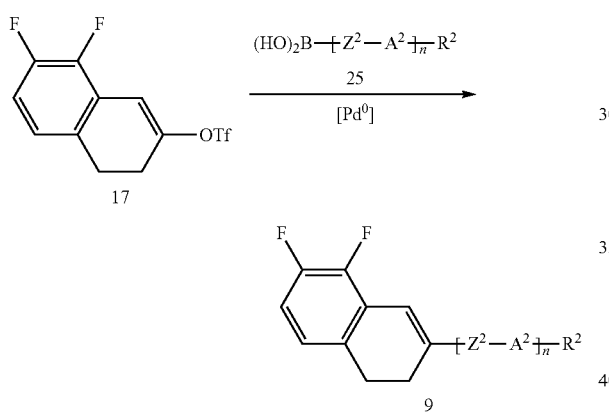

If B in the compounds 1 according to the invention is intended to be a cyclohexyl radical, the compounds 9 are firstly hydrogenated to give the compounds 10 and subsequently converted into the corresponding tetrahydronaphthols 2a as above (cf. Scheme VIII).

Scheme VIII: Synthesis of compounds 2 where B = cyclohexyl and $L^1$ = $L^2$ = F (= 2a).

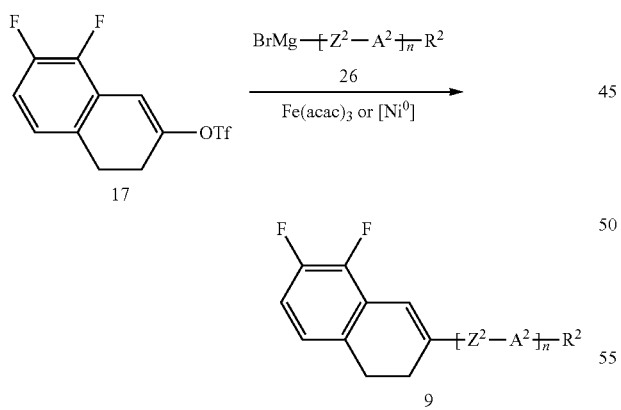
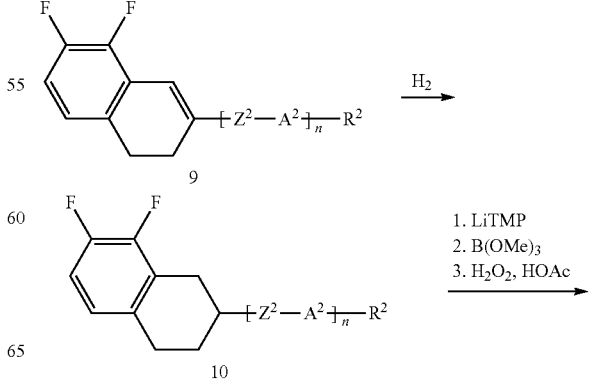
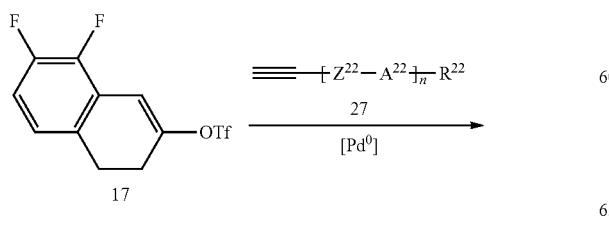

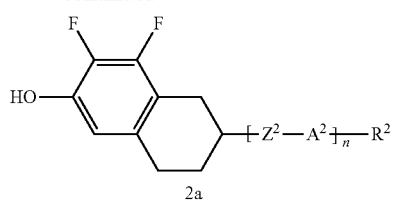
Scheme IX shows some examples of cross-coupling reactions of the enol triflates 18.
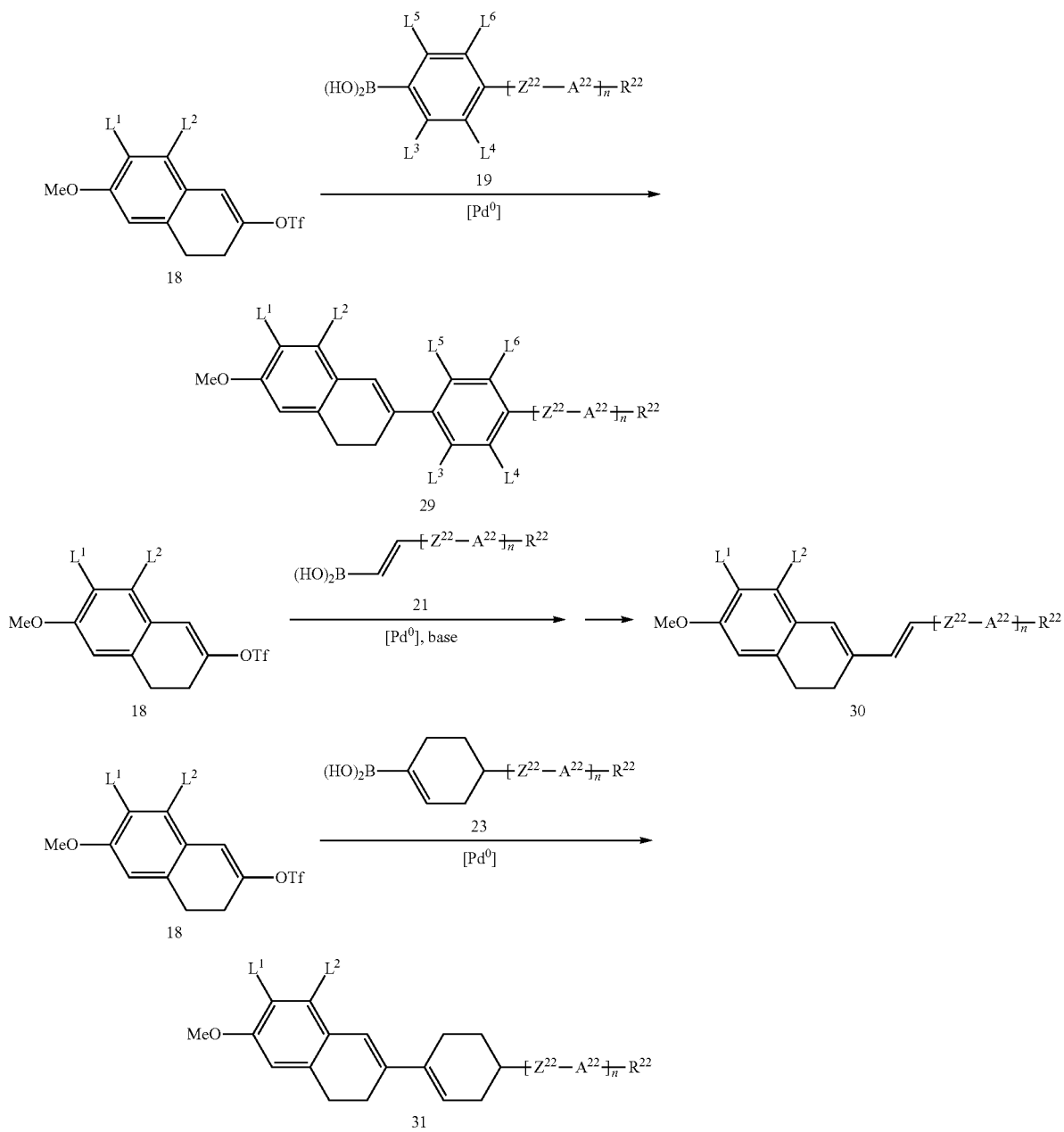

-continued

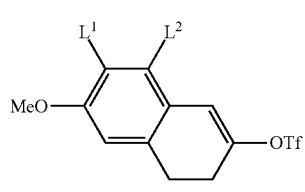 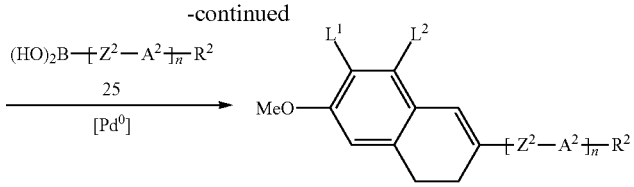

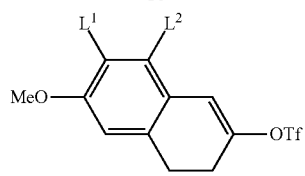 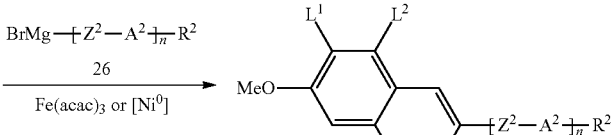

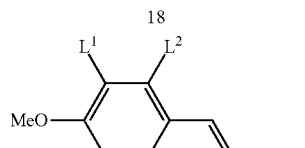 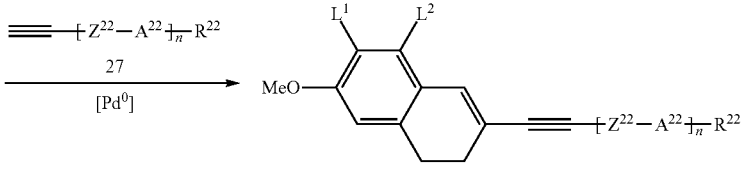

The products 13 (gen. formula) from this functionalisation are converted into the desired compounds 2 as shown again in Scheme X and Scheme XI (cf. also Scheme III).

If ring B in the compounds 2 is intended to represent a cyclohexenyl radical and if $L^1$ and/or $L^2$ are intended to be equal to H, a methyl ether cleavage is carried out using the intermediates 13 to give the corresponding starting materials 2d (cf. Scheme X).

Scheme X: Synthesis of compounds 7 where B = cyclohexenyl and $L^1$ = H or F and $L^2$ = H or F (= 2d)

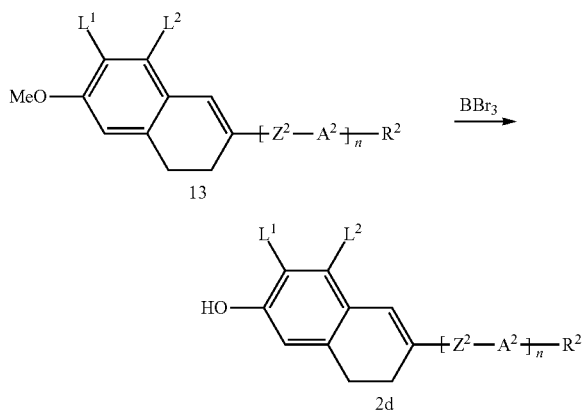

If ring B in the compounds 2 is intended to represent a cyclohexyl radical and if $L^1$ and/or $L^2$ are intended to be equal to H or F, a hydrogenation to give the compounds 14 is carried out before the methyl ether cleavage (cf. Scheme XI).

Scheme XI: Synthesis of compounds 2 where B = cyclohexyl and $L^1$ = H or F and $L^2$ = H or F (= 2b)

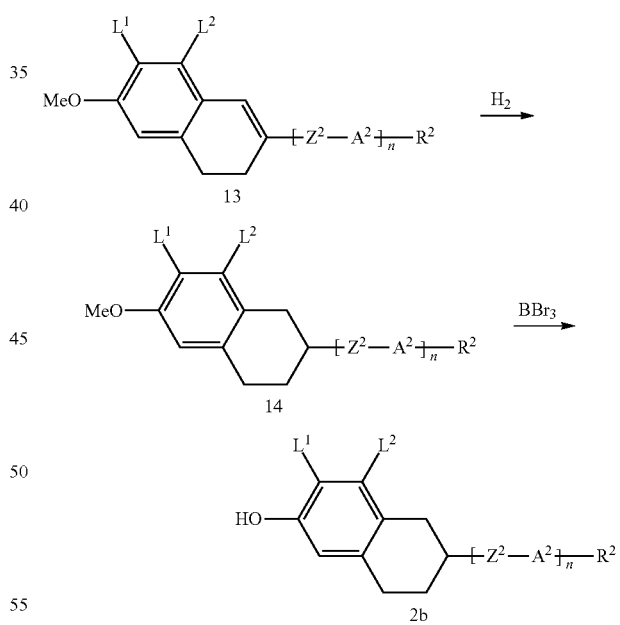

If ring B in the compounds of the formula I represents a phenyl radical ($L^3$=H) or a fluorinated phenyl radical ($L^3$=F) (cf. Scheme XII) and if $L^1$ and $L^2$ are both equal to F, the synthesis starts from the compounds 33 ($L^3$=H or F), the synthesis of which is disclosed in document WO 2004/029015 A1.

These intermediates 33 and the triflates 34 obtained therefrom (cf. Scheme XII) can be functionalised in a variety of ways (cf. Schemes XIII, XIV and XV).

Scheme XII: Synthesis of the triflates 34 from the compounds 33.

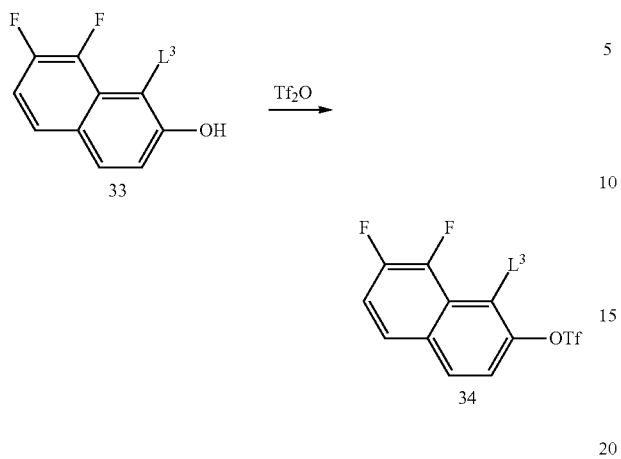

In the case where $R^2\text{-}(A^2\text{-}Z^2)_n$— is intended to represent an alkoxy radical, a simple etherification of 33 using alkyl iodides or bromides is carried out (cf. Scheme XIII).

Scheme XIII: Etherification of the compounds 33 to give the compounds 36.

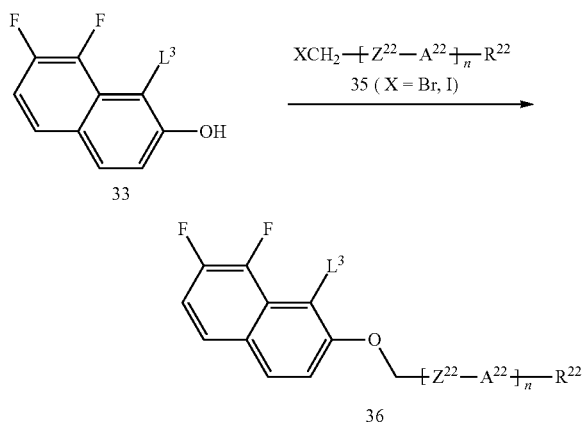

A further suitable method for obtaining the compounds 33 where $L^3$=H starting from (2,3-difluorophenyl)acetyl chloride is described in the literature [H. Juteau, Y. Gareau, H. Lachance, *Tetrahedron Lett.* 2005, 46, 4547-4549]. In this way, (2,3-difluorophenyl)acetyl chloride is reacted, for example, with trimethylsilylacetylene in the presence of aluminium(III) chloride to give the corresponding 2-trimethylsilylnaphthol. Removal of the silyl group (for example using potassium fluoride in DMF) then gives the compounds 33.

In the case where $R^2\text{-}(A^2\text{-}Z^2)_n$— is intended to represent an alkenyl radical, the triflates 34 are reacted with corresponding alkenylboronic acids in a palladium-catalysed cross coupling (cf. a) C. Sun, R. Bittmann, *J. Org. Chem.* 2006, 71, 2200-2202; b) A. Torrado, S. Lopez, R. Alvarez, A. R. de Lera, *Synthesis* 1995, 285-293). These alkenyl compounds 37 can then be converted into the corresponding saturated compounds 38 by hydrogenation (cf. Scheme XIV).

Scheme XIV: Coupling of the triflates 34 with alkenylboronic acids and subsequent hydrogenation to give the compounds 38.

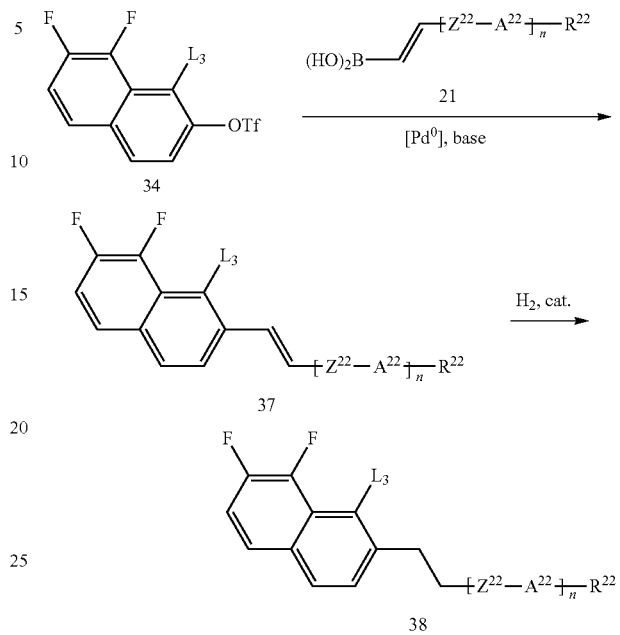

Furthermore, transition metal-promoted cross couplings of the triflates 34, for example with arylboronic acids (Suzuki coupling), terminal alkynes (Sonogashira coupling) and Grignard reagents (Kumada coupling or iron(III)-promoted cross coupling) (cf. Scheme XV, only functionalisation via coupling to Grignard reagents is shown here, for further functionalisation possibilities cf. Scheme VI or Scheme IX) are particularly preferred methods for obtaining functionalised naphthalene derivatives 39.

Scheme XV: Functionalisation of the triflates 34 by cross-coupling reactions, shown here through the example of a coupling to a Grignard reagent.

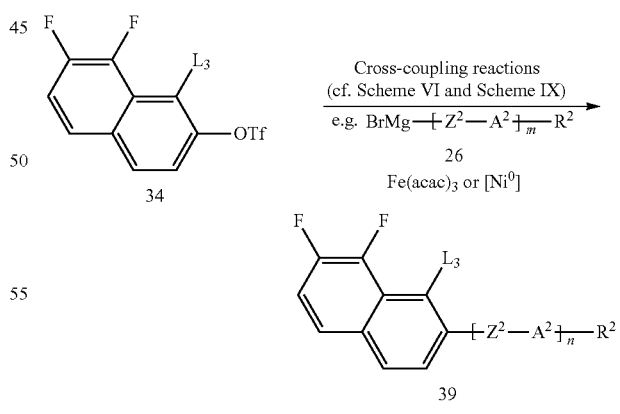

These functionalised naphthalene derivatives 39 (gen. formula) are then converted into the naphthols 2 (=2e), again via the reaction sequence of ortho-metallation, generation of a boronic acid ester and hydrolysis and oxidation thereof (cf. Scheme XVI). The process is continued with these naphthols 2 as shown in Scheme I.

Scheme XVI: Synthesis of compounds 2 where B = phenyl,
$L^1 = L^2 = F$ and $L^3 = H$ or $F$ (= 2e)

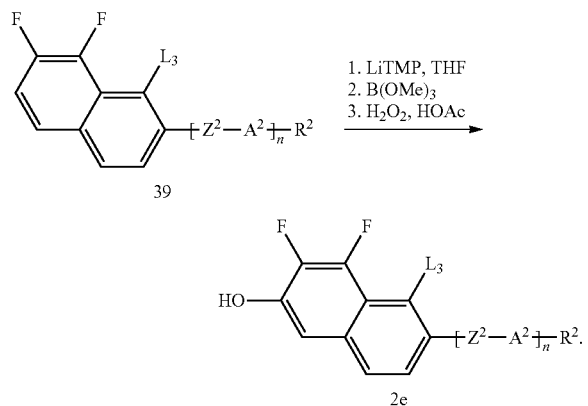

If ring B in the compounds of the formula I represents an unfluorinated phenyl radical ($L^3$=H) and if $L^1$ and/or $L^2$ are equal to H, where the substituent $L^1$ or $L^2$ that is not equal to H is preferably intended to be F, the synthesis of the compounds 2 (here 2f) is carried out starting from the compounds 13 (cf. Scheme XVII). The synthesis of the compounds 13 has already been presented above.

Scheme XVII: Synthesis of compounds 2 where B = phenyl,
$L^1 = H$ or $F$ and $L^2 = H$ or $F$ and $L^3 = H$ (= 2f)

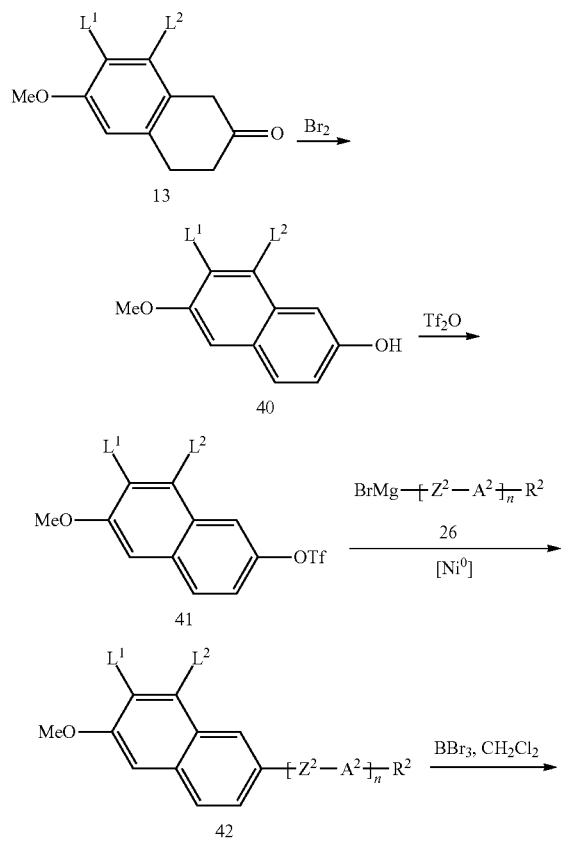

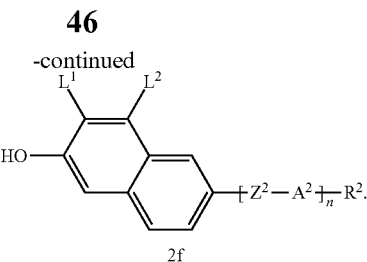

The tetralones 13 are converted into the corresponding naphthols 40 by treatment with bromine (cf. WO 2004/029015 A1). The triflates 41 obtained from 40 can then be functionalised in a variety of ways as described above for 34 (cf. Scheme XIV and Scheme XV). Scheme XVII shows only the functionalisation of 41 via a Kumada coupling. Further reactions of the triflates 41 are possible, as described above (cf. Scheme VI and Scheme IX). Cleavage of the methyl ether 42 gives the starting materials 2f required for further reactions (cf. Scheme I).

In the case where $R^2$-$(A^2$-$Z^2)_n$— in 2f is intended to represent an alkoxy radical, the synthesis must be modified. Firstly, methods can be used in the final step of the synthesis of the compounds 7f (cf. Scheme XVII) which allow the cleavage of aryl methyl ethers in the presence of other alkyl aryl ethers (A. K. Chakraborti et al. *J. Org. Chem.* 2002, 67, 6406-6414; G. Majetich et al. *Tetrahedron Lett.* 1994, 35, 8727-8730; E. Duran et al. *Heterocycles* 2002, 57, 825-856) or aryl allyl ethers (cf. M. T. Konieczny, G. Maciejewski, W. Konieczny, *Synthesis* 2005, 1575-1577). An alternative preferred process is shown in Scheme XVIII. Here, the synthesis of the intermediates 2g is carried out starting from bromotetralones 43. These are in turn converted into the corresponding 6-bromonaphthalen-2-ols 44 by treatment with bromine [WO 2004/029015 A1], which can then be converted into the desired ethers 46. The further conversion into the desired naphthols 2g is then initiated by metallation with Mg, Grignard or organolithium compounds.

Scheme XVIII: Synthesis of compounds 2 where B = phenyl and
$L^1 = H$ or $F$ and $L^2 = H$ or $F$ and $L^3 = H$ and $R^2 - A^2 - Z^2$ = alkoxy (= 2g).

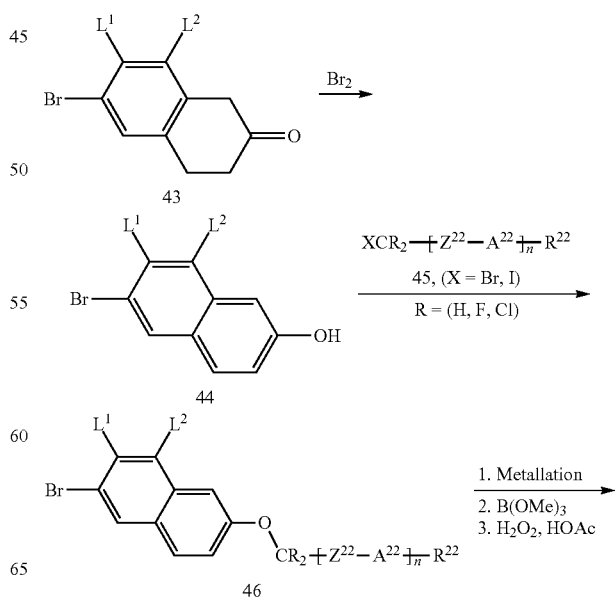

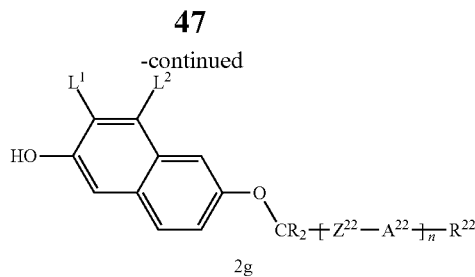

2g

The synthesis of the bromotetralones 43 is carried out in accordance with literature procedures starting from substituted 4-bromotoluenes 47 (cf. Scheme XIX, WO 2004/029015 A1; M. T. Konieczny et al. *Synthesis* 2005, 1575-1577; B. P. Imbimbo et al, *J. Med. Chem.* 2005, 48, 5705-5720). 4-Bromo-3-fluorotoluene (47, $L^1$=F, $L^2$=H) and 4-bromo-2-fluorotoluene (47, $L^1$=H, $L^2$=F) are commercially available. The methyl group of the bromotoluenes 47 is firstly brominated using NBS, and the bromomethylene compounds 48 are converted into the corresponding nitriles using potassium cyanide. These are then hydrolysed to the phenylacetic acids 49, which are then converted into the desired bromotetralones 43.

Scheme XIX: Synthesis of substituted 4-bromotetralones 43

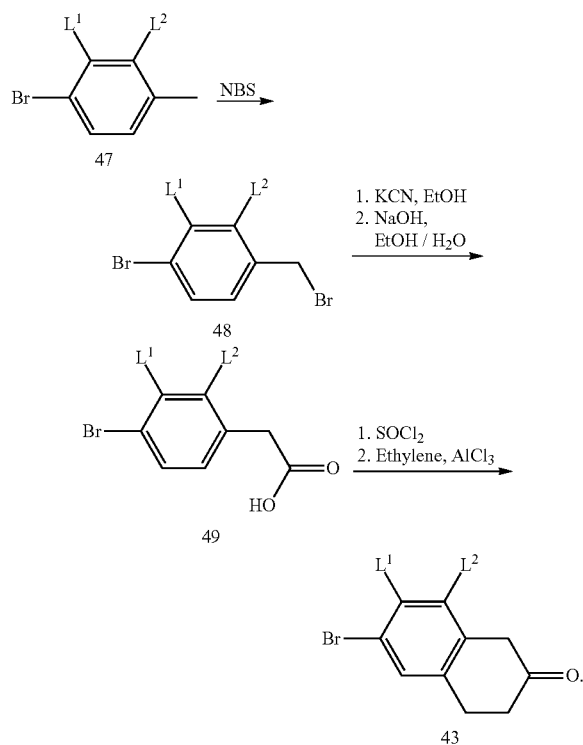

A synthesis of the unfluorinated synthesis building block 43 ($L^1$=$L^2$=H) is described by D. M. Tschaen et al. *J. Org. Chem.* 1995, 60, 4324-4330.

If ring B in the compounds of the formula I represents a fluorinated phenyl radical ($L^3$=F) and if $L^1$ and/or $L^2$ are equal to H, where the substituent $L^1$ or $L^2$ that is not equal to H is preferably intended to be F, the synthesis of the compounds 2 (especially 2h and 2i) is likewise advantageously carried out starting from the bromonaphthols 44 (cf. Scheme XX and Scheme XXI).

Scheme XX: Synthesis of compounds 2 where B = phenyl and $L^1$ = H or F and $L^2$ = H or F and $L^3$ = F and $R^2$—$A^2$—$Z^2$ = alkoxy (= 2h)

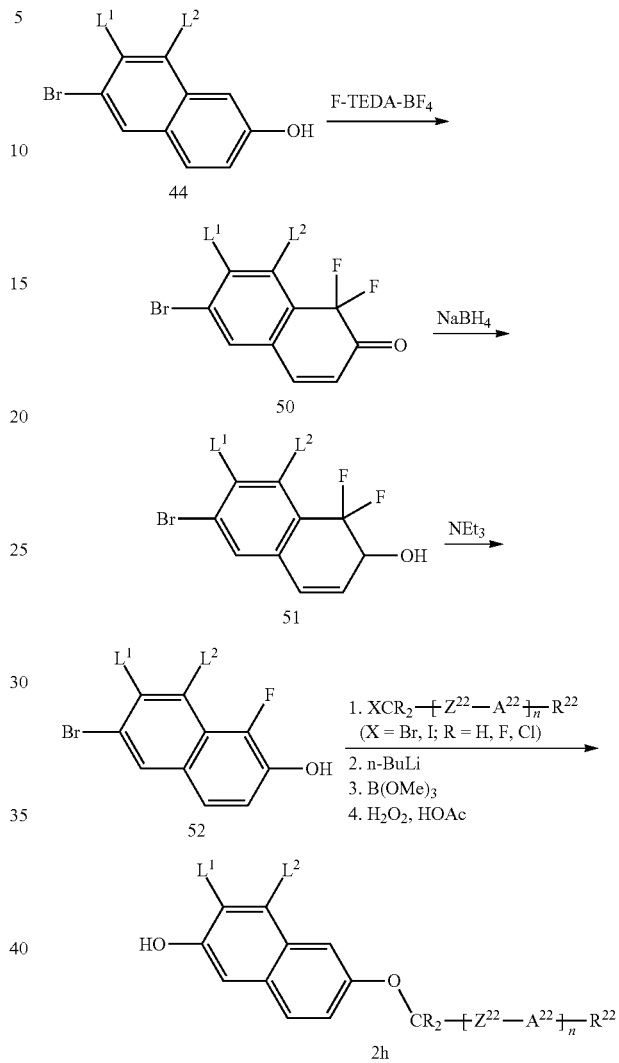

The naphthols 44 are firstly fluorinated using Selecfluor® (F-TEDA-BF$_4$) to give the difluoro-1H-naphthalen-2-ones 50 (cf. WO 2004/029015 A1), which are then reduced to 1H-naphthalen-2-ols 51. These rearomatise on treatment with base to give the compounds 52 with elimination of hydrogen fluoride. The compounds 52 are then also central intermediates for the synthesis of compounds in which $R^2$-$A^2$-$Z^2$ is intended to represent an alkoxy radical (Scheme XX, final reaction). To this end, they are firstly etherified using suitable alkyl halides and subsequently converted into the naphthol 2h.

Starting from 52, functionalisation can be carried out via the triflate 53. In the cross coupling shown (cf. Scheme XXI) with various Grignard reagents, effective discrimination between the triflate and bromine function occurs [T. Kamikawa, T. Hayashi, *Tetrahedron Lett.* 1997, 38, 7087-7090]. Conversion of 54 into the naphthol 2i gives the starting materials 2 (especially 2i) required for the further synthesis (cf. Scheme I).

Scheme XXI: Synthesis of the compounds 2 where B = phenyl and $L^1$ = H or F and $L^2$ = H or F and $L^3$ = F (= 2i)

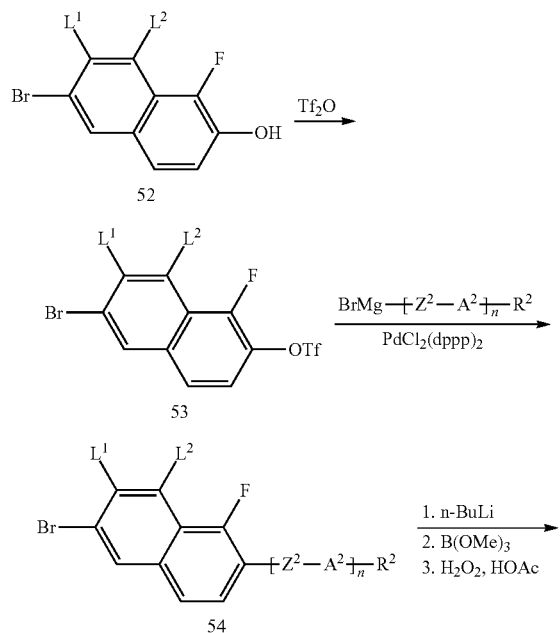

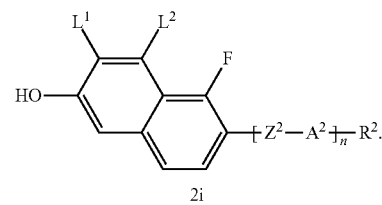

1,2,3,8,9,10-Hexahydropyrano[3,2-f]chromenes, pyranochromans for short, are compounds of the formula I in which ring 13 represents an oxygen heterocycle. These compounds are also prepared in accordance with Scheme I from the corresponding compounds 2.

If ring B in the compounds of the formula I represents an oxygen heterocycle and if $L^1$ and $L^2$ are both equal to F, 7,8-difluorochroman-6-ols 2j are required as starting materials. These are synthesised starting from 2,3-difluorophenol (51) or 3,4-difluoro-2-hydroxybenzaldehyde (55) [a) N. J. Lawrence, L. A. Hepworth, D. Rennison, A. T. McGown, J. A. Hadfield, *J. Fluorine Chem.* 2003, 123, 101-108. b) E. Marzi, J. Gorecka, M. Schlosser, *Synthesis* 2004, 1609-1618] (cf. Scheme XXII).

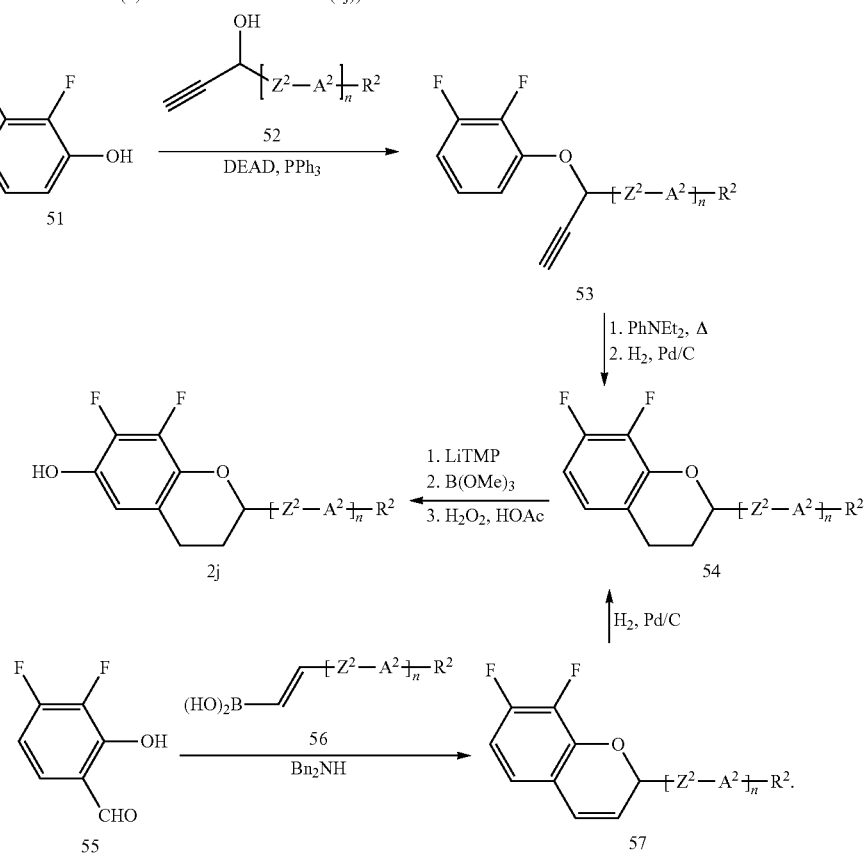

To this end, 2,3-difluorophenol (51) and a propargyl alcohol 52 are firstly reacted by a Mitsonobu etherification to give a propargyl aryl ether 53, which undergoes a thermal [3.3]-sigmatropic rearrangement under suitable reaction conditions to give a 2H-chromene. These chromenes can easily be hydrogenated under mild conditions to give the corresponding chromans 54.

Alternatively, these 7,8-difluorochromans 2j are obtained from 3,4-difluoro-2-hydroxybenzaldehyde (55) [a) N. J. Lawrence, L. A. Hepworth, D. Rennison, A. T. McGown, J. A. Hadfield, *J. Fluorine Chem.* 2003, 123, 101-108; b) E. Marzi, J. Gorecka, M. Schlosser, *Synthesis* 2004, 1609-1618] via a reaction which has been described by Petasis et al. [a) N. A. Petasis, I. Akritopoulou, *Tetrahedron Lett.* 1993, 34, 583-586; b) N. A. Petasis, I. A. Zavialov, *J. Am. Chem. Soc.* 1997, 119, 445-446; c) N. A. Petasis, I. A. Zavialov, *J. Am. Chem. Soc.* 1998, 120, 11798-11799] and further developed by Wang and Finn [Q. Wang, M. G. Finn, *Org. Lett.* 2000, 2, 4063-4065]. 2H-chromenes such as 57 are obtained in high yield from salicylaldehydes and vinylboronic acids in the presence of dibenzylamine. These can then in turn easily be hydrogenated to give the corresponding chromans 54 (see above). The intermediates 54 obtained in this way are functionalised to give the 7,8-difluorochroman-6-ols 2j by ortho-metallation and hydrolysis and oxidation of the boronic acid ester formed in situ.

If ring B in the compounds of the formula I represents a pyran ring and if $L^1$ is equal to F and $L^2$ is equal to H, the synthesis of the compounds 2 (especially 7-fluorochroman-6-ols 2k) is carried out starting from 5-bromo-4-fluoro-2-hydroxybenzaldehyde (58). This starting material 58 is accessible via literature-known processes from 3-fluorophenol by ortho-selective formylation [J. B. Blair et al., *J. Med. Chem.* 2000, 43, 4701-4710] and subsequent bromination [W. A. Caroll et al., *J. Med. Chem.* 2004, 47, 3163-3179].

Scheme XXIII: Synthesis of the compounds 2 where B = pyran and $L^1$ = F and $L^2$ = H (= 7-fluorochroman-6-ols 2k).

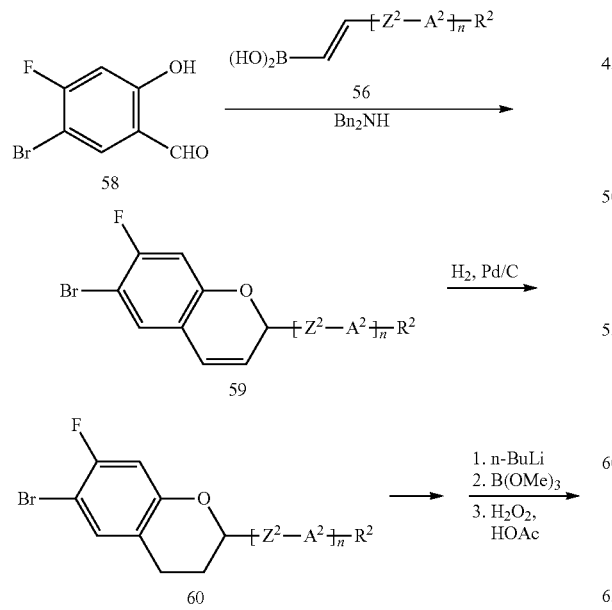

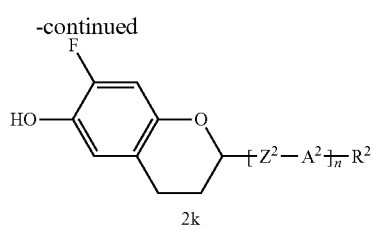

The synthesis of the chromans 60 is in turn advantageously carried out starting from 5-bromo-4-fluoro-2-hydroxybenzaldehyde (58) by the reaction with vinylboronic acids described above [Q. Wang, M. G. Finn, *Org. Lett.* 2000, 2, 4063-4065] followed by hydrogenation. The functionalisation to give the chromanol 2k is carried out as described above, this time after halogen-metal exchange.

If ring B in the compounds of the formula I represents a pyran ring and if $L^1$ is equal to H and $L^2$ is equal to F, the synthesis of the compounds 2 (especially 8-fluorochroman-6-ols 21) is carried out starting from 2-fluoro-4-bromophenol (61).

Scheme XXIV: Synthesis of the compounds 2 where B = pyran and $L^1$ = H and $L^2$ = F (= 8-fluorochroman-6-ols 21).

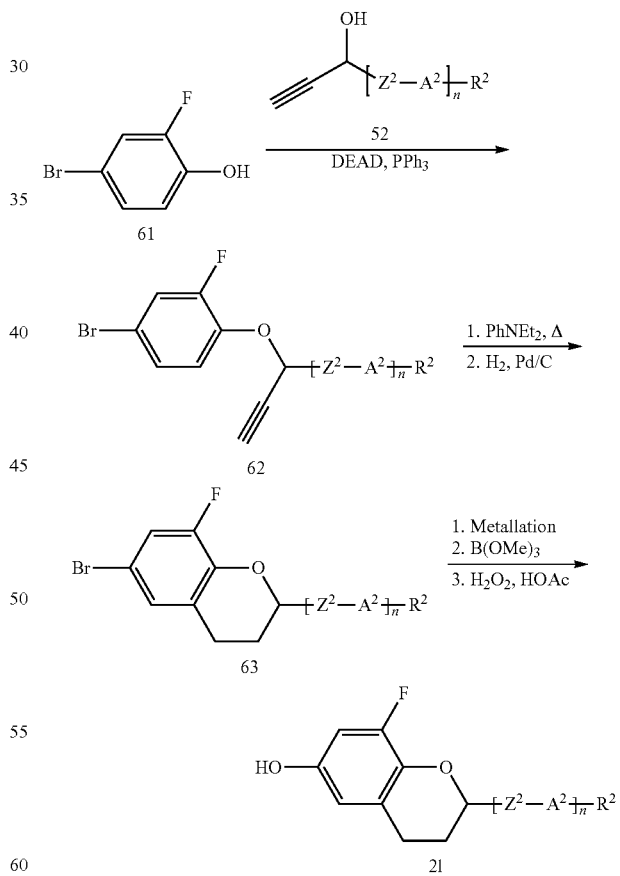

The O-heterocycle is preferably fused here by means of a Claisen rearrangement via the propargyl aryl ether 62 (cf. Scheme XXIV). The functionalisation to give the chromanol 21 is carried out using the same reaction sequence as for the regioisomer 2k.

Alternatively, the intermediates 21 can also be synthesised starting from 2-fluoro-4-bromophenol (61) via the salicylaldehyde 64 (cf. Scheme XXV). This is accessible from 61 via a Duff reaction [M. L. Micklatcher, M. Cushman, *Synthesis* 1999, 1878-1880]. The subsequent synthesis of the chroman 63 can then be carried out via the procedure described by Wang and Finn [q. Wang, M. G. Finn, *Org. Lett.* 2000, 2, 4063-4065] followed by hydrogenation.

Scheme XXV: Synthesis of the intermediates 63

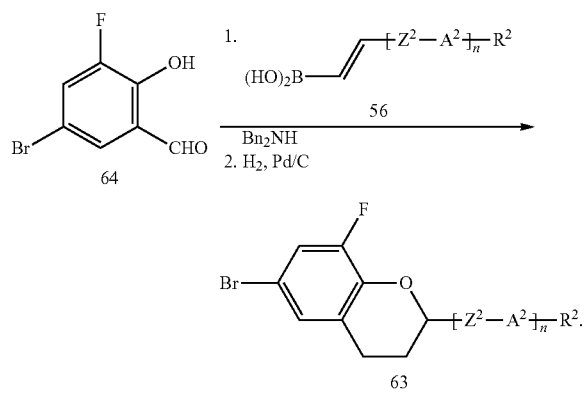

The unfluorinated compounds of the formula I ($L^1=L^2=H$) in which B represents a pyran ring (here especially 1a) can likewise be synthesised by the methods described above (Claisen rearrangement or coupling to vinylboronic acids (referred to below as the Petasis reaction)). In a particularly preferred process, the tricyclic structure is built up regioselectively by two successive Petasis reactions (cf. Scheme XXVI).

Scheme XXVI: Synthesis of the compounds 1 in which B = pyran and $L^1 = L^2 = H$ (= 1a)

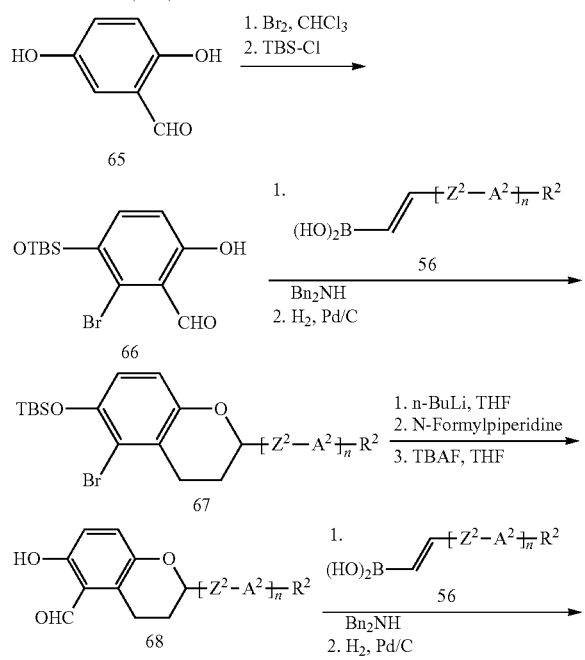

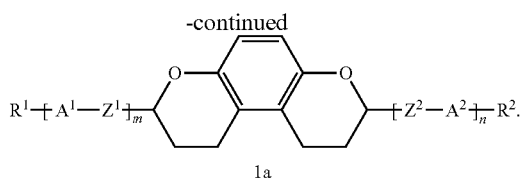

2,5-Dihydroxybenzaldehyde (65) is firstly brominated and selectively protected by processes known from the literature [Y. Hu, C. Li, B. A. Kulkarni, G. Strobel, E. Lokovsky, R. M. Torczynski, J. A. Porto, *Org. Lett.* 2001, 3, 1649-1652]. The chroman 67 is obtained by a first Petasis reaction followed by hydrogenation. Halogen-metal exchange, formylation and complete removal of the TBS protecting group gives a substrate 68 for a second Petasis reaction. Final hydrogenation results in the target compounds 1a.

If the radicals $R^1[A^1Z^1]_m$— and/or $R^2[A^2Z^2]_n$— in the compounds I are intended to contain unsaturated radicals, bridges or ring systems, the synthesis shown in Scheme I must be modified (cf. Scheme XXVII).

Scheme XXVII: Synthesis of the compounds of the formula I in which the radicals $R^1$—$[A^1$—$Z^1]_m$-and/or $R^1$—$[A^1$—$Z^1]_n$-may contain unsaturated radicals bridges or ring systems

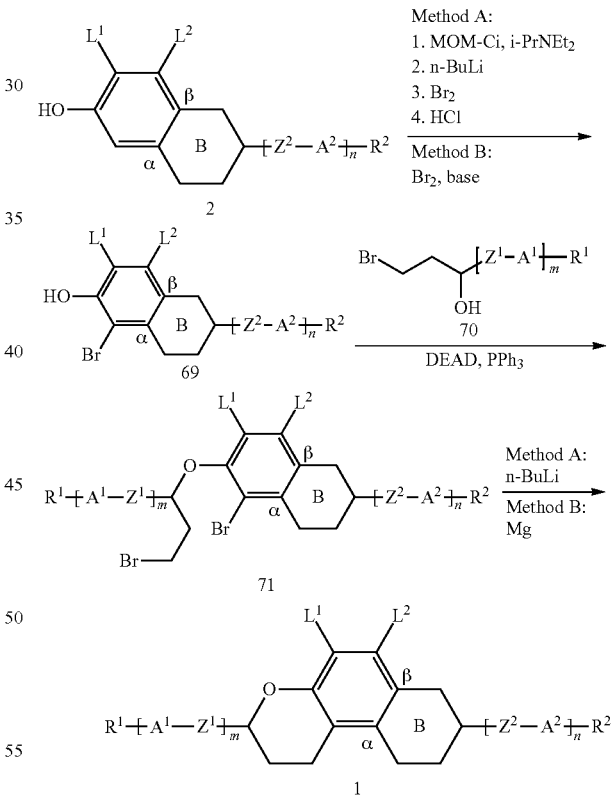

In accordance with literature procedures [a) C. K. Bradsher, D. C. Reames, *J. Org. Chem.* 1981, 46, 1384-1388 and b) L. A. Paquette et al., *J. Org. Chem.* 1994, 59, 2043-2051], the saturated O-heterocycle is then built up starting from the compounds of the formula 71. To this end, the compounds 2 are firstly brominated in a suitable manner. In a preferred process (cf. Scheme XXVII, method A), the MOM ethers of the substances 2 are firstly prepared. These are metallated selectively in the ortho-position using n-butyllithium, and the organolithium compounds are scavenged using bromine. Finally, the MOM group is cleaved to give the compounds 69. The ortho-metallation is carried out analogously to the methods in a) F. Mongin, M. Schlosser, *Tetrahedron Lett.* 1996, 37, 6551-6554; b) R. C. Ronald, M. R. Winkle, *Tetrahedron* 1983, 39, 2031-2042; c) M. R. Winkle, R. C. Ronald, *J. Org. Chem,* 1982, 47, 2101-2108; d) M. Dabowski et al. *Tetrahedron* 2005, 61, 6590-6595 or e) P. L. Coe et al. *J. Chem. Soc. Perkin Trans.* 1 1995, 2729-2737.

The halogenation can also be carried out directly by treatment with bromine (cf. Scheme XXVII, method B) (cf. a) C. W. Holzapfel, D. B. G. Williams, *Tetrahedron* 1995, 51, 8555-8564; b) K. J. Edgar, S. N. Falling, *J. Org. Chem.* 1990, 55, 5287-5291; c) R. Johnsson, A. Meijer, U. Ellervik, *Tetrahedron* 2005, 61, 11567-11663).

Etherification using bromopropanol derivatives 70 gives the compounds 71. The organolithium compound produced from these compounds (method A) or the Grignard reagent produced from these compounds (method B) cyclises spontaneously under the reaction conditions with formation of the compounds 1.

Suitable starting materials 2 in which the radical $R^2[A^2Z^2]_n$ — contains unsaturated radicals, bridges or ring systems are for the most part accessible as described above. It is only necessary to modify the syntheses for compounds 2 in which ring B represents a cyclohexyl radical and for compounds in which ring B represents a pyran ring.

For compounds 2 in which B represents a cyclohexyl radical (especially 2a, 2c), the preparation of the intermediates 10 and 14 can no longer be carried out starting from 8 and 12 respectively via elimination followed by hydrogenation (cf. Scheme II and Scheme III). 10 and 14 are therefore prepared directly from 8 and 12 respectively by an ionic reduction (cf. Scheme XXVIII).

Scheme XXVIII: Alternative synthesis of the compounds 10 and 14

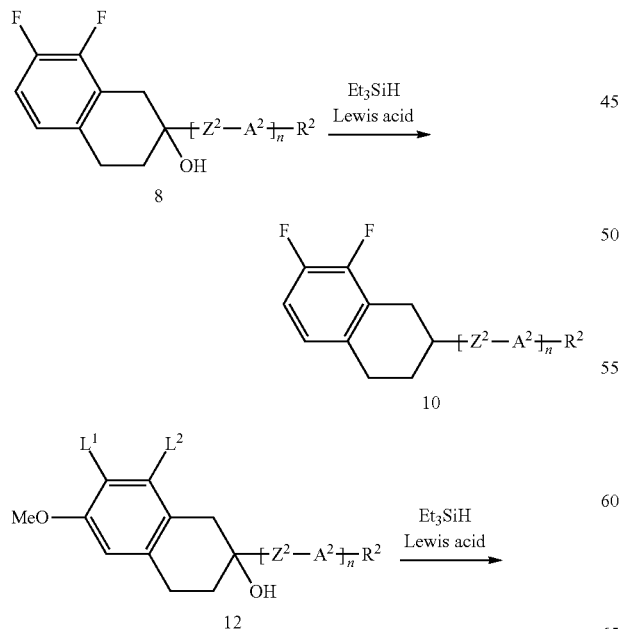

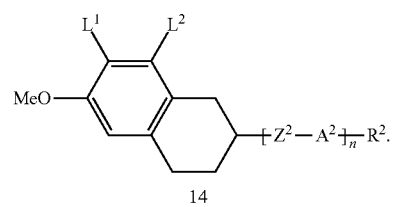

If it is intended to synthesise compounds 2 in which $R^2[A^2Z^2]_n$ contains unsaturated radicals, bridges or ring systems and B is intended to represent a pyran ring, the following process is required (cf. Scheme XXIX).

Scheme XXIX: Synthesis of specially substituted chroman-6-ols 77

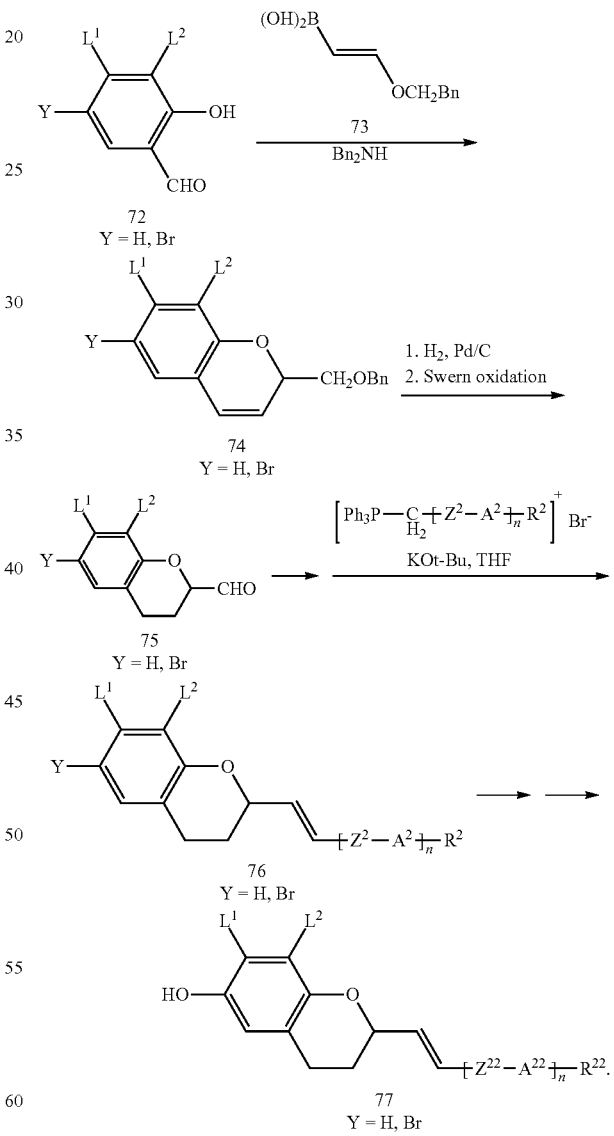

Starting from salicylaldehydes 72 (Y=H, Br), the chromene 74 is built up using the boronic acid 73 [R. A. Batey, A. N. Avinash, A. J. Lough, *J. Am. Chem. Soc.* 1999, 121, 450-451]. Hydrogenation and oxidation gives the intermediate 75. The group $R^2[A^2Z^2]_n$— can then be built up starting from this (for example by Wittig olefination).

Methods for functionalisation to give the chroman-6-ols 77 have been described adequately.

For the synthesis of compounds I in which B represents a fluorinated cyclohexane ring (here especially=1c) or a fluorinated cyclohexene ring (here especially=1d), the following reaction sequence starting from compounds I in which B is a cyclohexene ring (here especially=1b) is suitable (cf. Scheme XXX).

Scheme XXX: Synthesis of compounds I where $L^1$ = H or F, $L^2$ = H or F and B = fluorinated cyclohexane (here especially 1c) and synthesis of compounds I where $L^1$ = H or F, $L^2$ = H or F and B = fluorinated cyclohexene (here especially 1d)

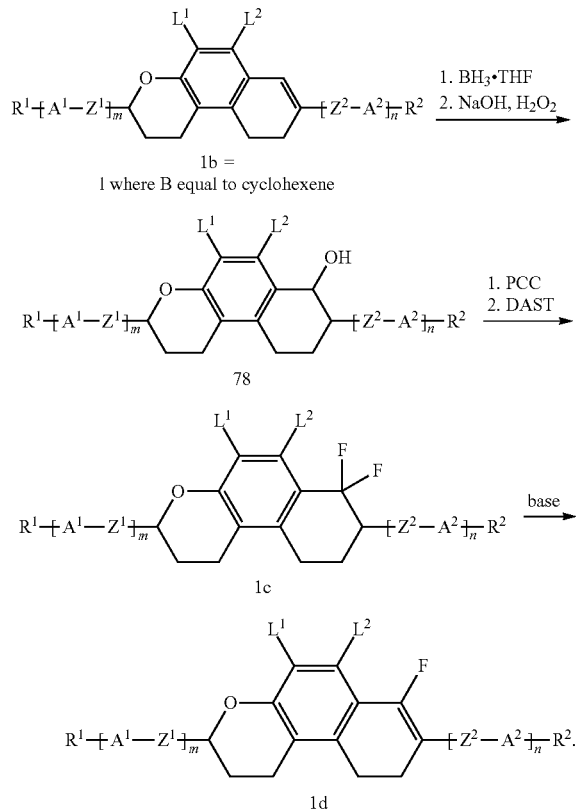

The reaction schemes shown should only be regarded as illustrative. The person skilled in the art will be able to carry out corresponding variations of the syntheses presented and also follow other suitable synthetic routes to give the compounds of the formula I.

In accordance with the syntheses shown above, the present invention also encompasses, in an embodiment, one or more processes for the preparation of the compounds of the formula I. The invention thus encompasses a process for the preparation of the compounds of the formula I which is characterised in that it includes a process step in which a compound of the formula

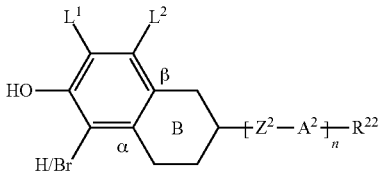

in which
n, $A^2$ and $Z^2$ are as defined above for formula I, and
$R^{22}$ is as defined for $R^1$ and may additionally denote —OTs, OTf, OMes or —B(OH)$_2$, —B(O-alkyl)$_2$, —B<(O—C$_{2-10}$-alkylene-O),
is etherified on the hydroxyl group using a suitable organic radical to give a compound of the formula

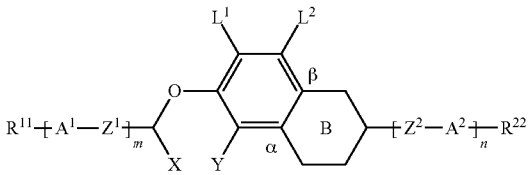

in which m, n, $A^1$, $Z^1$, $A^2$ and $Z^2$ are as defined above for formula I,
$R^{11}$ and $R^{22}$ are as defined for $R^1$ and may additionally denote —OTs, —OTf, —OMes or —B(OH)$_2$ or —B(O-alkyl)$_2$ or —B<(O—C$_{2-10}$-alkylene-O),
X denotes —CH$_2$CH$_2$Br or —C≡CH, and
Y denotes H or Br,
and cyclised at groups X and Y, preferably to give a compound of the formula I. The cyclisation is preferably carried out after the first process step. The process product is a compound of the formula I or an intermediate which is suitable for the preparation of compounds of the formula I. As already mentioned, the compounds of the general formula I can be used in liquid-crystalline media.

The present invention therefore also relates to a liquid-crystalline medium comprising at least two liquid-crystalline compounds, comprising at least one compound of the general formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R" (II)

R'-L-COO-E-R" (III)

R'-L-OOC-E-R" (IV)

R'-L-CH$_2$CH$_2$-E-R" (V)

R'-L-CF$_2$O-E-R" (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes

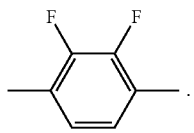

In the compounds of group B, which are referred to by the sub-formulae (IIb), (IIIb), (IVb), (Vb) and (VIb), R' and R" are as defined for the compounds of the sub-formulae (IIa) to (VIa) and are preferably alkyl, alkenyl, alkoxy or alkoxyalkyl (oxaalkyl).

In a further smaller sub-group of the compounds of the formulae (II), (III), (IV), (V) and (VI), R" denotes —CN. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' is as defined for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto Besides the compounds of the general formula I according to the invention, the media according to the invention preferably comprise one or more compounds from groups A, B and/or C. The proportions by weight of the compounds from these groups in the media according to the invention are:

group A:
from 0 to 90%, preferably from 20 to 90%, in particular from 30 to 90%.

group B:
from 0 to 80%, preferably from 10 to 80%, in particular from 10 to 70%.

group C:
from 0 to 80%, preferably from 5 to 80%, in particular from 5 to 50%.

The media according to the invention preferably comprise from 1 to 40%, particularly preferably from 5 to 30%, of the compounds of the formula I according to the invention. The media preferably comprise one, two, three, four or five compounds of the formula I according to the invention.

Examples of the compounds of the formulae (II), (III), (IV), (V) and (VI) are the compounds shown below:

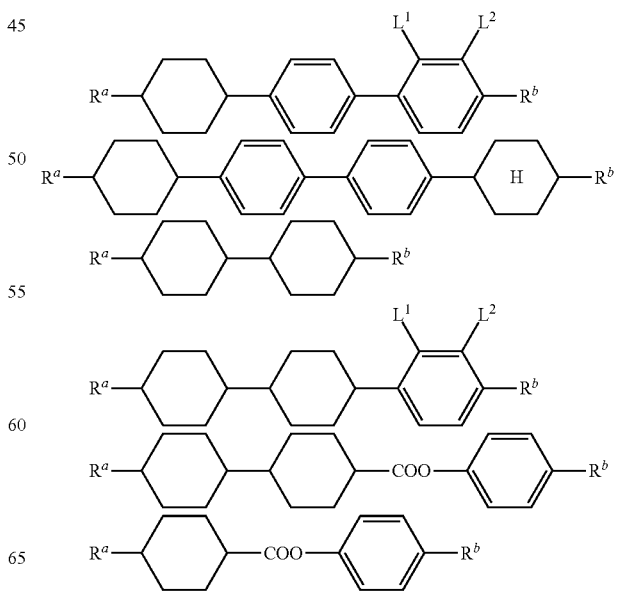

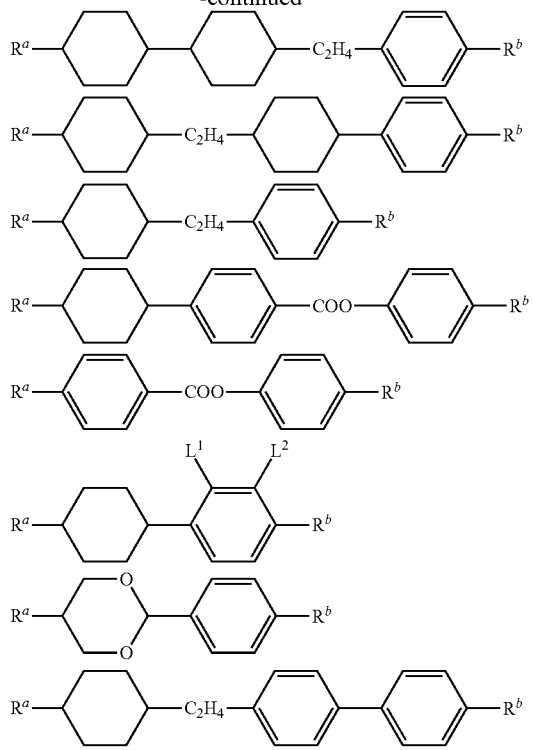
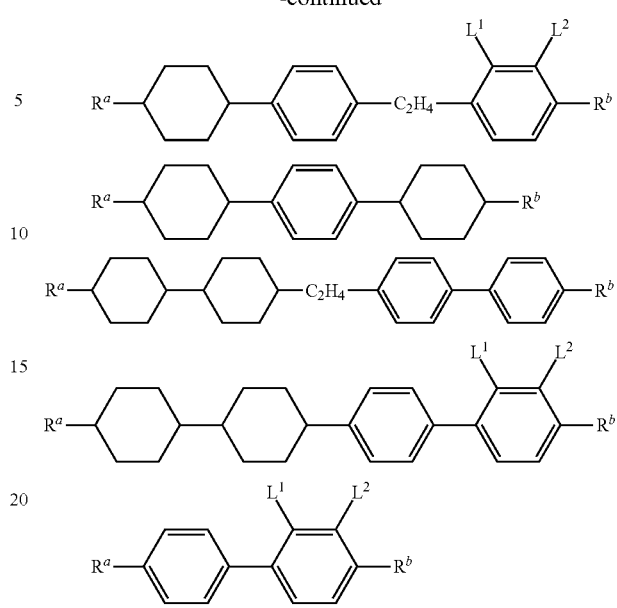
where $R^a$, $R^b$, independently of one another, denote $-C_pH_{2p+1}$ or $-OC_pH_{2p+1}$, and p=1, 2, 3, 4, 5, 6, 7 or 8, and $L^1$, $L^2$, independently of one another, denote —H or —F,
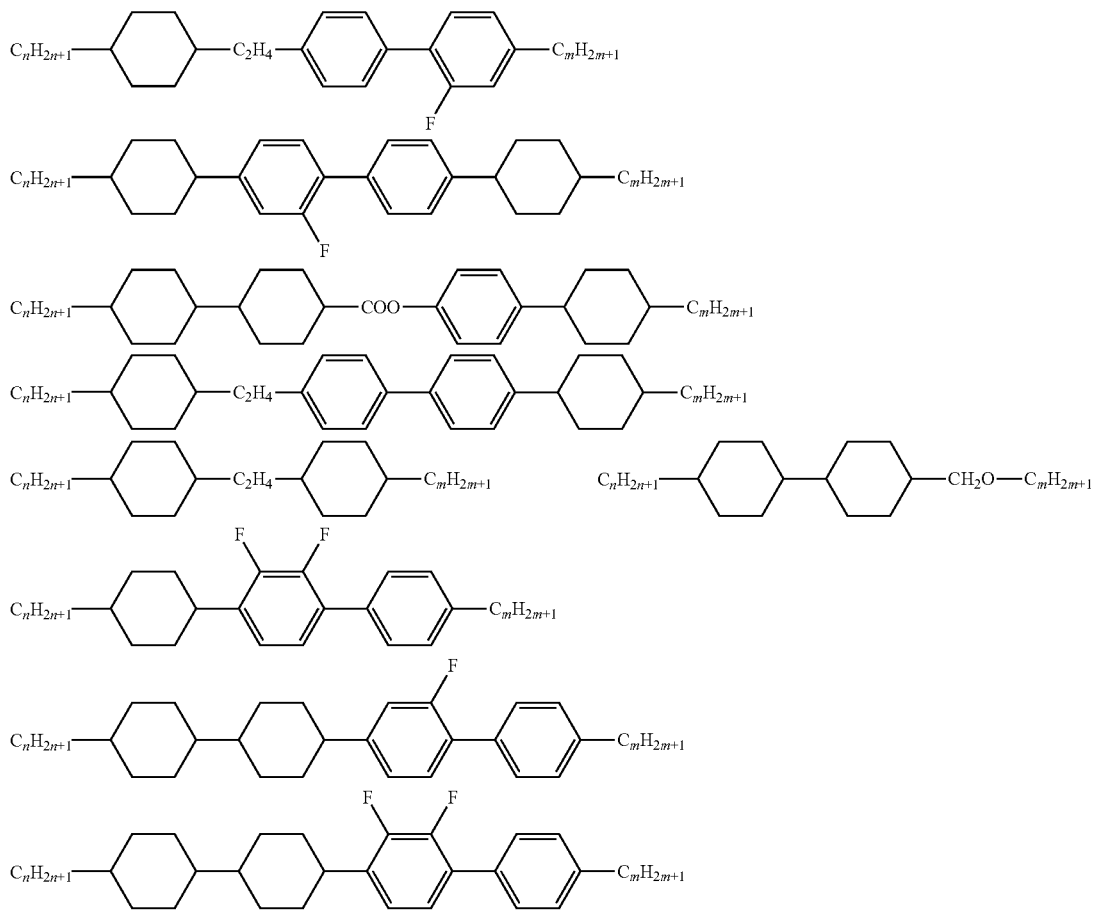

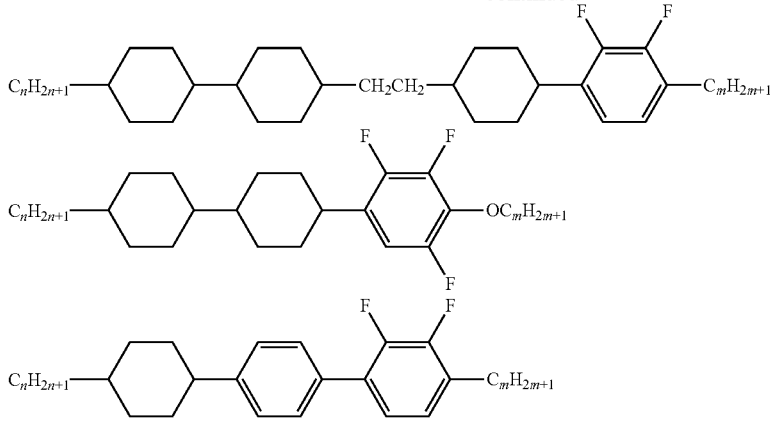

where m, n, independently of one another, denote 1, 2, 3, 4, 5, 6, 7 or 8.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

Owing to their negative Δs, the compounds of the formula I are particularly suitable for use in VA-TFT displays.

The present invention therefore also relates to electro-optical liquid-crystal display elements containing a liquid-crystalline medium according to the invention.

Further combinations of the embodiments and variants of the invention in accordance with the description arise from the claims.

The invention is explained in greater detail below with reference to working examples, but without intending to be restricted thereby. The person skilled in the art will be able to glean from the examples working details that are not given in detail in the general description, generalise them in accordance with general expert knowledge and apply them to a specific problem.

Besides the usual and well-known abbreviations, the following abbreviations are used:

C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, Δn denotes the optical anisotropy (589 nm, 20° C.) and Δ∈ denotes the dielectric anisotropy (1 kHz, 20° C.). The dielectric anisotropy Δ∈ is determined at 20° C. and 1 kHz. The optical anisotropy Δn is determined at 20° C. and a wavelength of 589.3 nm.

The Δ∈ and Δn values and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for Δ∈) or ZLI-4792 (for Δn, $\gamma_1$) (mixtures, Merck KGaA, Darmstadt).

The abbreviations have the following meanings:
DIAD diisopropyl azodicarboxylate
MTBE methyl tert-butyl ether
THF tetrahydrofuran
DMF dimethylformamide
in vac. in vacuo (about $10^{-2}$ bar)
sat. saturated
n-BuLi n-butyllithium, solution in hexane
Mes mesyl group
MOM methoxymethyl
RT room temperature
F-TEDA-BF$_4$  1-chloromethyl-4-fluoro-1,4-diazabicyclo[2.2.2]octane bistetrafluoroborate
TMP 2,2,6,6-tetramethylpiperidine
dppp 1,3-bis(diphenylphosphine)propane
Tf trifyl group
Ts tosyl group
NMP N-methyl-2-pyrrolidone

EXAMPLES

The starting substances can be obtained in accordance with generally accessible literature procedures or commercially.

Example 1

5,6-Difluoro-3-(4-propylcyclohexyl)-1,2,3,8,9,10-hexahydropyrano[3,2-f]chromene

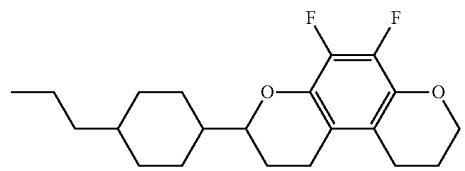

1.1 Preparation of 1,2-difluoro-3-prop-2-ynyloxybenzene

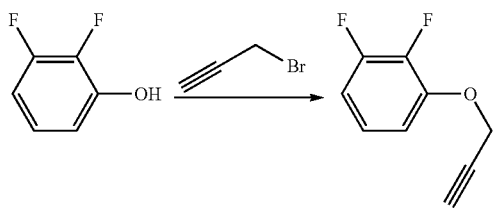

115.0 g (0.88 mol) of 2,3-difluorophenol are refluxed for 3 h in 1.6 l of ethyl methyl ketone together with 118.2 ml (17.7 mol) of propargyl bromide (80% soln. in toluene) and 146.6 g (138.2 mol) of potassium carbonate. The batch is filtered, and the filter residue is washed with MTBE. The filtrate is evaporated to dryness, and the residue is purified by column chromatography (SiO$_2$, n-heptane:MTBE=3:1).

1.2 Preparation of 7,8-difluoro-2H-chromene

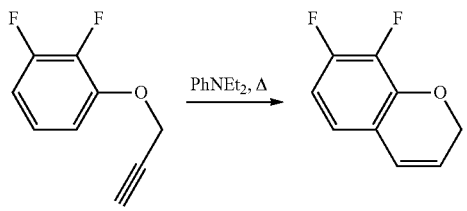

73.0 g (0.43 mol) of 1,2-difluoro-3-prop-2-ynyloxybenzene are heated at 200° C. for 3 h in an autoclave together with 126.0 g (2.17 mol) of potassium fluoride in 650 ml of N,N-diethylaniline. Water is added to the batch, which is then acidified using 25% hydrochloric acid. The solution is extracted with MTBE, and the combined organic phases are washed with sat. sodium chloride soln. The solution is dried using sodium sulfate and evaporated to dryness. The residue is purified by column chromatography (SiO$_2$, n-heptane: MTBE=10:1). In this way, a mixture of 7,8-difluoro-2H-chromene and the starting material 1,2-difluoro-3-prop-2-ynyloxybenzene is obtained.

1.3 Preparation of 7,8-difluorochroman

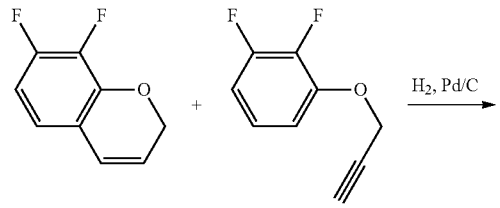

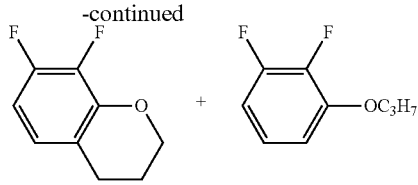

A mixture of 7,8-difluoro-2H-chromene and 1,2-difluoro-3-prop-2-ynyloxybenzene (43.2 g) is hydrogenated at RT for 1 h in 430 ml of THF in the presence of Pd/C (5% of Pd). The batch is evaporated to dryness, and the crude product is purified by column chromatography (SiO$_2$, n-pentane: 1-chlorobutane=4:1), giving pure 7,8-difluorochroman as a pale-yellowish liquid.

1.4 Preparation of 7,8-difluorochroman-6-ol

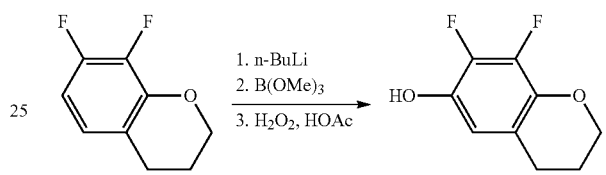

81.2 ml (0.13 mol) of n-BuLi (15% soln. in hexane) are added to a soln. of 20.0 g (0.12 mol) of 7,8-difluorochroman in 400 ml of THF at –70° C. After 3 h at this temperature, 14.4 ml (0.13 mol) of trimethyl borate are added dropwise, and the batch is warmed to RT. 30 ml of dilute acetic acid (about 30%) are added, and 30 ml of aqueous hydrogen peroxide solution (35%) are carefully added to the batch. When the addition is complete, the mixture is stirred at RT for 17 h. Water is added, and the batch is acidified using 2 N hydrochloric acid. The solution is extracted a number of times with MTBE, and the combined organic phases are washed successively with water, sat. sodium chloride soln. and ammonium iron(II) sulfate soln. The solution is dried using sodium sulfate and evaporated to dryness. The crude product is purified by column chromatography (SiO$_2$, n-heptane: MTBE=2:1).

1.5 Preparation of 7,8-difluoro-6-[1-(4-propylcyclohexyl)prop-2-ynyloxy]-chroman

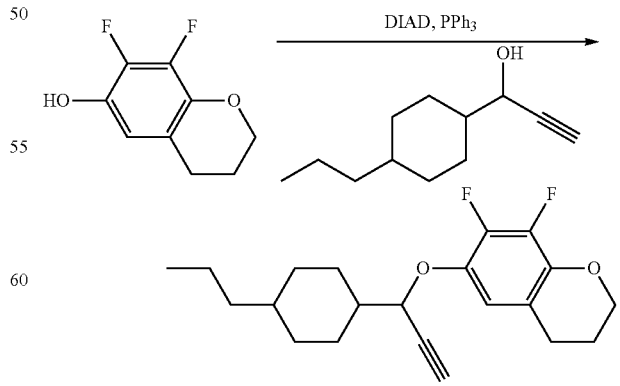

5.0 g (26.9 mmol) of 7,8-difluorochroman-6-ol are initially introduced in 65 ml of THF together with 5.33 g (29.6 mmol)

of 1-(4-propylcyclohexyl)-prop-2-yn-1-ol and 8.45 g (32.2 mmol) of triphenylphosphine, and 6.79 ml (34.9 mmol) of DIAD are added over the course of 30 min with ice-cooling. After 19 h at RT, semi-saturated sodium chloride solution is added, and the mixture is extracted a number of times with MTBE. The combined organic phases are washed with water and saturated sodium chloride solution, and the solution is dried using sodium sulfate. The residue remaining after removal of the solvents is purified by column chromatography (SiO$_2$, n-pentane:MTBE=2:1), giving 7,8-difluoro-6-[1-(4-propylcyclohexyl)prop-2-ynyloxy]chroman as a pale-brown oil.

1.6 Preparation of 5,6-difluoro-8-(4-propylcyclohexyl)-1,2,3,8-tetrahydropyrano[3,2-f]chromene

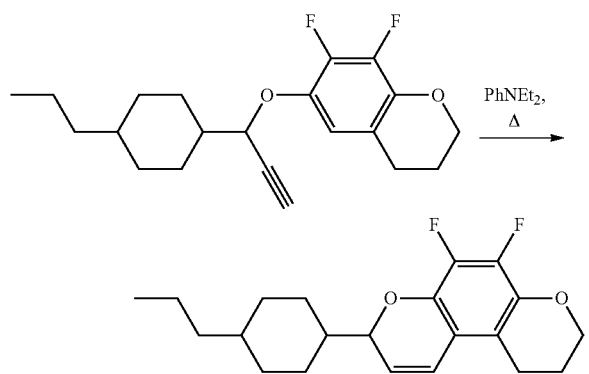

6.0 g (17.2 mmol) of 7,8-difluoro-6-[1-(4-propylcyclohexyl)prop-2-ynyloxy]-chroman are heated at 200° C. for 6 h together with 2.0 g (34.4 mmol) of potassium fluoride in 55 ml of N,N-diethylaniline. After cooling, water is added, and the mixture is acidified using 25% hydrochloric acid. The batch is extracted with MTBE, and the organic phase is washed with saturated sodium chloride solution. The solution is dried using sodium sulfate and evaporated to dryness. The crude product is purified by column chromatography (SiO$_2$, 1-chlorobutane), giving 5,6-difluoro-8-(4-propylcyclohexyl)-1,2,3,8-tetrahydropyrano[3,2-f]chromene as a pale-brown oil.

1.7 Preparation of 5,6-difluoro-3-(4-propylcyclohexyl)-1,2,3,8,9,10-hexahydropyrano[3,2-f]chromene

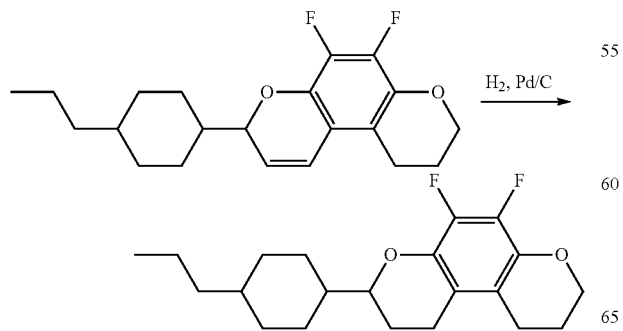

4.0 g (11.5 mmol) of 5,6-difluoro-8-(4-propylcyclohexyl)-1,2,3,8-tetrahydropyrano[3,2-f]chromene are hydrogenated at atmospheric pressure in THF and in the presence of Pd/C (5% of Pd). The reaction solution is filtered, and the filtrate is evaporated to dryness. The residue is purified by column chromatography (SiO$_2$, n-heptane:1-chlorobutane=1:1). The further purification is carried out by repeated recrystallisation from n-heptane at 5° C., giving 5,6-difluoro-3-(4-propylcyclohexyl)-1,2,3,8,9,10-hexahydropyrano[3,2-f]chromene as a colourless solid (m.p. 152° C.).

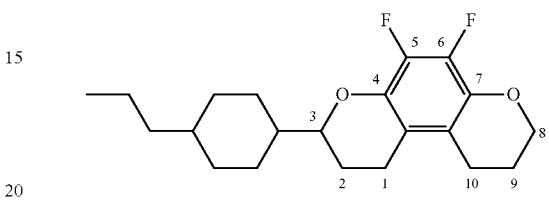

Δ∈=−10.4

Δn=0.0663

C 152 I $^1$H-NMR (250 MHz, CHCl$_3$): δ=4.23-4.07 (m, 2H, 8-H), 3.68-3.61 (m, 1H, 3-H), 2.62-2.39 (m, 4H, H$_{aliph.}$), 2.09-1.97 (m, 4H, H$_{aliph.}$), 1.85-1.73 (m, 4H, H$_{aliph.}$), 1.71-1.50 (m, 1H, H$_{aliph.}$), 1.40-1.25 (m, 2H, H$_{aliph.}$), 1.22-1.03 (m, 4H, H$_{aliph.}$), 0.99-0.81 (m, 6H, H$_{aliph.}$).

$^{19}$F-NMR (235 MHz, CHCl$_3$): δ=−161.8 (d, 1F, J=19.5 Hz), −162.2 (d, 1F, J=19.5 Hz).

MS (EI): m/e (%)=350 (100, M$^+$).

Example 2

5,6-Difluoro-3-pentyl-8-(4-propylcyclohexyl)-1,2,3,8,9,10-hexahydropyrano[3,2-f]chromene

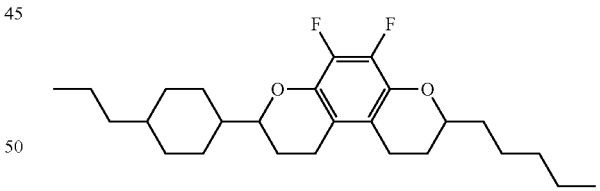

2.1 Preparation of 1-(1-ethynylhexyloxy)-2,3-difluorobenzene

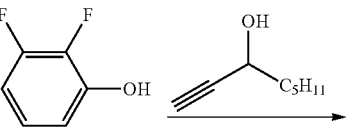

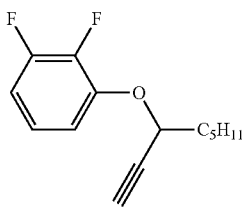

2.4 g (0.33 mol) of 2,3-difluorophenol are initially introduced in 1.2 l of THF together with 50.0 ml (0.34 mol) of 1-octyn-3-ol and 94.1 g (0.36 mol) of triphenylphosphine, and a solution of 76.1 ml (0.39 mol) of DIAD in 100 ml of THF is added dropwise. After 19 h at RT, the batch is diluted with MTBE and washed with water. The aqueous phase is extracted with MTBE, and the combined organic phases are washed with saturated sodium chloride solution. The solution is dried using sodium sulfate and evaporated to dryness. The residue is purified by column chromatography (SiO$_2$, 1-chlorobutane), giving 1-(1-ethynylhexyloxy)-2,3-difluorobenzene as a colourless oil.

2.2 Preparation of 7,8-difluoro-2-pentyl-2H-chromene

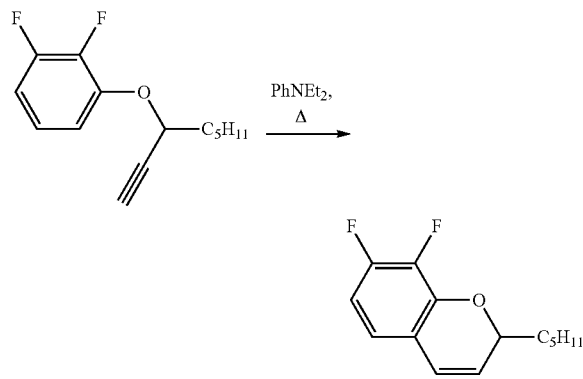

62.0 g (0.26 mol) of 1-(1-ethynylhexyloxy)-2,3-difluorobenzene are heated at 195° C. for 2 h in 390 ml of N,N-diethylaniline. The batch is diluted with MTBE and washed a number of times with 1 N HCl. The organic phase is dried using sodium sulfate and evaporated to dryness. The residue is purified by column chromatography (SiO$_2$, n-pentane:1-chlorobutane=5:1), giving 7,8-difluoro-2-pentyl-2H-chromene as a brown oil.

2.3 Preparation of 7,8-difluoro-2-pentylchroman

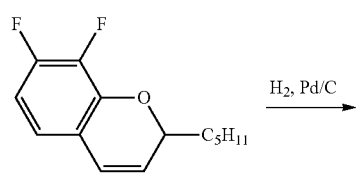

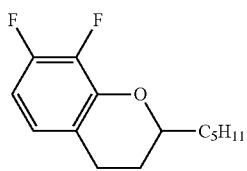

51.0 g (0.21 mol) of 7,8-difluoro-2-pentyl-2H-chromene are hydrogenated at RT for 1 h in 510 ml of toluene in the presence of Pd/C (5% of Pd). The batch is evaporated to dryness: the crude product (yellowish liquid) can be used directly for the next step.

2.4 Preparation of 7,8-difluoro-2-pentylchroman-6-ol

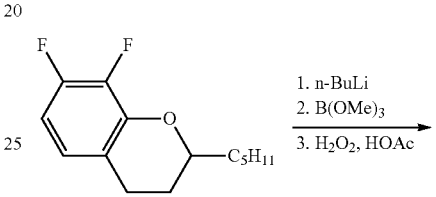

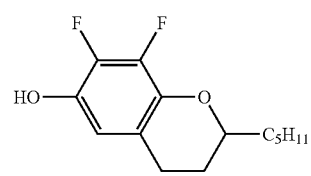

52.4 g (about 0.22 mol) of crude 7,8-difluoro-2-pentylchroman are initially introduced in 400 ml of THF, and 150.7 ml (0.24 mol) of n-BuLi (15% soln. in hexane) are added at −70° C. After 3 h at this temperature, 26.8 ml (0.24 mol) of trimethyl borate are added dropwise, and the batch is warmed to RT. 55 ml of dilute acetic acid (about 30%) are added, and 57 ml of hydrogen peroxide solution (35%) are carefully added to the batch. When the addition is complete, the mixture is stirred at RT for 17 h.

Water is added, and the batch is acidified using HCl. The solution is extracted a number of times with MTBE, and the combined organic phases are washed successively with water, sat. sodium chloride soln. and ammonium iron(II) sulfate soln. The solution is dried using sodium sulfate and evaporated to dryness. The crude product is purified by column chromatography (SiO$_2$, n-heptane:MTBE=2:1).

2.5 Preparation of 7,8-difluoro-2-pentyl-6-[1-(4-propylcyclohexyl)prop-2-ynyloxy]chroman

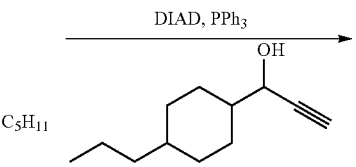

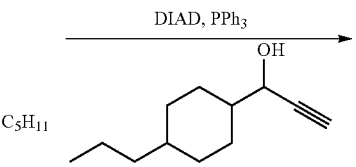

-continued

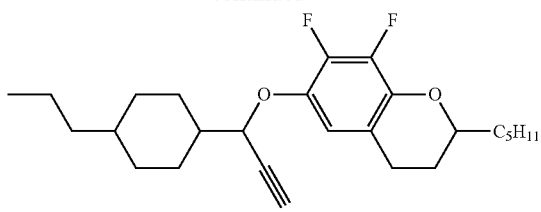

8.0 g (31.2 mmol) of 7,8-difluoro-2-pentylchroman-6-ol are initially introduced in 75 ml of THF together with 6.75 g (37.4 mmol) of 1-(4-propylcyclohexyl)prop-2-yn-1-ol and 9.83 g (37.6 mmol) of triphenylphosphine, and 7.89 ml (40.6 mmol) of DIAD are added over the course of 30 min with ice-cooling. After 20 h at RT, semi-saturated sodium chloride solution is added, and the mixture is extracted a number of times with MTBE. The combined organic phases are washed with water and saturated sodium chloride solution, and the solution is dried using sodium sulfate. The residue remaining after removal of the solvents is purified by column chromatography (SiO$_2$, n-pentane:MTBE=2:1), giving 7,8-difluoro-2-pentyl-6-[1-(4-propylcyclohexyl)prop-2-ynyloxy]chroman as a pale-brown oil.

2.6 Preparation of 5,6-difluoro-3-pentyl-8-(4-propyl-cyclohexyl)-1,2,3,8-tetrahydropyrano[3,2-f]chromene

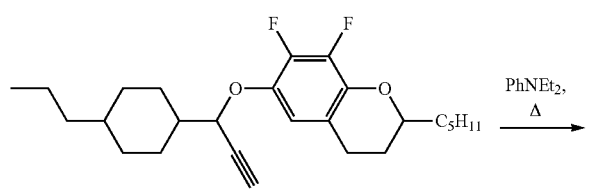

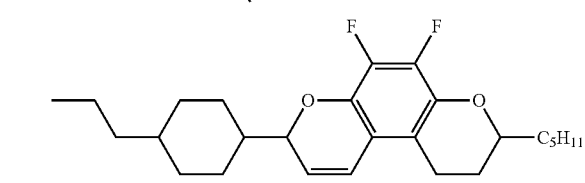

9.7 g (23.2 mmol) of 7,8-difluoro-2-pentyl-6-[1-(4-propylcyclohexyl)prop-2-ynyloxy]chroman are heated at 200° C. for 6 h together with 2.7 g (46.5 mmol) of potassium fluoride in 75 ml of N,N-diethylaniline. After cooling, water is added, and the mixture is acidified using 25% hydrochloric acid. The batch is extracted with MTBE, and the organic phase is washed with saturated sodium chloride solution. The solution is dried using sodium sulfate and evaporated to dryness. The crude product is purified by column chromatography (SiO$_2$, 1-chlorobutane:pentane=4:1), giving 5,6-difluoro-3-pentyl-8-(4-propylcyclohexyl)-1,2,3,8-tetrahydropyrano[3,2-f]chromene as a pale-brown oil.

2.7 Preparation of 5,6-difluoro-3-pentyl-8-(4-propylcyclohexyl)-1,2,3,8,9,10-hexahydropyrano[3,2-f]chromene

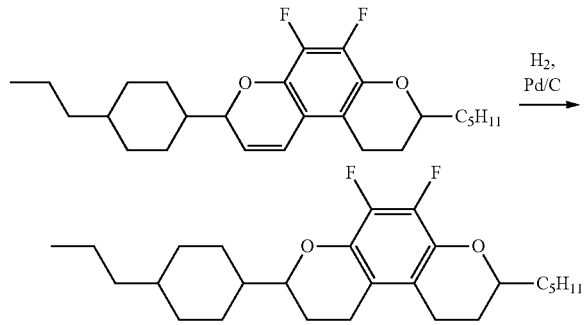

4.8 g (11.5 mmol) of 5,6-difluoro-3-pentyl-8-(4-propylcyclohexyl)-1,2,3,8-tetrahydropyrano[3,2-f]chromene are hydrogenated at atmospheric pressure in THF and in the presence of Pd/C (5% of Pd). The reaction solution is filtered, and the filtrate is evaporated to dryness. The residue is purified by column chromatography (SiO$_2$, n-heptane 1-chlorobutane=8:1).

Further purification is carried out by recrystallisation from n-heptane at 5° C., giving 5,6-difluoro-3-pentyl-8-(4-propylcyclohexyl)-1,2,3,8,9,10-hexahydropyrano[3,2-f]chromene as a colourless solid. The further resolution of the diastereomer mixture obtained is carried out, for example, by preparative HPLC.

Isomer 1 (m.p. 128° C.):

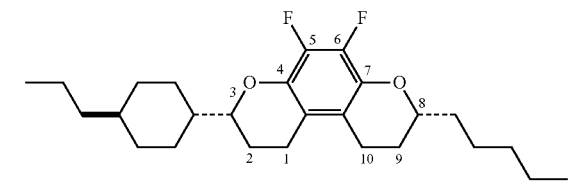

Δε=−11.2
Δn=0.0742
C 128 I $^1$H-NMR (500 MHz, CHCl$_3$): δ=3.94-3.90 (m, 1H, 8-H), 3.67-3.64 (m, 1H, 3-H), 2.60-2.54 (m, 2H, H$_{aliph.}$), 2.48-2.41 (m, 2H, H$_{aliph.}$), 2.06-1.99 (m, 3H, H$_{aliph.}$), 1.82-1.68 (m, 6H, H$_{aliph.}$), 1.61-1.49 (m, 4H, H$_{aliph.}$), 1.46-1.40 (m, 1H, H$_{aliph.}$), 1.35-1.28 (m, 6H, H$_{aliph.}$), 1.26-1.07 (m, 4H, H$_{aliph.}$), 0.96-0.87 (m, 8H, H$_{aliph.}$).

$^{19}$F-NMR (235 MHz, CHCl$_3$): δ=−163.1 (m, 2F).

MS (EI): m/e (%)=420 (100, M$^+$).

Isomer 2 (m.p. 131° C.):

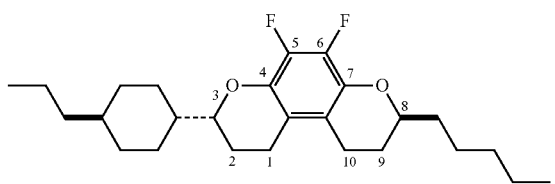

Δε=−9.2
Δn=0.0894
C 131 I
$^1$H-NMR (500 MHz, CHCl$_3$): δ=3.91-3.86 (m, 1H, 8-H), 3.65-3.61 (m, 1H, 3-H), 2.53-2.49 (m, 4H, H$_{aliph.}$), 2.06-2.00 (m, 3H, H$_{aliph.}$), 1.83-1.66 (m, 6H, H$_{aliph.}$), 1.62-1.50 (m, 4H, H$_{aliph.}$), 1.47-1.40 (m, 1H, H$_{aliph.}$), 1.38-1.28 (m, 6H, H$_{aliph.}$), 1.26-1.07 (m, 4H, H$_{aliph.}$), 0.97-0.87 (m, 8H, H$_{aliph.}$).
$^{19}$F-NMR (235 MHz, CHCl$_3$): δ=−163.8 (m, 2F).
MS (EI): m/e (%)=420 (100, M$^+$).

Example 3

5,6-Difluoro-3-pentyl-8-propyl-1,2,3,8,9,10-hexahydropyrano-[3,2-f]chromene

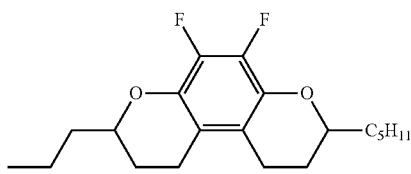

3.1 Preparation of 6-(1-ethynylbutoxy)-7,8-difluoro-2-pentylchroman

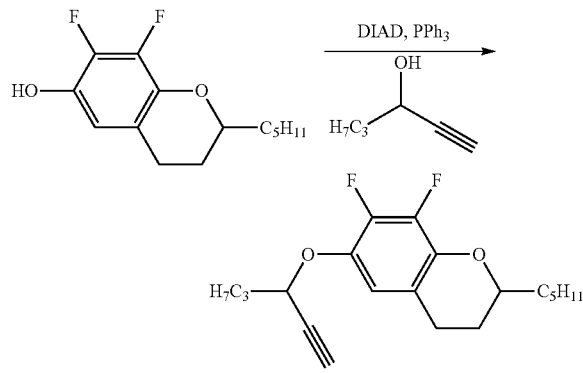

10.0 g (39.0 mmol) of 7,8-difluoro-2-pentylchroman-6-ol are initially introduced in 140 ml of THF together with 4.0 g (41.0 mmol) of 1-hexyn-3-ol and 11.3 g (42.9 mmol) of triphenylphosphine, and 9.1 ml (46.8 mmol) of DIAD are added over the course of 20 min with ice-cooling. After 18 h at RT, water is added, and the mixture is extracted a number of times with MTBE. The combined organic phases are washed with water and saturated sodium chloride soln., and the solution is dried using sodium sulfate. The residue remaining after removal of the solvents is purified by column chromatography (SiO$_2$, n-heptane:MTBE=2:1), giving 6-(1-ethynylbutoxy)-7,8-difluoro-2-pentylchroman as a yellow oil.

3.2 Preparation of 5,6-difluoro-3-pentyl-8-propyl-1,2,3,8-tetrahydropyrano-[3,2-f]chromene

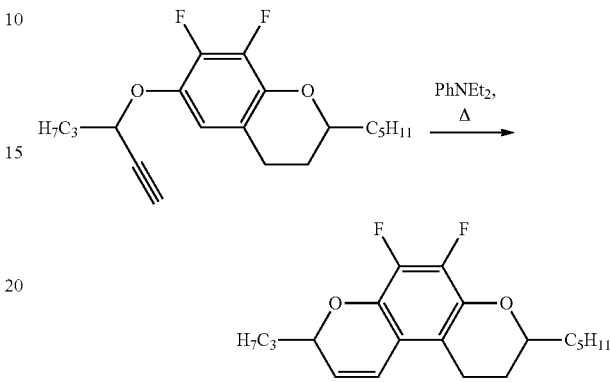

9.0 g (26.8 mmol) of 6-(1-ethynylbutoxy)-7,8-difluoro-2-pentylchroman are heated at 205° C. for 3 h in 90 ml of N,N-diethylaniline. The batch is diluted with MTBE and washed a number of times with 3 N HCl. The organic phase is dried using sodium sulfate and evaporated to dryness. The residue is purified by column chromatography (SiO$_2$, n-heptane:MTBE=4:1), giving 5,6-difluoro-3-pentyl-8-propyl-1,2,3,8-tetrahydropyrano[3,2-f]-chromene as a pale-brown oil.

3.3 Preparation of 5,6-difluoro-3-pentyl-8-propyl-1,2,3,8,9,10-hexahydropyrano[3,2-f]chromene

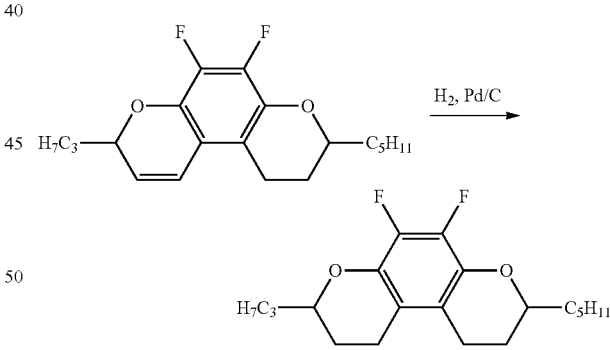

8.0 g (23.8 mmol) of 5,6-difluoro-3-pentyl-8-propyl-1,2,3,8-tetrahydropyrano[3,2-f]chromene are hydrogenated at atmospheric pressure for 5 h in toluene and in the presence of Pd/C (5% of Pd). The reaction solution is filtered, and the filtrate is evaporated to dryness. The residue is purified by column chromatography (SiO$_2$, n-heptane:1-chlorobutane=1:1). The further purification is carried out by recrystallisation from ethanol, giving a 1:1 mixture of isomeric 5,6-difluoro-3-pentyl-8-propyl-1,2,3,8,9,10-hexahydropyrano [3,2-f]chromenes. This is resolved, for example, by preparative HPLC.

Isomer 1 (m.p. 84° C.):

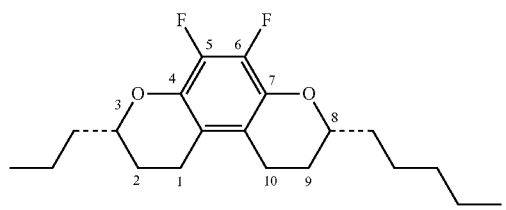

Δε=−10.2
Δn=0.0463
γ₁=295 mPa·s
C 84 I

¹H-NMR (500 MHz, CHCl₃): δ=3.92-3.80 (m, 2H, 3-H, 8-H), 2.57-2.33 (m, 4H, H$_{aliph.}$), 2.02-1.91 (m, 2H, H$_{aliph.}$), 1.76-1.60 (m, 4H, H$_{aliph.}$), 1.57-1.36 (m, 8H, H$_{aliph.}$), 1.33-1.17 (m, 6H, H$_{aliph.}$), 0.93-0.78 (m, 6H, H$_{aliph.}$).

¹⁹F-NMR (235 MHz, CHCl₃): δ=−163.4 (s, 2F).

MS (EI): m/e (%)=338 (100, M⁺).

Isomer 2 (m.p. 61° C.):

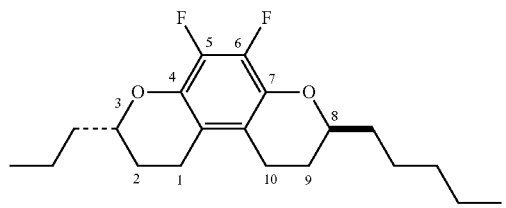

Δε=−11.8
Δn=0.0464
γ₁=488 mPa·s
C 61 I

¹H-NMR (500 MHz, CHCl₃): δ=3.92-3.84 (m, 2H, 3-H, 8-H), 2.56-2.48 (m, 4H, H$_{aliph.}$), 2.08-1.99 (m, 2H, H$_{aliph.}$), 1.84-1.66 (m, 4H, H$_{aliph.}$), 1.64-1.41 (m, 8H, H$_{aliph.}$), 1.36-1.29 (m, 6H, H$_{aliph.}$), 0.97 (t, 3H, J=7.2 Hz, Me), 0.90 (t, 3H, J=7.1 Hz, Me).

Example 4

5,6-Difluoro-3-propyl-8-(4-propylcyclohexyl)-2,3,7,8,9,10-hexahydro-1H-benzo[f]chromene

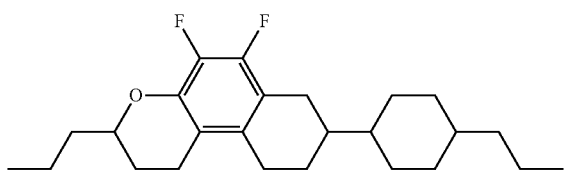

4.1 Preparation of 7,8-difluoro-3,4-dihydronaphthalen-2-yl trifluoromethane-sulfonate

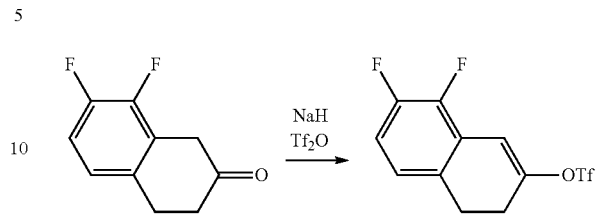

54.0 g (1.35 mol) of sodium hydride (60% suspension in paraffin oil) are washed with pentane and suspended in 1.25 l of diethyl ether. A soln. of 120.0 g (0.66 mol) of 7,8-difluoro-3,4-dihydro-1H-naphthalen-2-one in 750 ml of diethyl ether is slowly metered into the suspension, and, when the addition is complete, the batch is stirred at RT for 30 min. The mixture is cooled to 0° C., and 120.0 ml (0.71 mol) of trifluoroacetic anhydride are added dropwise. When the addition is complete, the batch is stirred at 0° C. for 2 h and added to dil. hydrochloric acid. The mixture is extracted a number of times with MTBE, and the combined organic phases are washed with sat. sodium chloride soln. The solution is filtered absorptively (SiO₂, MTBE), and the filtrate is evaporated to dryness. The residue is treated with n-heptane:toluene=7:3, and the organic phase is separated off. The solution is evaporated to dryness, and the residue is purified by column chromatography (SiO₂, n-heptane:toluene=7:3), giving 7,8-difluoro-3,4-dihydronaphthalen-2-yl trifluoromethanesulfonate as a yellow oil.

4.2 Preparation of 5,6-difluoro-3-(4-propylcyclohexyl)-1,2-dihydronaphthalene

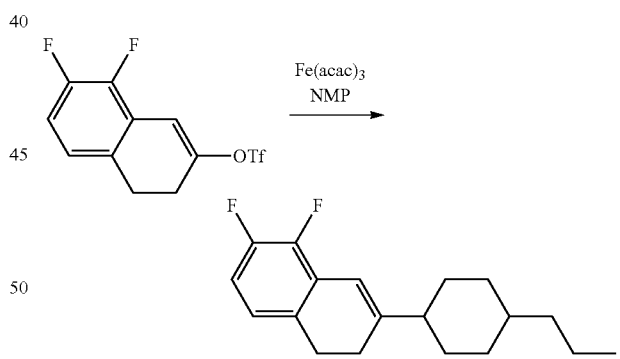

9.0 g (28.6 mmol) of 7,8-difluoro-3,4-dihydronaphthalen-2-yl trifluoromethanesulfonate are initially introduced at −30° C. in 500 ml of THF together with 550 mg (1.55 mmol) of Fe(acac)₃ and 30 ml of NMP. A solution of 4-propylcyclohexylmagnesium bromide produced from 30.0 g (0.15 mol) of 4-bromopropylcyclohexane and 3.6 g (0.15 mol) of magnesium turnings in 350 ml of diethyl ether is rapidly metered in. When the addition is complete, the mixture is stirred at −30° C. for 30 min and added to sat. ammonium chloride soln. The mixture is extracted a number of times with MTBE, and the combined organic phases are washed with sat. sodium chloride soln. The solution is dried using sodium sulfate and evaporated to dryness. The residue is purified by column chromatography (SiO$_2$, n-heptane), giving 5,6-difluoro-3-(4-propylcyclohexyl)-1,2-dihydronaphthalene as a colourless oil.

4.3 Preparation of 7,8-difluoro-2-(4-propylcyclohexyl)-1,2,3,4-tetrahydronaphthalene

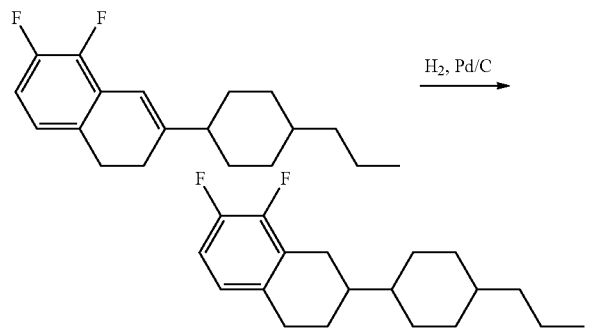

76.0 g (0.26 mol) of 5,6-difluoro-3-(4-propylcyclohexyl)-1,2-dihydronaphthalene are hydrogenated at RT and atmospheric pressure for 19 h in 500 ml of THF in the presence of Pd/C (5% of Pd). The reaction solution is filtered and evaporated to dryness. The residue is used for the following reaction without further purification.

4.4 Preparation of 3,4-difluoro-6-(4-propylcyclohexyl)-5,6,7,8-tetrahydronaphthalen-2-ol

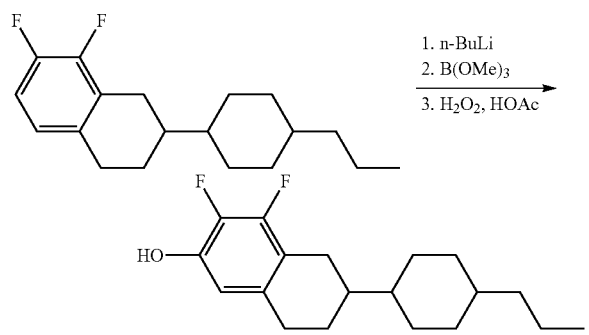

77.0 g (about 0.26 mol) of crude 7,8-difluoro-2-(4-propylcyclohexyl)-1,2,3,4-tetrahydronaphthalene are initially introduced in 500 ml of THF, and 200.0 ml (0.32 mol) of n-BuLi (15% soln. in hexane) are added at −70° C. After 3 h at this temperature, 37.0 ml (0.33 mol) of trimethyl borate are added dropwise, the batch is warmed to 0° C., and 80 ml of dilute acetic acid (about 30%) are added. The mixture is warmed to 30° C., and 70 ml of hydrogen peroxide solution (35%) are carefully added. When the addition is complete, the mixture is stirred at RT for 2 h. Water is added, and the batch is acidified using dil. hydrochloric acid. The solution is extracted a number of times with MTBE, and the combined organic phases are washed successively with water, sat. sodium chloride soln. and ammonium iron(II) sulfate soln. The solution is dried using sodium sulfate and evaporated to dryness. The crude product is purified by column chromatography (SiO$_2$, toluene). The further purification is carried out by crystallisation from n-heptane, giving 3,4-difluoro-6-(4-propylcyclohexyl)-5,6,7,8-tetrahydronaphthalen-2-ol as a colourless solid.

4.5 Preparation of 6-(1-ethynylbutoxy)-7,8-difluoro-2-(4-propylcyclohexyl)-1,2,3,4-tetrahydronaphthalene

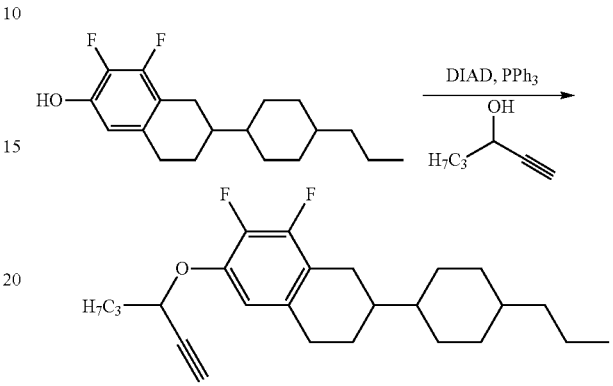

7.0 g (22.7 mmol) of 3,4-difluoro-6-(4-propylcyclohexyl)-5,6,7,8-tetrahydronaphthalen-2-ol are initially introduced in 90 ml of THF together with 2.70 ml (24.0 mmol) of 1-hexyn-3-ol and 6.60 g (25.2 mmol) of triphenylphosphine. 5.3 ml (46.8 mmol) of DIAD in 10 ml of THF are added over the course of 20 min with ice-cooling. After 19 h at RT, water is added, and the mixture is extracted a number of times with MTBE. The combined organic phases are washed with water and saturated sodium chloride soln., and the solution is dried using sodium sulfate. The residue remaining after removal of the solvents is purified by column chromatography (SiO$_2$, n-heptane MTBE=2:1), giving 6-(1-ethynylbutoxy)-7,8-difluoro-2-(4-propylcyclohexyl)-1,2,3,4-tetrahydronaphthalene as a colourless solid.

4.6 Preparation of 5,6-difluoro-3-propyl-8-(4-propylcyclohexyl)-7,8,9,10-tetrahydro-3H-benzo[f]chromene

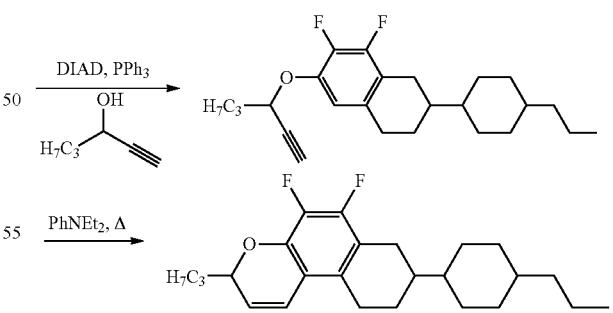

4.5 g (11.6 mmol) of 6-(1-ethynylbutoxy)-7,8-difluoro-2-(4-propylcyclohexyl)-1,2,3,4-tetrahydronaphthalene are heated at 200° C. for 2 h in 45 ml of N,N-diethylaniline. After cooling, the batch is added to a mixture of 2 N hydrochloric acid and ice, and the mixture is extracted with MTBE. The organic phase is washed with 2 N hydrochloric acid and water, and the solution is dried using sodium sulfate. The residue remaining after removal of the solvent is purified by column chromatography (SiO$_2$, n-heptane:toluene=9:1), giving 5,6-difluoro-3-propyl-8-(4-propylcyclohexyl)-7,8,9,10-tetrahydro-3H-benzo[f]chromene as a yellow solid.

4.7 Preparation of 5,6-difluoro-3-propyl-8-(4-propylcyclohexyl)-2,3,7,8,9,10-hexahydro-1H-benzo[f]chromene

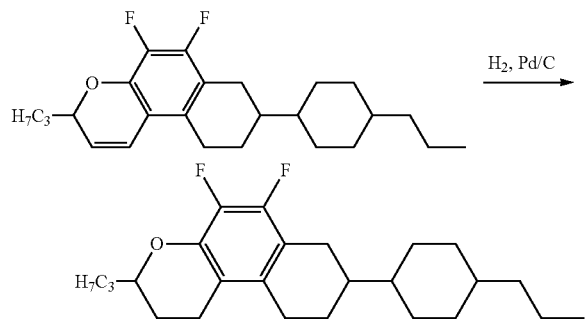

5.0 g (about 11.4 mmol) of 5,6-difluoro-3-propyl-8-(4-propylcyclohexyl)-7,8,9,10-tetrahydro-3H-benzo[f]chromene are hydrogenated at atmospheric pressure in THF and in the presence of Pd/C (5% of Pd). The reaction solution is filtered, and the filtrate is evaporated to dryness. The residue is purified by column chromatography (SiO$_2$, n-heptane:toluene=9:1). The further purification is carried out by recrystallisation from ethanol, giving a 1:1 mixture of isomeric 5,6-difluoro-3-propyl-8-(4-propylcyclohexyl)-2,3,7,8,9,10-hexahydro-1H-benzo[f]chromenes (m.p. 89° C.). This can be resolved, for example, by preparative HPLC.

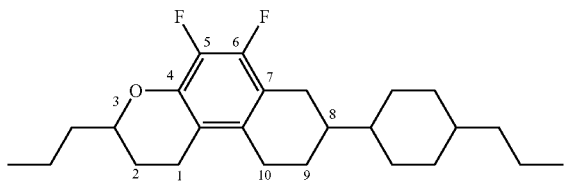

Δε=−7.5

Δn=0.0879

C 89 N 113 I $^1$H-NMR (500 MHz, CHCl$_3$): δ=4.01-3.90 (m, 1H, 3-H), 2.84-2.77 (m, 1H), 2.69-2.22 (m, 5H), 2.07-1.93 (m, 2H), 1.86-1.66 (m, 5H), 1.62-1.43 (m, 4H), 1.41-1.26 (m, 4H), 1.24-1.11 (m, 4H), 1.08-0.83 (m, 10H).

$^{19}$F-NMR (376 MHz, CHCl$_3$): δ=−146.4 (dd, 1F, J=21.1 Hz, J=3.4 Hz), −165.9 (dd 1F, J=21.1 Hz, J=11.7 Hz).

MS (EI): m/e (%)=390 (100, M$^+$), 321 (78).

Example 5

8-Ethoxy-5,6-difluoro-3-(4-propylcyclohexyl)-2,3-dihydro-1H-benzo[f]chromene

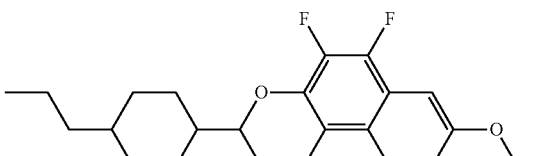

5.1 Preparation of 7,8-difluoro-3-trimethylsilanylnaphthalen-2-ol

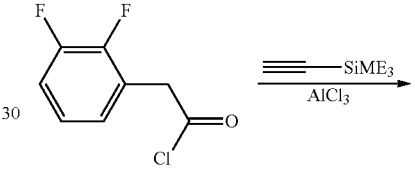

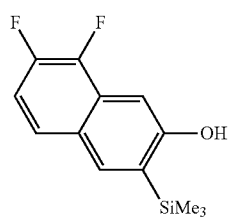

A solution of 50.0 g (0.26 mol) of 2,3-difluorophenylacetyl chloride in 100 ml of dichloromethane is slowly added to a suspension of 71.5 g (0.53 mol) of aluminium(III) chloride in 300 ml of dichloromethane at −20° C. After 30 min at this temperature, trimethylsilylacetylene is metered in, and the mixture is stirred for 30 min. The batch is added to ice-water and acidified using hydrochloric acid. The organic phase is separated off, and the aqueous phase is extracted with ethyl acetate. The combined organic phases are washed successively with sat. sodium hydrogencarbonate soln. and sat. sodium chloride soln. The solution is dried using sodium sulfate and evaporated to dryness. The residue is purified by column chromatography (SiO$_2$, n-heptane:ethyl acetate=9:1), giving 7,8-difluoro-3-trimethylsilanylnaphthalen-2-ol as a brown oil.

5.2 Preparation of (3-ethoxy-5,6-difluoronaphthalen-2-yl)trimethylsilane

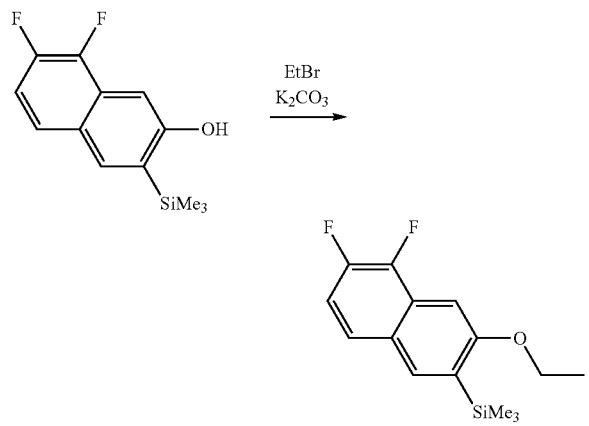

54.7 g (about 0.12 mol) of 7,8-difluoro-3-trimethylsilanylnaphthalen-2-ol are stirred at 80° C. for 19 h together with 19.5 ml (0.26 mol) of bromoethane and 34.5 g (0.25 mol) of potassium carbonate in 400 ml of ethyl methyl ketone. The batch is filtered, and the residue is washed with ethyl methyl ketone. The filtrate is concentrated, and the residue is taken up in MTBE. The solution is washed with water and sat. sodium chloride soln. and dried using sodium sulfate. The residue remaining after removal of the solvent is purified by column chromatography (SiO$_2$, toluene:ethyl acetate=9:1), giving (3-ethoxy-5,6-difluoronaphthalen-2-yl)trimethylsilane as a dark-brown solid.

5.3 Preparation of 7-ethoxy-1,2-difluoronaphthalene

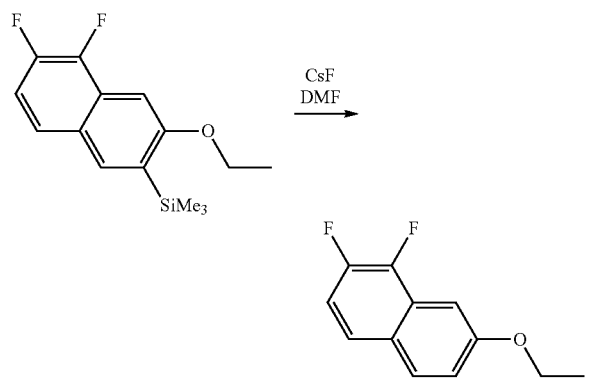

44.0 g (about 81.6 mmol) of (3-ethoxy-5,6-difluoronaphthalen-2-yl)trimethylsilane are stirred at 100° C. for 20 h together with 26.3 g (0.17 mol) of caesium fluoride in 300 ml of DMF. After cooling, the mixture is diluted with water and extracted a number of times with MTBE. The combined organic phases are washed with water and sat. sodium chloride soln., and the solution is dried using sodium sulfate. The brown oil remaining after removal of the solvent is purified by column chromatography (SiO$_2$, toluene:ethyl acetate=9:1), giving 7-ethoxy-1,2-difluoronaphthalene as a brown oil.

5.4 Preparation of 6-ethoxy-3,4-difluoronaphthalen-2-ol

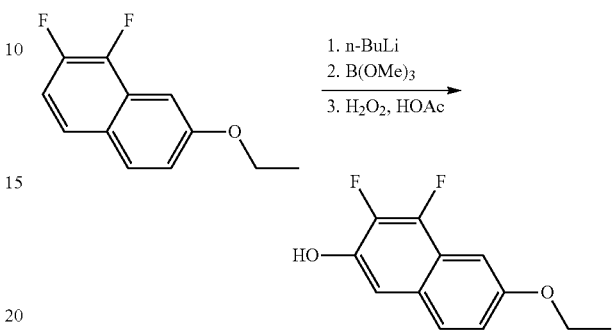

30.0 g (about 0.1 mol) of 7-ethoxy-1,2-difluoronaphthalene are initially introduced in 300 ml of THF, and 130.0 ml (0.21 mol) of n-BuLi (15% soln. in hexane) are added at −75° C. After 1 h at this temperature, 25.0 ml (0.22 mol) of trimethyl borate are added dropwise, and the batch is warmed to −10° C. 50 ml of dilute acetic acid (about 30%) are added, and the mixture is warmed to 30° C. 40 ml of hydrogen peroxide solution (35%) are carefully added, and the mixture is stirred vigorously for 18 h. Water is added, and ammonium iron(II) sulfate is added to the batch. The solution is extracted a number of times with MTBE, and the combined organic phases are washed successively with water and sat. sodium chloride soln. The solution is dried using sodium sulfate and evaporated to dryness. The crude product is purified by column chromatography (SiO$_2$, toluene:ethyl acetate=9:1), giving 6-ethoxy-3,4-difluoronaphthalen-2-ol as a pale-brown solid.

5.5 Preparation of 7-ethoxy-1,2-difluoro-3-[1-(4-propylcyclohexyl)prop-2-ynyloxy]naphthalene

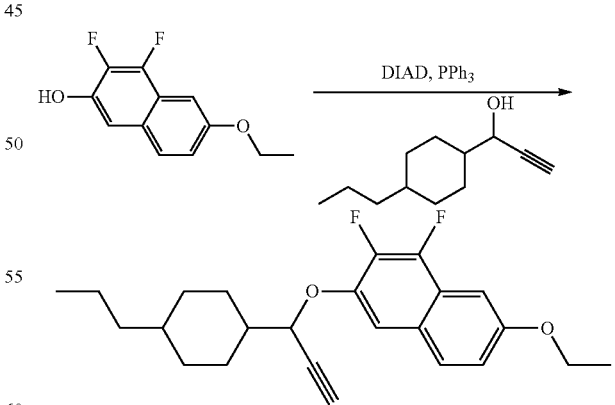

10.5 g (46.8 mmol) of 6-ethoxy-3,4-difluoronaphthalen-2-ol are initially introduced in 100 ml of THF together with 10.0 g (55.5 mmol) of 1-(4-propylcyclohexyl)prop-2-yn-1-ol and 15.0 g (57.2 mmol) of triphenylphosphine, and 11.5 ml (59.1 mmol) of DIAD are added over the course of 20 min with ice-cooling. After 18 h at RT, water is added, and the mixture is extracted a number of times with MTBE. The combined organic phases are washed with water and saturated sodium chloride soln., and the solution is dried using sodium sulfate. The residue remaining after removal of the solvents is purified by column chromatography (SiO$_2$, n-heptane:MTBE=2:1). The further purification is carried out by recrystallisation from n-heptane, giving 7-ethoxy-1,2-difluoro-3-[1-(4-propylcyclohexyl)prop-2-ynyloxy]naphthalene as a yellowish solid.

5.6 Preparation of 8-ethoxy-5,6-difluoro-3-(4-propylcyclohexyl)-3H-benzo-[f]chromene

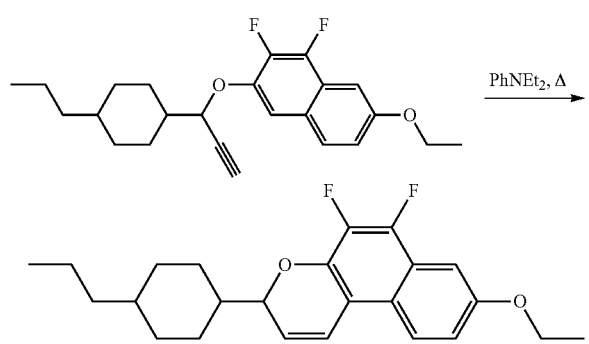

7.75 g (about 18.6 mmol) of 7-ethoxy-1,2-difluoro-3-[1-(4-propylcyclohexyl)prop-2-ynyloxy]naphthalene are heated at 205° C. for 4.5 h in 80 ml of N,N-diethylaniline. The batch is diluted with MTBE and washed a number of times with hydrochloric acid. The organic phase is dried using sodium sulfate and evaporated to dryness. The residue is purified by column chromatography (SiO$_2$, n-heptane:MTBE=4:1). The further purification is carried out by recrystallisation from n-heptane, giving 8-ethoxy-5,6-difluoro-3-(4-propylcyclohexyl)-3H-benzo[f]chromene as a yellow solid.

5.7 Preparation of 8-ethoxy-5,6-difluoro-3-(4-propylcyclohexyl)-2,3-dihydro-1H-benzo[f]chromene

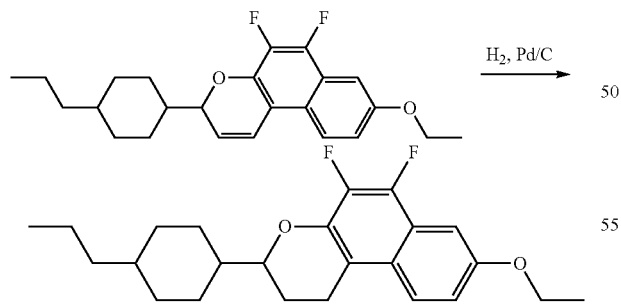

5.1 g (13.1 mmol) of 8-ethoxy-5,6-difluoro-3-(4-propylcyclohexyl)-3H-benzo[f]chromene are hydrogenated at atmospheric pressure in THF and in the presence of Pd/C (5% of Pd). The reaction solution is filtered, and the filtrate is evaporated to dryness. The residue is recrystallised from ethyl acetate, giving 8-ethoxy-5,6-difluoro-3-(4-propylcyclohexyl)-2,3-dihydro-1H-benzo[f]chromene as a colourless solid (m.p. 158° C.).

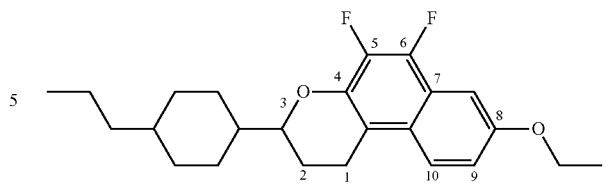

$\Delta\epsilon$=−5.4
$\Delta n$=0.1550
C 158 N 159 I
$^1$H-NMR (400 MHz, CHCl$_3$): δ=7.64 (dd, 1H, J=9.2 Hz, J=1.6 Hz, 10-H), 7.24 (d, 1H, J=2.4 Hz, 7a-H), 7.12 (dd, 1H, J=9.2 Hz, J=2.4 Hz, 9-H), 4.14 (q, 2H, J=7.0 Hz, OCH$_2$CH$_3$), 3.84-3.79 (m, 1H, 3-H), 3.08-3.00 (m, 1H, 1-H), 2.97-2.87 (m, 1H, 1-H), 2.20-2.06 (m, 2H, H$_{aliph.}$), 1.94-1.79 (m, 4H, H$_{aliph.}$), 1.71-1.60 (m, 1H, H$_{aliph.}$), 1.47 (t, 3H, J=7.0 Hz, OCH$_2$CH$_3$), 1.38-1.11 (m, 7H, H$_{aliph.}$), 1.00-0.86 (m, 5H, H$_{aliph.}$).
$^{19}$F-NMR (376 MHz, CHCl$_3$): δ=−152.5 (dd, 1F, J=17.8 Hz, J=1.2 Hz), −160.5 (d, 1F, J=17.8 Hz).
MS (EI): m/e (%)=388 (89, M$^+$), 237 (100).

The invention claimed is:
1. A compound of the formula I:

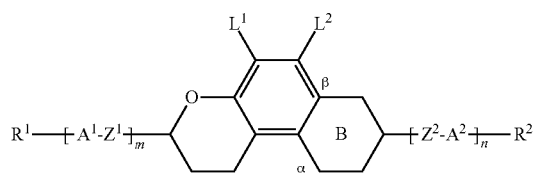

in which
m and n are each, independently of one another, 0, 1, 2 or 3, where m+n≦4;
L$^1$ and L$^2$ each, independently of one another, denote H, halogen, CN, CF$_3$, CHF$_2$, CH$_2$F or CH$_3$;
A$^1$ and A$^2$ each, independently of one another, denote
(a) 1,4-phenylene, in which =CH— may be replaced once or twice by =N— and which may be unsubstituted or mono- to tetrasubstituted, independently of one another, by —CN, —F, —Cl, —Br, —I, C$_1$-C$_6$-alkanyl which is unsubstituted or mono- or polysubstituted by fluorine and/or chlorine, or C$_1$-C$_6$-alkoxy which is unsubstituted or mono- or polysubstituted by fluorine and/or chlorine,
(b) 1,4-cyclohexylene, 1,4-cyclohexenylene or 1,4-cyclohexadienylene, in which —CH$_2$— may be replaced once or twice, independently of one another, by —O— or —S— in such a way that heteroatoms are not linked directly, and which may be unsubstituted or mono- or polysubstituted by —F and/or —Cl, or
(c) bicyclo[1.1.1]pentane-1,3-diyl, bicyclo[2.2.2]octane-1,4-diyl or spiro[3.3]heptane-2,6-diyl;
Z$^1$ and Z$^2$ each, independently of one another, denote a single bond, or a group selected from the group consisting of —CF$_2$O—, —OCF$_2$—, —CH$_2$CH$_2$—, —CF$_2$CF$_2$—, —CF$_2$CH$_2$—, —CH$_2$CF$_2$—, —(CO)O—, —O(CO)—, —CH$_2$O—, —OCH$_2$—, —CF=CH—, —CH=CF—, —CF=CF—, —CH═CH—, and —C≡C—, or a combination of two of said groups groups, where O atoms are not linked directly;

R¹ and R², independently of one another, denote hydrogen, an alkanyl, or alkoxy radical having 1 to 15 C atoms, or an alkenyl or alkynyl radical having 2 to 15 C atoms, which alkanyl, alkoxy, alkenyl or alkynyl radical is unsubstituted, monosubstituted by —CN or mono- or polysubstituted by —F, —Cl and/or —Br, in which alkanyl, alkoxy, alkenyl or alkynyl radical one or more CH₂ groups may each be replaced, independently of one another, by —O—, —S—, —SO₂—, —CO—, —(CO)O—, —O(CO)— or —O(CO)O— in such a way that heteroatoms are not linked directly, or denote —F, —Cl, —Br, —CN, —SCN or —SF₅; and ring B denotes one of the following rings

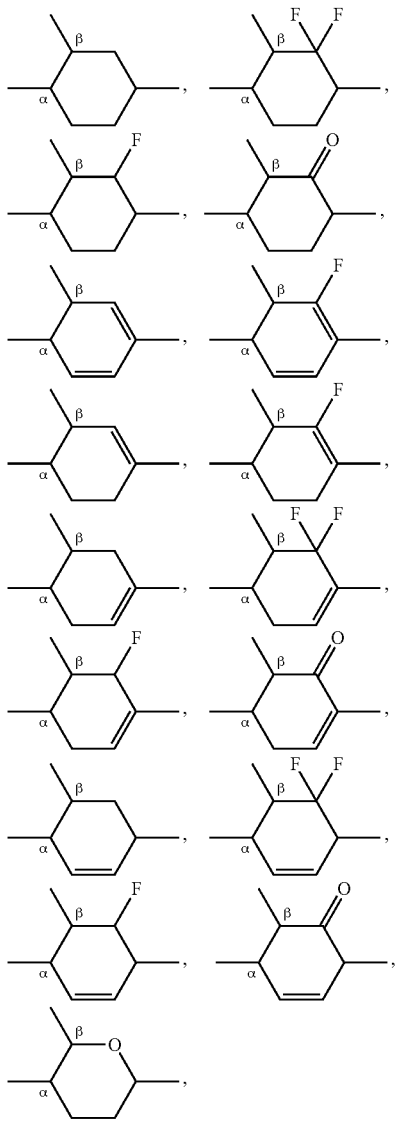

where

A¹ and A² or Z¹ and Z² may each have identical or different meanings if m or n is greater than 1, where R¹ and R² do not simultaneously denote H, and where in the case where R¹═H and m=0 or R²═H and n=0, then ring B denotes a pyran of the formula

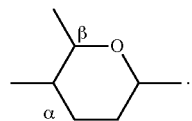

2. A compound according to claim 1, wherein one of the radicals L¹ and L² denotes F or both of the radicals L¹ and L² denote F.

3. A compound according to claim 1, wherein the substituents L¹ and L² denote F.

4. A compound according to claim 1, which is a compound of one of formulae IA to IF:

IA

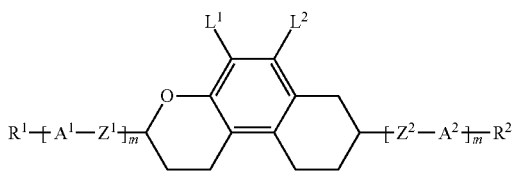

IB

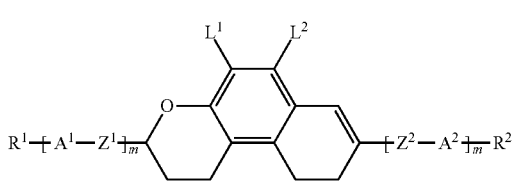

IC

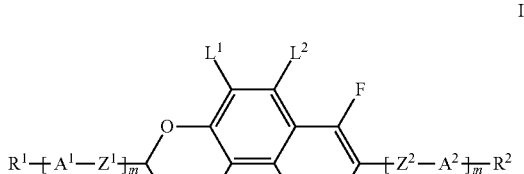

ID

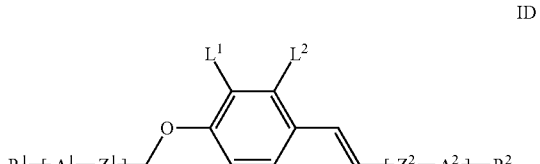

IE

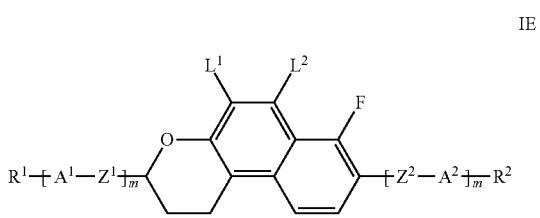

-continued

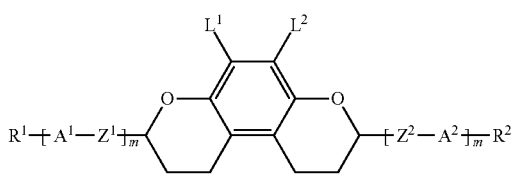

in which $R^1$, $R^2$, $A^1$, $A^2$, $L^1$, $L^2$, $Z^1$ and $Z^2$ have the same meanings as defined for the compound of formula I.

5. A compound according to claim 1, wherein $Z^1$ and $Z^2$, independently of one another, denote a single bond, —$CF_2O$—, —$OCF_2$—, —$OCH_2$—, —$CH_2O$—, —$CF_2CF_2$—, —CH=CH—, —CF=CH—, —CH=CF— or —CF=CF—.

6. A compound according claim 1, wherein $A^1$ and $A^2$, independently of one another, denote

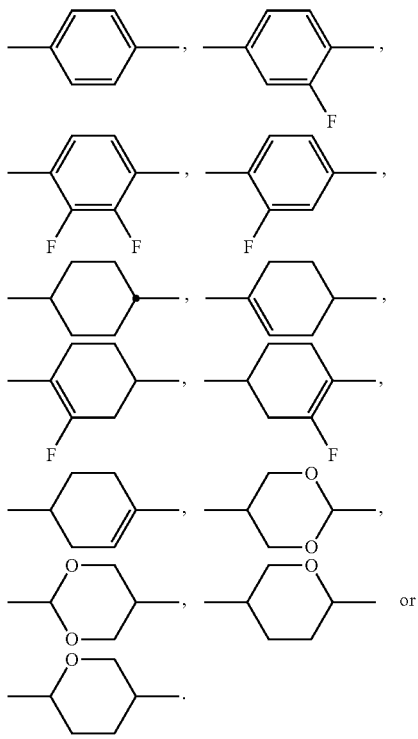

7. A compound according to claim 1, wherein $R^1$ and $R^2$ are each, independently of one another, an alkanyl radical, or alkoxy radical having 1 to 7 carbon atoms or alkenyl radical having 2 to 7 carbon atoms, which alkanyl, alkoxy or alkenyl radical is unsubstituted or mono- or polysubstituted by halogen, or denote fluorine or hydrogen.

8. A compound according claim 1, wherein m and n are both zero, and $R^1$ and $R^2$ are each, independently of one another, an unbranched alkanyl radical, or alkoxy radical having 1 to 7 carbon atoms or alkenyl radical having 2 to 7 carbon atoms.

9. A compound according to claim 1, wherein m+n=1, and $A^1$, $A^2$, independently of one another, denote

10. A method of generating an optical effect comprising applying a voltage to a liquid-crystalline medium comprising one or more compounds according to claim 1.

11. A liquid-crystalline medium comprising at least two compounds, one of which is at least one compound according to claim 1.

12. An electro-optical display element containing a liquid-crystalline medium according to claim 11.

13. A process for preparing a compound of formula I according to claim 1, comprising etherifying a compound of the following formula

in which n, $A^2$ and $Z^2$ are as defined for formula I, and $R^{22}$ denotes hydrogen, an alkanyl, or alkoxy radical having 1 to 15 C atoms, or an alkenyl or alkynyl radical having 2 to 15 C atoms, which alkanyl, alkoxy, alkenyl or alkynyl radical is unsubstituted, monosubstituted by —CN or mono—or polysubstituted by —F, —Cl and/or —Br, in which alkanyl, alkoxy, alkenyl or alkynyl radical one or more $CH_2$ groups may each be replaced, independently of one another, by —O—, —S—, —$SO_2$—, —CO—, —(CO)O—, —O(CO)— or —O(CO)O— in such a way that heteroatoms are not linked directly, or denotes —F, —Cl, —Br, —CN, —SCN, —$SF_5$, —OTs, OTf, OMes, —$B(OH)_2$, —$B(O\text{-alkyl})_2$ or —$B<(O—C_{2-10}\text{-alkylene-O})$, on the hydroxyl group by an organic radical to give a compound of the follwing formula

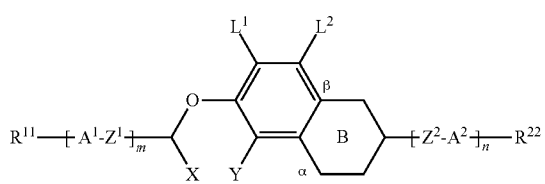

in which m, n, $A^1$, $Z^1$, $A^2$ and $Z^2$ are as defined for formula I, $R^{11}$ and $R^{22}$ independently of one another, denote hydrogen, an alkanyl, or alkoxy radical having 1 to 15 C atoms, or an alkenyl or alkynyl radical having 2 to 15 C atoms, which alkanyl, alkoxy, alkenyl or alkynyl radical is unsubstituted, monosubstituted by —CN or mono— or polysubstituted by —F, —Cl and/or —Br, in which alkanyl, alkoxy, alkenyl or alkynyl radical one or more $CH_2$ groups may each be replaced, independently of one another, by —O—, —S—, —$SO_2$—, —CO—, —(CO)O—, —O(CO)— or —O(CO)O— in such a way that heteroatoms are not linked directly, or denote —F, —Cl, —Br, —CN, —SCN, —$SF_5$, —OTs, —OTf, —OMes, —$B(OH)_2$, —$B(O\text{-alkyl})_2$ or —B<(O—$C_{2-10}$-alkylene-O), X denotes —$CH_2CH_2Br$ or —C≡CH—, and Y denotes H or Br, and cyclizing in a further process step.

* * * * *

UNITED STATES PATENT AND TRADEMARK OFFICE
CERTIFICATE OF CORRECTION

PATENT NO. : 8,303,844 B2
APPLICATION NO. : 12/744804
DATED : November 6, 2012
INVENTOR(S) : Jansen et al.

Page 1 of 3

It is certified that error appears in the above-identified patent and that said Letters Patent is hereby corrected as shown below:

In the Claims:

Column 86, line 22 thru Column 87, line 12, reads:

4. A compound according to claim 1, which is a compound of one of formulae IA to IF:

IA

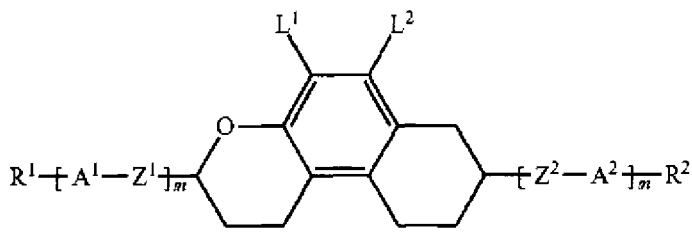

IB

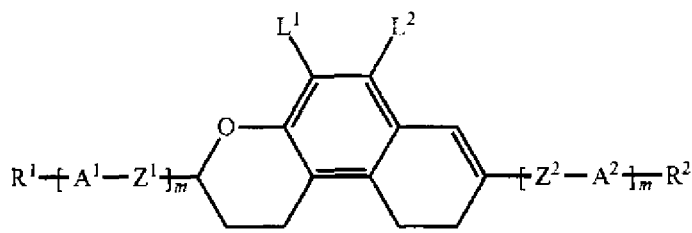

IC

Signed and Sealed this
Sixteenth Day of April, 2013

Teresa Stanek Rea
*Acting Director of the United States Patent and Trademark Office*

CERTIFICATE OF CORRECTION (continued)
U.S. Pat. No. 8,303,844 B2

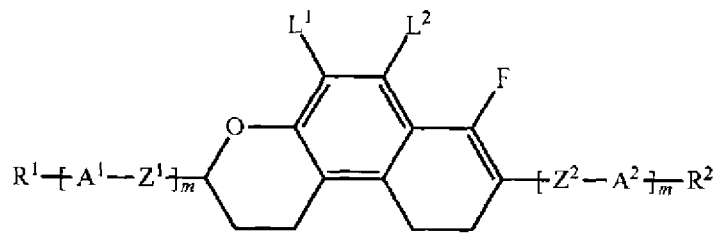

ID

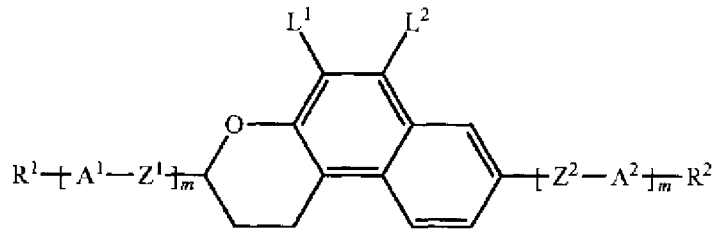

IE

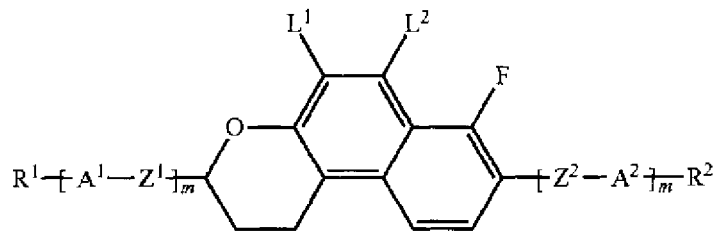

IF

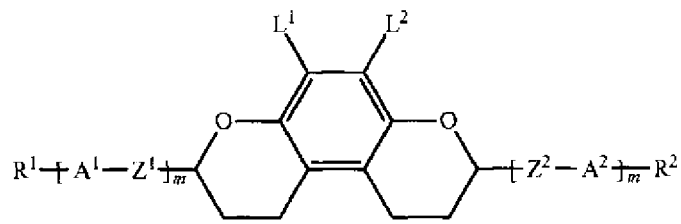

in which $R^1$, $R^2$, $A^1$, $A^2$, $L^1$, $L^2$, $Z^1$ and $Z^2$ have the same meanings as defined for the compound of formula I.

It should read:

4. A compound according to claim 1, which is a compound of one of formulae IA to IF:

CERTIFICATE OF CORRECTION (continued)
U.S. Pat. No. 8,303,844 B2

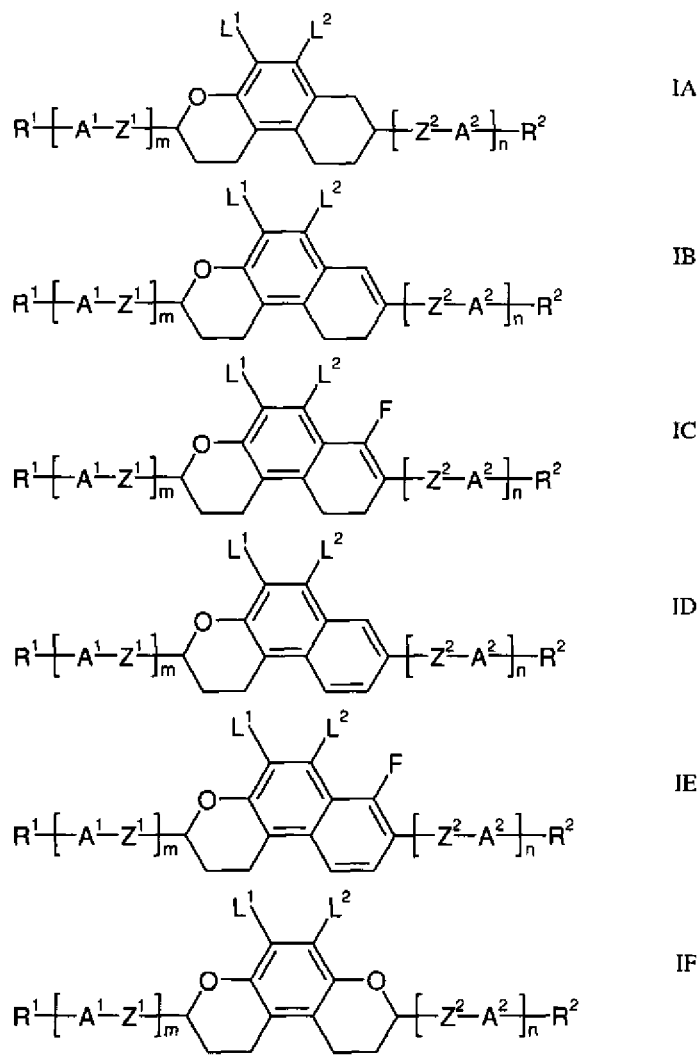

in which $R^1$, $R^2$, $A^1$, $A^2$, $L^1$, $L^2$, $Z^1$ and $Z^2$ have the same meanings as defined for the compound of formula I.